United States Patent
Hardin et al.

(10) Patent No.: US 7,329,492 B2
(45) Date of Patent: Feb. 12, 2008

(54) METHODS FOR REAL-TIME SINGLE MOLECULE SEQUENCE DETERMINATION

(75) Inventors: Susan Hardin, Bellaire, TX (US); Xiaolian Gao, Houston, TX (US); James Briggs, Katy, TX (US); Richard Willson, Houston, TX (US); Shiao-Chun Tu, Houston, TX (US)

(73) Assignee: Visigen Biotechnologies, Inc. TX (US)

( * ) Notice: Subject to any disclaimer, the term of this patent is extended or adjusted under 35 U.S.C. 154(b) by 368 days.

(21) Appl. No.: 11/007,797

(22) Filed: Dec. 8, 2004

(65) Prior Publication Data

US 2005/0260614 A1    Nov. 24, 2005

Related U.S. Application Data

(62) Division of application No. 09/901,782, filed on Jul. 9, 2001.

(60) Provisional application No. 60/216,594, filed on Jul. 7, 2000.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search ............... 435/6; 536/23.1, 24.3
See application file for complete search history.

(56) References Cited

U.S. PATENT DOCUMENTS

| 6,818,395 B1 * | 11/2004 | Quake et al. ............. 435/6 |
| 6,911,345 B2 * | 6/2005 | Quake et al. ............. 436/532 |
| 2003/0044781 A1 * | 3/2003 | Korlach et al. ........... 435/6 |

* cited by examiner

*Primary Examiner*—Ethan Whisenant
(74) *Attorney, Agent, or Firm*—Robert W Strozier

(57) ABSTRACT

A sequencing methodology is disclosed that allows a single DNA or RNA molecule or portion thereof to be sequenced directly and in substantially real time. The methodology involves engineering a polymerase and/or dNTPs with atomic and/or molecular tags that have a detectable property that is monitored by a detection system.

23 Claims, 14 Drawing Sheets

```
Primer Strand:
    TOP    5'         GGT ACT AAG CGG CCG CAT G   3'
Template Strands:
    BOT- T  3'        CCA TGA TTC GCC GGC GTA CTC 5'
    BOT- C  3'        CCA TGA TTC GCC GGC GTA CCC 5'
    BOT- G  3'        CCA TGA TTC GCC GGC GTA CGC 5'
    BOT- A  3'        CCA TGA TTC GCC GGC GTA CAC 5'
    BOT- 3T 3'        CCA TGA TTC GCC GGC GTA CTT TC 5'
    BOT- Sau 3'       CCA TGA TTC GCC GGC GTA CCT AG 5'
```

Incorporate: GATC  AG        AAAG
(5' to 3')

SEQUENCE LISTING

```
<160> NUMBER OF SEQ ID NOS: 57

<210> SEQ ID NO 1
<211> LENGTH: 19
<212> TYPE: DNA
<213> ORGANISM: Artificial
```

```
<220> FEATURE:
<223> OTHER INFORMATION: Primer strand used to test incorporation of
      gamma-tagged dNTPs using Taq DNA Polymerase I.
<220> FEATURE:
<221> NAME/KEY: primer_bind
<222> LOCATION: (1)..(19)
<223> OTHER INFORMATION: 5 ' to 3' primer strand called TOP

<400> SEQUENCE: 1
ggtactaagc ggccgcatg                                                      19

<210> SEQ ID NO 2
<211> LENGTH: 21
<212> TYPE: DNA
<213> ORGANISM: Artificial
<220> FEATURE:
<223> OTHER INFORMATION: Templates strand used to test incorporation of
      gamma-tagged dNTPs using Taq DNA Polymerase I.
<220> FEATURE:
<221> NAME/KEY: CDS
<222> LOCATION: (1)..(21)
<223> OTHER INFORMATION: 3' to 5' template strand BOT-T

<400> SEQUENCE: 2
ccatgattcg ccggcgtact c                                                   21

<210> SEQ ID NO 3
<211> LENGTH: 21
<212> TYPE: DNA
<213> ORGANISM: Artificial
<220> FEATURE:
<223> OTHER INFORMATION: Template strand used to test incorporation of
      gamma-tagged dNTPs using Taq DNA Polymerase I.
<220> FEATURE:
<221> NAME/KEY: CDS
<222> LOCATION: (1)..(21)
<223> OTHER INFORMATION: 3' to 5' template strand called BOT-C

<400> SEQUENCE: 3
ccatgattcg ccggcgtacc c                                                   21

<210> SEQ ID NO 4
<211> LENGTH: 21
<212> TYPE: DNA
<213> ORGANISM: Artificial
<220> FEATURE:
<223> OTHER INFORMATION: Template strand used to test incorporation of
      gamma-tagged dNTPs using Taq DNA Polymerase I.
<220> FEATURE:
<221> NAME/KEY: CDS
<222> LOCATION: (1)..(21)
<223> OTHER INFORMATION: 3' to 5' template strand called BOT-G

<400> SEQUENCE: 4
ccatgattcg ccggcgtacg c                                                   21

<210> SEQ ID NO 5
<211> LENGTH: 21
<212> TYPE: DNA
<213> ORGANISM: Artificial
<220> FEATURE:
<223> OTHER INFORMATION: Template strand used to test incorporation of
      gamma-tagged dNTPs using Taq DNA Polymerase I.
<220> FEATURE:
<221> NAME/KEY: CDS
<222> LOCATION: (1)..(21)
<223> OTHER INFORMATION: 3' to 5' template strand called BOT-A

<400> SEQUENCE: 5
ccatgattcg ccggcgtaca c                                                   21
```

```
<210> SEQ ID NO 6
<211> LENGTH: 23
<212> TYPE: DNA
<213> ORGANISM: Artificial
<220> FEATURE:
<223> OTHER INFORMATION: Template strand used to test incorporation of
      gamma-tagged dNTPs using Taq DNA Polymerase I.
<220> FEATURE:
<221> NAME/KEY: CDS
<222> LOCATION: (1)..(23)
<223> OTHER INFORMATION: 3' to 5' template strand called BOT-3T

<400> SEQUENCE: 6
ccatgattcg ccggcgtact ttc                                          23

<210> SEQ ID NO 7
<211> LENGTH: 23
<212> TYPE: DNA
<213> ORGANISM: Artificial
<220> FEATURE:
<223> OTHER INFORMATION: Template strand used to test incorporation of
      gamma-tagged dNTPs using Taq DNA Polymerase I.
<220> FEATURE:
<221> NAME/KEY: CDS
<222> LOCATION: (1)..(23)
<223> OTHER INFORMATION: 3' to 5' template strand called BOT-Sau

<400> SEQUENCE: 7
ccatgattcg ccggcgtacc tag                                          23

<210> SEQ ID NO 8
<211> LENGTH: 38
<212> TYPE: DNA
<213> ORGANISM: Thermus aquaticus
<220> FEATURE:
<221> NAME/KEY: primer_bind
<222> LOCATION: (1)..(38)
<223> OTHER INFORMATION: TAQ forward primer

<400> SEQUENCE: 8
gcgaattcat gagggggatg ctgcccctct ttgagccc                          38

<210> SEQ ID NO 9
<211> LENGTH: 37
<212> TYPE: DNA
<213> ORGANISM: Thermus aquaticus
<220> FEATURE:
<221> NAME/KEY: primer_bind
<222> LOCATION: (1)..(37)
<223> OTHER INFORMATION: TAQ Pol I Reverse Primer

<400> SEQUENCE: 9
gcgaattcac cctccttggc ggagcgccag tcctccc                           37

<210> SEQ ID NO 10
<211> LENGTH: 37
<212> TYPE: DNA
<213> ORGANISM: Thermus aquaticus
<220> FEATURE:
<221> NAME/KEY: misc_feature
<222> LOCATION: (1)..(37)
<223> OTHER INFORMATION: Taq Pol I A293 Trunk

<400> SEQUENCE: 10
aatccatggg ccctggagga ggcccctgg ccccgc                            37

<210> SEQ ID NO 11
<211> LENGTH: 832
<212> TYPE: PRT
```

<213> ORGANISM: Thermus aquaticus

<400> SEQUENCE: 11

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400
```

```
Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                    485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
```

-continued

```
                 820             825             830

<210> SEQ ID NO 12
<211> LENGTH: 19
<212> TYPE: PRT
<213> ORGANISM: Thermus aquaticus
<220> FEATURE:
<221> NAME/KEY: MISC_FEATURE
<222> LOCATION: (2)..(4)
<223> OTHER INFORMATION: Residues in native protein are Ser Trp Met
<220> FEATURE:
<221> NAME/KEY: MISC_FEATURE
<222> LOCATION: (6)..(6)
<223> OTHER INFORMATION: Residue in native protein is Gly
<220> FEATURE:
<221> NAME/KEY: MISC_FEATURE
<222> LOCATION: (8)..(9)
<223> OTHER INFORMATION: Residues in native protein are Pro Arg

<400> SEQUENCE: 12

Ala Xaa Xaa Xaa Phe Xaa Val Xaa Xaa Glu Ala Val Asp Pro Leu Met
1               5                   10                  15

Arg Arg Ala

<210> SEQ ID NO 13
<211> LENGTH: 32
<212> TYPE: DNA
<213> ORGANISM: Thermus aquaticus
<220> FEATURE:
<221> NAME/KEY: mutation
<222> LOCATION: (14)..(15)
<223> OTHER INFORMATION: Residue 643 Ala to Cys mutation forward primer:
      Codon GCC mutated to TGC

<400> SEQUENCE: 13
ccacacggag acctgcagct ggatgttcgg cg                                     32

<210> SEQ ID NO 14
<211> LENGTH: 32
<212> TYPE: DNA
<213> ORGANISM: Thermus aquaticus
<220> FEATURE:
<221> NAME/KEY: mutation
<222> LOCATION: (18)..(18)
<223> OTHER INFORMATION: Residue 643 Ala to Cys mutation reverse primer:
      antisense Codon GGC mutated to GCA

<400> SEQUENCE: 14
cgccgaacat ccacgagcag gtctccgtgt gg                                     32

<210> SEQ ID NO 15
<211> LENGTH: 35
<212> TYPE: DNA
<213> ORGANISM: Thermus aquaticus
<220> FEATURE:
<221> NAME/KEY: mutation
<222> LOCATION: (16)..(16)
<223> OTHER INFORMATION: Residue 647 Phe to Cys mutation forward primer:
      Codon ttc mutated to tgc

<400> SEQUENCE: 15
ccgccagctg gatgtgcggc gtcccccggg aggcc                                  35

<210> SEQ ID NO 16
<211> LENGTH: 35
<212> TYPE: DNA
<213> ORGANISM: Thermus aquaticus
<220> FEATURE:
<221> NAME/KEY: mutation
```

```
<222> LOCATION: (20)..(20)
<223> OTHER INFORMATION: Residue 647 Phe to Cys mutation reverse primer:
      antisense Codon gAa mutated to gCa

<400> SEQUENCE: 16
ggcctcccgg gggacgccgc acatccacgt ggcgg                                35

<210> SEQ ID NO 17
<211> LENGTH: 37
<212> TYPE: DNA
<213> ORGANISM: Thermus aquaticus
<220> FEATURE:
<221> NAME/KEY: mutation
<222> LOCATION: (19)..(20)
<223> OTHER INFORMATION: Residue 649 Val to Cys mutation forward primer:
      Codon gtc mutated to tgc

<400> SEQUENCE: 17
gccagctgga tgttcggctg cccccgggag gccgtgg                              37

<210> SEQ ID NO 18
<211> LENGTH: 37
<212> TYPE: DNA
<213> ORGANISM: Thermus aquaticus
<220> FEATURE:
<221> NAME/KEY: mutation
<222> LOCATION: (18)..(19)
<223> OTHER INFORMATION: Residue 649 Val to Cys mutation reverse primer:
      antisense Codon gAC mutated to gCA

<400> SEQUENCE: 18
ccacggcctc ccgggggcag ccgaacatcc agctggc                              37

<210> SEQ ID NO 19
<211> LENGTH: 36
<212> TYPE: DNA
<213> ORGANISM: Thermus aquaticus
<220> FEATURE:
<221> NAME/KEY: mutation
<222> LOCATION: (13)..(15)
<223> OTHER INFORMATION: Residue 652 Glu to Cys mutation forward primer:
      Codon gag mutated to tgc

<400> SEQUENCE: 19
ggcgtccccc ggtgcgccgt ggaccccctg atgcgc                               36

<210> SEQ ID NO 20
<211> LENGTH: 36
<212> TYPE: DNA
<213> ORGANISM: Thermus aquaticus
<220> FEATURE:
<221> NAME/KEY: mutation
<222> LOCATION: (22)..(24)
<223> OTHER INFORMATION: Residue 652 Glu to Cys mutation reverse primer:
      antisense Codon CTC mutated to GCA

<400> SEQUENCE: 20
gcgcatcagg gggtccacgg cgcaccgggg gacgcc                               36

<210> SEQ ID NO 21
<211> LENGTH: 36
<212> TYPE: DNA
<213> ORGANISM: Thermus aquaticus
<220> FEATURE:
<221> NAME/KEY: mutation
<222> LOCATION: (16)..(17)
<223> OTHER INFORMATION: Residue 653  Ala to Cys mutation forward
      primer:  Codon gcc mutated to tgc
```

```
<400> SEQUENCE: 21
ggcgtccccc gggagtgcgt ggaccccctg atgcgc                                 36

<210> SEQ ID NO 22
<211> LENGTH: 36
<212> TYPE: DNA
<213> ORGANISM: Thermus aquaticus
<220> FEATURE:
<221> NAME/KEY: mutation
<222> LOCATION: (20)..(21)
<223> OTHER INFORMATION: Residue 653 Ala to Cys mutation reverse
      primer:  antisense Codon gGC mutated gCA

<400> SEQUENCE: 22
gcgcatcagg gggtccacgc actcccgggg gacgcc                                 36

<210> SEQ ID NO 23
<211> LENGTH: 33
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 654 Val to Cys mutation forward
      primer:  Codon gtg mutated to tgt

<400> SEQUENCE: 23
gtcccccggg aggcctgtga cccccctgatg cgc                                   33

<210> SEQ ID NO 24
<211> LENGTH: 33
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 654 Val to Cys mutation reverse primer:
      antisense Codon CAC mutated to ACA

<400> SEQUENCE: 24
gcgcatcagg gggtcacagg cctcccgggg gac                                    33

<210> SEQ ID NO 25
<211> LENGTH: 33
<212> TYPE: DNA
<213> ORGANISM: Thermus aquaticus
<220> FEATURE:
<221> NAME/KEY: mutation
<222> LOCATION: (16)..(17)
<223> OTHER INFORMATION: Residue 655 Asp to Cys mutation forward primer:
      Codon gac mutated to tgc

<400> SEQUENCE: 25
ccccgggagg ccgtgtgccc cctgatgcgc cgg                                    33

<210> SEQ ID NO 26
<211> LENGTH: 33
<212> TYPE: DNA
<213> ORGANISM: Thermus aquaticus
<220> FEATURE:
<221> NAME/KEY: mutation
<222> LOCATION: (17)..(18)
<223> OTHER INFORMATION: Residue 655 Asp to Cys mutation reverse primer:
      antisense Codon gTC mutated to gCA

<400> SEQUENCE: 26
ccggcgcatc aggggggcaca cggcctcccg ggg                                   33
```

<210> SEQ ID NO 27
<211> LENGTH: 33
<212> TYPE: DNA
<213> ORGANISM: Thermus aquaticus
<220> FEATURE:
<221> NAME/KEY: mutation
<222> LOCATION: (16)..(17)
<223> OTHER INFORMATION: Residue 656 Pro to Cys mutation reverse primer: Codon ccc mutated to tgc

<400> SEQUENCE: 27
cgggaggccg tggactgcct gatgcgccgg gcg     33

<210> SEQ ID NO 28
<211> LENGTH: 33
<212> TYPE: DNA
<213> ORGANISM: Thermus aquaticus
<220> FEATURE:
<221> NAME/KEY: mutation
<222> LOCATION: (17)..(18)
<223> OTHER INFORMATION: Residue 656 Pro to Cys mutation reverse primer: antisense Codon gGG mutated to gCA

<400> SEQUENCE: 28
cgcccggcgc atcaggcagt ccacggcctc ccg     33

<210> SEQ ID NO 29
<211> LENGTH: 30
<212> TYPE: DNA
<213> ORGANISM: Thermus aquaticus
<220> FEATURE:
<221> NAME/KEY: mutation
<222> LOCATION: (13)..(15)
<223> OTHER INFORMATION: Residue 657 Leu to Cys mutation forward primer: Codon ctg mutated to tgc

<400> SEQUENCE: 29
gccgtggacc cctgcatgcg ccgggcggcc     30

<210> SEQ ID NO 30
<211> LENGTH: 30
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 657 Leu to Cys mutation reverse primer: antisense Codon CAG mutated to GCA

<400> SEQUENCE: 30
ggccgcccgg cgcatgcagg ggtccacggc     30

<210> SEQ ID NO 31
<211> LENGTH: 30
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 658 Met to Cys mutation forward primer: Codon atg mutated to tgc

<400> SEQUENCE: 31
gccgtggacc ccctgtgtcg ccgggcggcc     30

<210> SEQ ID NO 32
<211> LENGTH: 30
<212> TYPE: DNA

<213> ORGANISM: Thermus aquaticus
<220> FEATURE:
<221> NAME/KEY: mutation
<222> LOCATION: (13)..(15)
<223> OTHER INFORMATION: Residue 658 Met to Cys mutation reverse primer: antisense Codon CAT mutated to ACA

<400> SEQUENCE: 32
ggccgcccgg cgacacaggg ggtccacggc             30

<210> SEQ ID NO 33
<211> LENGTH: 36
<212> TYPE: DNA
<213> ORGANISM: Thermus aquaticus
<220> FEATURE:
<221> NAME/KEY: mutation
<222> LOCATION: (19)..(19)
<223> OTHER INFORMATION: Residue 659 Arg to Cys mutation forward primer: Codon cgc mutated to tgc

<400> SEQUENCE: 33
gccgtggacc ccctgatgtg ccgggcggcc aagacc             36

<210> SEQ ID NO 34
<211> LENGTH: 36
<212> TYPE: DNA
<213> ORGANISM: Thermus aquaticus
<220> FEATURE:
<221> NAME/KEY: mutation
<222> LOCATION: (18)..(18)
<223> OTHER INFORMATION: Residue 659 Arg to Cys mutation reverse primer: antisense Codon gcG mutated to gcA

<400> SEQUENCE: 34
ggtcttggcc gcccggcaca tcaggggtc cacggc             36

<210> SEQ ID NO 35
<211> LENGTH: 33
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 660 Arg to Cys mutation forward primer: Codon cgg mutated to tgc

<400> SEQUENCE: 35
gaccccctga tgcgctgcgc ggccaagacc atc             33

<210> SEQ ID NO 36
<211> LENGTH: 33
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 660 Arg to Cys mutation reverse primer: antisense Codon CcG mutated to GcA

<400> SEQUENCE: 36
gatggtcttg gccgcgcagc gcatcagggg gtc             33

<210> SEQ ID NO 37
<211> LENGTH: 33
<212> TYPE: DNA
<213> ORGANISM: Thermus aquaticus
<220> FEATURE:
<221> NAME/KEY: mutation
<222> LOCATION: (16)..(18)

```
<223> OTHER INFORMATION: Residue 661 Ala to Cys mutation forward primer:
      Codon gcg mutated to tgc

<400> SEQUENCE: 37
cccctgatgc gccggtgcgc caagaccatc aac                                   33

<210> SEQ ID NO 38
<211> LENGTH: 33
<212> TYPE: DNA
<213> ORGANISM: Thermus aquaticus
<220> FEATURE:
<221> NAME/KEY: mutation
<222> LOCATION: (16)..(18)
<223> OTHER INFORMATION: Residue 661 Ala to Cys mutation reverse primer:
      antisense Codon CGC mutated to GCA

<400> SEQUENCE: 38
gttgatggtc ttggcgcacc ggcgcatcag ggg                                   33

<210> SEQ ID NO 39
<211> LENGTH: 19
<212> TYPE: PRT
<213> ORGANISM: Thermus aquaticus
<220> FEATURE:
<221> NAME/KEY: variant
<222> LOCATION: (1)..(1)
<223> OTHER INFORMATION: Taq Pol I Residues 643 to 661; Residue 643 ala
      to cys variant

<400> SEQUENCE: 39

Cys Ser Trp Met Phe Gly Val Pro Arg Glu Ala Val Asp Pro Leu Met
1               5                   10                  15

Arg Arg Ala

<210> SEQ ID NO 40
<211> LENGTH: 19
<212> TYPE: PRT
<213> ORGANISM: Thermus aquaticus
<220> FEATURE:
<221> NAME/KEY: variant
<222> LOCATION: (5)..(5)
<223> OTHER INFORMATION: Taq Pol I Residues 643 to 661; Residue 647 phe
      to cys variant

<400> SEQUENCE: 40

Ala Ser Trp Met Cys Gly Val Pro Arg Glu Ala Val Asp Pro Leu Met
1               5                   10                  15

Arg Arg Ala

<210> SEQ ID NO 41
<211> LENGTH: 19
<212> TYPE: PRT
<213> ORGANISM: Thermus aquaticus
<220> FEATURE:
<221> NAME/KEY: variant
<222> LOCATION: (7)..(7)
<223> OTHER INFORMATION: Taq Pol I Residues 643 to 661; Residue 649 val
      to cys variant

<400> SEQUENCE: 41

Ala Ser Trp Met Phe Gly Cys Pro Arg Glu Ala Val Asp Pro Leu Met
1               5                   10                  15

Arg Arg Ala

<210> SEQ ID NO 42
<211> LENGTH: 19
```

```
<212> TYPE: PRT
<213> ORGANISM: Thermus aquaticus
<220> FEATURE:
<221> NAME/KEY: variant
<222> LOCATION: (10)..(10)
<223> OTHER INFORMATION: Taq Pol I Residues 643 to 661; Residue 652 glu
      to cys variant

<400> SEQUENCE: 42

Ala Ser Trp Met Phe Gly Val Pro Arg Cys Ala Val Asp Pro Leu Met
1               5                   10                  15

Arg Arg Ala

<210> SEQ ID NO 43
<211> LENGTH: 19
<212> TYPE: PRT
<213> ORGANISM: Thermus aquaticus
<220> FEATURE:
<221> NAME/KEY: variant
<222> LOCATION: (11)..(11)
<223> OTHER INFORMATION: Taq Pol I Residues 643 to 661; Residue 653 ala
      to cys variant

<400> SEQUENCE: 43

Ala Ser Trp Met Phe Gly Val Pro Arg Glu Cys Val Asp Pro Leu Met
1               5                   10                  15

Arg Arg Ala

<210> SEQ ID NO 44
<211> LENGTH: 19
<212> TYPE: PRT
<213> ORGANISM: Thermus aquaticus
<220> FEATURE:
<221> NAME/KEY: variant
<222> LOCATION: (12)..(12)
<223> OTHER INFORMATION: Taq Pol I Residues 643 to 661; Residue 654 val
      to cys variant

<400> SEQUENCE: 44

Ala Ser Trp Met Phe Gly Val Pro Arg Glu Ala Cys Asp Pro Leu Met
1               5                   10                  15

Arg Arg Ala

<210> SEQ ID NO 45
<211> LENGTH: 19
<212> TYPE: PRT
<213> ORGANISM: Thermus aquaticus
<220> FEATURE:
<221> NAME/KEY: variant
<222> LOCATION: (13)..(13)
<223> OTHER INFORMATION: Taq Pol I Residues 643 to 661; Residue 655 asp
      to cys variant

<400> SEQUENCE: 45

Ala Ser Trp Met Phe Gly Val Pro Arg Glu Ala Val Cys Pro Leu Met
1               5                   10                  15

Arg Arg Ala

<210> SEQ ID NO 46
<211> LENGTH: 19
<212> TYPE: PRT
<213> ORGANISM: Thermus aquaticus
<220> FEATURE:
<221> NAME/KEY: variant
<222> LOCATION: (14)..(14)
<223> OTHER INFORMATION: Taq Pol I Residues 643 to 661; Residue 656 pro
      to cys variant
```

```
<400> SEQUENCE: 46

Ala Ser Trp Met Phe Gly Val Pro Arg Glu Ala Val Asp Cys Leu Met
1               5                   10                  15

Arg Arg Ala

<210> SEQ ID NO 47
<211> LENGTH: 19
<212> TYPE: PRT
<213> ORGANISM: Thermus aquaticus
<220> FEATURE:
<221> NAME/KEY: variant
<222> LOCATION: (15)..(15)
<223> OTHER INFORMATION: Taq Pol I Residues 643 to 661; Residue 657 leu
      to cys variant

<400> SEQUENCE: 47

Ala Ser Trp Met Phe Gly Val Pro Arg Glu Ala Val Asp Pro Cys Met
1               5                   10                  15

Arg Arg Ala

<210> SEQ ID NO 48
<211> LENGTH: 19
<212> TYPE: PRT
<213> ORGANISM: Thermus aquaticus
<220> FEATURE:
<221> NAME/KEY: variant
<222> LOCATION: (16)..(16)
<223> OTHER INFORMATION: Taq Pol I Residues 643 to 661; Residue 658 met
      to cys variant

<400> SEQUENCE: 48

Ala Ser Trp Met Phe Gly Val Pro Arg Glu Ala Val Asp Pro Leu Cys
1               5                   10                  15

Arg Arg Ala

<210> SEQ ID NO 49
<211> LENGTH: 19
<212> TYPE: PRT
<213> ORGANISM: Thermus aquaticus
<220> FEATURE:
<221> NAME/KEY: variant
<222> LOCATION: (17)..(17)
<223> OTHER INFORMATION: Taq Pol I Residues 643 to 661; Residue 659 arg
      to cys variant

<400> SEQUENCE: 49

Ala Ser Trp Met Phe Gly Val Pro Arg Glu Ala Val Asp Pro Leu Met
1               5                   10                  15

Cys Arg Ala

<210> SEQ ID NO 50
<211> LENGTH: 19
<212> TYPE: PRT
<213> ORGANISM: Thermus aquaticus
<220> FEATURE:
<221> NAME/KEY: variant
<222> LOCATION: (18)..(18)
<223> OTHER INFORMATION: Taq Pol I Residues 643 to 661; Residue 660 arg
      to cys variant

<400> SEQUENCE: 50

Ala Ser Trp Met Phe Gly Val Pro Arg Glu Ala Val Asp Pro Leu Met
1               5                   10                  15

Arg Cys Ala
```

<210> SEQ ID NO 51
<211> LENGTH: 19
<212> TYPE: PRT
<213> ORGANISM: Thermus aquaticus
<220> FEATURE:
<221> NAME/KEY: variant
<222> LOCATION: (19)..(19)
<223> OTHER INFORMATION: Taq Pol I Residues 643 to 661; Residue 661 ala
      to cys variant

<400> SEQUENCE: 51

Ala Ser Trp Met Phe Gly Val Pro Arg Glu Ala Val Asp Pro Leu Met
1               5                   10                  15

Arg Arg Cys

<210> SEQ ID NO 52
<211> LENGTH: 6
<212> TYPE: PRT
<213> ORGANISM: Thermus aquaticus
<220> FEATURE:
<221> NAME/KEY: variant
<222> LOCATION: (1)..(1)
<223> OTHER INFORMATION: Taq Pol I Residues 513 to 518; Residue 513 ser
      to cys variant

<400> SEQUENCE: 52

Cys Thr Ser Ala Ala Val
1               5

<210> SEQ ID NO 53
<211> LENGTH: 6
<212> TYPE: PRT
<213> ORGANISM: Thermus aquaticus
<220> FEATURE:
<221> NAME/KEY: variant
<222> LOCATION: (2)..(2)
<223> OTHER INFORMATION: Taq Pol I Residues 513 to 518; Residue 514 thr
      to cys variant

<400> SEQUENCE: 53

Ser Cys Ser Ala Ala Val
1               5

<210> SEQ ID NO 54
<211> LENGTH: 6
<212> TYPE: PRT
<213> ORGANISM: Thermus aquaticus
<220> FEATURE:
<221> NAME/KEY: variant
<222> LOCATION: (3)..(3)
<223> OTHER INFORMATION: Taq Pol I Residues 513 to 518; Residue 515 ser
      to cys variant

<400> SEQUENCE: 54

Ser Thr Cys Ala Ala Val
1               5

<210> SEQ ID NO 55
<211> LENGTH: 6
<212> TYPE: PRT
<213> ORGANISM: Thermus aquaticus
<220> FEATURE:
<221> NAME/KEY: variant
<222> LOCATION: (4)..(4)
<223> OTHER INFORMATION: Taq Pol I Residues 513 to 518; Residue 515 ala
      to cys variant

```
-continued

<400> SEQUENCE: 55

Ser Thr Ser Cys Ala Val
1               5

<210> SEQ ID NO 56
<211> LENGTH: 6
<212> TYPE: PRT
<213> ORGANISM: Thermus aquaticus
<220> FEATURE:
<221> NAME/KEY: variant
<222> LOCATION: (5)..(5)
<223> OTHER INFORMATION: Taq Pol I Residues 513 to 518; Residue 517 ala
      to cys variant

<400> SEQUENCE: 56

Ser Thr Ser Ala Cys Val
1               5

<210> SEQ ID NO 57
<211> LENGTH: 6
<212> TYPE: PRT
<213> ORGANISM: Thermus aquaticus
<220> FEATURE:
<221> NAME/KEY: variant
<222> LOCATION: (6)..(6)
<223> OTHER INFORMATION: Taq Pol I Residues 513 to 518; Residue 518 val
      to cys variant

<400> SEQUENCE: 57

Ser Thr Ser Ala Ala Cys
1               5
```

METHODS FOR REAL-TIME SINGLE MOLECULE SEQUENCE DETERMINATION

RELATED APPLICATION

This application is a divisional of U.S. patent application Ser. No. 09/901,782 filed 9 Jul. 2001, which claim provisional priority to U.S. Provisional Patent Application Ser. No. 60/216,594, filed 7 Jul. 2000, all of which are incorporated herein by reference.

BACKGROUND OF THE INVENTION

1. Field of the Invention

The present invention relates to a single-molecule sequencing apparatus and methods.

More particularly, the present invention relates to a single-molecule sequencing apparatus and methods using tagged polymerizing agents and/or tagged monomers where the tagged polymerizing agent and/or the tagged monomers undergo a change in a detectable property before, during and/or after monomer insertion into a growing polymer chain. The apparatus and methods are ideally-suited for sequencing DNA, RNA, polypeptide, carbohydrate or similar bio-molecular sequences under near real-time or real-time conditions. The present invention also relates to a single-molecule sequencing apparatus and methods using tagged depolymerizing agents and/or tagged depolymerizable polymer where the tagged depolymerizing agent and/or the tagged depolymerizable polymer undergo a change in a detectable property before, during and/or after monomer removal from the depolymerizable polymer chain. The apparatus and methods are ideally-suited for sequencing DNA, RNA, polypeptide, carbohydrate or similar bio-molecular sequences. The present invention also relates to detecting a signal evidencing interactions between the tagged polymerizing agent or depolymerizing agent and a tagged or untagged polymer subunit such as a monomer or collection of monomers, where the detected signal provides information about monomer order. In a preferred embodiment, the methods are carried out in real-time or near real-time.

2. Description of the Related Art

Overview of Conventional DNA Sequencing

The development of methods that allow one to quickly and reliably determine the order of bases or 'sequence' in a fragment of DNA is a key technical advance, the importance of which cannot be overstated. Knowledge of DNA sequence enables a greater understanding of the molecular basis of life. DNA sequence information provides scientists with information critical to a wide range of biological processes. The order of bases in DNA specifies the order of bases in RNA, the molecule within the cell that directly encodes the informational content of proteins. DNA sequence information is routinely used to deduce protein sequence information. Base order dictates DNA structure and its function, and provides a molecular program that can specify normal development, manifestation of a genetic disease, or cancer.

Knowledge of DNA sequence and the ability to manipulate these sequences has accelerated development of biotechnology and led to the development of molecular techniques that provide the tools to ask and answer important scientific questions. The polymerase chain reaction (PCR), an important biotechnique that facilitates sequence-specific detection of nucleic acid, relies on sequence information. DNA sequencing methods allow scientists to determine whether a change has been introduced into the DNA, and to assay the effect of the change on the biology of the organism, regardless of the type of organism that is being studied. Ultimately, DNA sequence information may provide a way to uniquely identify individuals.

In order to understand the DNA sequencing process, one must recall several facts about DNA. First, a DNA molecule is comprised of four bases, adenine (A), guanine (G), cytosine (C), and thymine (T). These bases interact with each other in very specific ways through hydrogen bonds, such that A interacts with T, and G interacts with C. These specific interactions between the bases are referred to as base-pairings. In fact, it is these base-pairings (and base stacking interactions) that stabilize double-stranded DNA. The two strands of a DNA molecule occur in an antiparallel orientation, where one strand is positioned in the 5' to 3' direction, and the other strand is positioned in the 3' to 5' direction. The terms 5' and 3' refer to the directionality of the DNA backbone, and are critical to describing the order of the bases. The convention for describing base order in a DNA sequence uses the 5' to 3' direction, and is written from left to right. Thus, if one knows the sequence of one DNA strand, the complementary sequence can be deduced.

Sanger DNA Sequencing (Enzymatic Synthesis)

Sanger sequencing is currently the most commonly used method to sequence DNA (Sanger et al., 1977). This method exploits several features of a DNA polymerase: its ability to make an exact copy of a DNA molecule, its directionality of synthesis (5' to 3'), its requirement of a DNA strand (a 'primer') from which to begin synthesis, and its requirement for a 3' OH at the end of the primer. If a 3' OH is not available, then the DNA strand cannot be extended by the polymerase. If a dideoxynucleotide (ddNTP; ddATP, ddTTP, ddGTP, ddCTP), a base analogue lacking a 3' OH, is added into an enzymatic sequencing reaction, it is incorporated into the growing strand by the polymerase. However, once the ddNTP is incorporated, the polymerase is unable to add any additional bases to the end of the strand. Importantly, ddNTPs are incorporated by the polymerase into the DNA strand using the same base incorporation rules that dictate incorporation of natural nucleotides, where A specifies incorporation of T, and G specifies incorporation of C (and vice versa).

Fluorescent DNA Sequencing

A major advance in determining DNA sequence information occurred with the introduction of automated DNA sequencing machines (Smith et al., 1986). The automated sequencer is used to separate sequencing reaction products, detect and collect (via computer) the data from the reactions, and analyze the order of the bases to automatically deduce the base sequence of a DNA fragment. Automated sequencers detect extension products containing a fluorescent tag. Sequence read lengths obtained using an automated sequencer are dependent upon a variety of parameters, but typically range between 500 to 1,000 bases (3-18 hours of data collection). At maximum capacity an automated sequencer can collect data from 96 samples in parallel.

When dye-labeled terminator chemistry is used to detect the sequencing products, base identity is determined by the color of the fluorescent tag attached to the ddNTP. After the reaction is assembled and processed through the appropriate number of cycles (3-12 hours), the extension products are prepared for loading into a single lane on an automated sequencer (unincorporated, dye-labeled ddNTPs are removed and the reaction is concentrated; 1-2 hours). An advantage of dye-terminator chemistry is that extension products are visualized only if they terminate with a dye-labeled ddNTP; prematurely terminated products are not detected. Thus, reduced background noise typically results with this chemistry.

State-of-the-art dye-terminator chemistry uses four energy transfer fluorescent dyes (Rosenblum et al., 1997). These terminators include a fluorescein donor dye (6-FAM) linked to one of four different dichlororhodamine (dRhodamine) acceptor dyes. The d-Rhodamine acceptor dyes associated with the terminators are dichloro[R110], dichloro[R6G], dichloro[TAMRA] or dichloro[ROX], for the G-, A-, T- or C-terminators, respectively. The donor dye (6-FAM) efficiently absorbs energy from the argon ion laser in the automated sequencing machine and transfers that energy to the linked acceptor dye. The linker connecting the donor and acceptor portions of the terminator is optimally spaced to achieve essentially 100% efficient energy transfer. The fluorescence signals emitted from these acceptor dyes exhibit minimal spectral overlap and are collected by an ABI PRISM 377 DNA sequencer using 10 nm virtual filters centered at 540, 570, 595 and 625 nm, for G-, A-, T- or C-terminators, respectively. Thus, energy transfer dye-labeled terminators produce brighter signals and improve spectral resolution. These improvements result in more accurate DNA sequence information.

The predominant enzyme used in automated DNA sequencing reactions is a genetically engineered form of DNA polymerase I from *Thermus aquaticus*. This enzyme, AmpliTaq DNA Polymerase, FS, was optimized to more efficiently incorporate ddNTPs and to eliminate the 3' to 5' and 5' to 3' exonuclease activities. Replacing a naturally occurring phenylalanine at position 667 in *T. aquaticus* DNA polymerase with a tyrosine reduced the preferential incorporation of a dNTP, relative to a ddNTP (Tabor and Richardson, 1995; Reeve and Fuller, 1995). Thus, a single hydroxyl group within the polymerase is responsible for discrimination between dNTPs and ddNTPs. The 3' to 5' exonuclease activity, which enables the polymerase to remove a mis-incorporated base from the newly replicated DNA strand (proofreading activity), was eliminated because it also allows the polymerase to remove an incorporated ddNTP. The 5' to 3' exonuclease activity was eliminated because it removes bases from the 5' end of the reaction products. Since the reaction products are size separated during gel electrophoresis, interpretable sequence data is only obtained if the reaction products share a common endpoint. More specifically, the primer defines the 5' end of the extension product and the incorporated, color-coded ddNTP defines base identity at the 3' end of the molecule. Thus, conventional DNA sequencing involves analysis of a population of DNA molecules sharing the same 5' endpoint, but differing in the location of the ddNTP at the 3' end of the DNA chain.

Genome Sequencing

Very often a researcher needs to determine the sequence of a DNA fragment that is larger than the 500-1,000 base average sequencing read length. Not surprisingly, strategies to accomplish this have been developed. These strategies are divided into two major classes, random or directed, and strategy choice is influenced by the size of the fragment to be sequenced.

In random or shotgun DNA sequencing, a large DNA fragment (typically one larger than 20,000 base pairs) is broken into smaller fragments that are inserted into a cloning vector. It is assumed that the sum of information contained within these smaller clones is equivalent to that contained within the original DNA fragment. Numerous smaller clones are randomly selected, DNA templates are prepared for sequencing reactions, and primers that will base-pair with the vector DNA sequence bordering the insert are used to begin the sequencing reaction (2-7 days for a 20 kbp insert). Subsequently, the quality of each base call is examined (manually or automatically via software (PHRED, Ewing et al., 1998); 1-10 minutes per sequence reaction), and the sequence of the original DNA fragment is reconstructed by computer assembly of the sequences obtained from the smaller DNA fragments. Based on the time estimates provided, if a shotgun sequencing strategy is used, a 20 kbp insert is expected to be completed in 3-10 days. This strategy was extensively used to determine the sequence of ordered fragments that represent the entire human genome (http://www.nhgri.nih.gov/HGP/). However, this random approach is typically not sufficient to complete sequence determination, since gaps in the sequence often remain after computer assembly. A directed strategy (described below) is usually used to complete the sequence project.

A directed or primer-walking sequencing strategy can be used to fill-in gaps remaining after the random phase of large-fragment sequencing, and as an efficient approach for sequencing smaller DNA fragments. This strategy uses DNA primers that anneal to the template at a single site and act as a start site for chain elongation. This approach requires knowledge of some sequence information to design the primer. The sequence obtained from the first reaction is used to design the primer for the next reaction and these steps are repeated until the complete sequence is determined. Thus, a primer-based strategy involves repeated sequencing steps from known into unknown DNA regions, the process minimizes redundancy, and it does not require additional cloning steps. However, this strategy requires the-synthesis of a new primer for each round of sequencing.

The necessity of designing and synthesizing new primers, coupled with the expense and the time required for their synthesis, has limited the routine application of primer-walking for sequencing large DNA fragments. Researchers have proposed using a library of short primers to eliminate the requirement for custom primer synthesis (Studier, 1989; Siemieniak and Slightom, 1990; Kieleczawa et al., 1992; Kotler et al., 1993; Burbelo and Iadarola, 1994; Hardin et al., 1996; Raja et al., 1997; Jones and Hardin, 1998a,b; Ball et al., 1998; Mei and Hardin, 2000; Kraltcheva and Hardin, 2001). The availability of a primer library minimizes primer waste, since each primer is used to prime multiple reactions, and allows immediate access to the next sequencing primer.

One of the original goals of the Human Genome Project was to complete sequence determination of the entire human genome by 2005 (http://www.nhgri.nih.gov/HGP/). However, the plan is ahead of schedule and a 'working draft' of the human genome was published in February 2001 (Venter et al., 2001, "International Human Genome Sequencing Consortium 2001"). Due to technological advances in several disciplines, the completed genome sequence is expected in 2003, two years ahead of schedule. Progress in all aspects involving DNA manipulation (especially manipulation and propagation of large DNA fragments), evolution of faster and better DNA sequencing methods (http://www.abrf.org), development of computer hardware and software capable of manipulating and analyzing the data (bioinformatics), and automation of procedures associated with generating and analyzing DNA sequences (engineering) are responsible for this accelerated time frame.

Single-Molecule DNA Sequencing

Conventional DNA sequencing strategies and methods are reliable, but time, labor, and cost intensive. To address these issues, some researchers are investigating fluorescence-based, single-molecule sequencing methods that use enzymatic degradation, followed by single-dNMP detection and identification. The DNA polymer containing fluorescently-labeled nucleotides is digested by an exonuclease, and the labeled nucleotides are detected and identified by flow cytometry (Davis et al., 1991; Davis et al., 1992; Goodwin et al., 1997; Keller et al., 1996; Sauer et al., 1999; Werner et al., 1999). This method requires that the DNA strand is synthesized to contain the flourescently-labeled base(s). This requirement limits the length of sequence that can be determined, and increases the number of manipulations that must be performed before any sequence data is obtained. A related approach proposes to sequentially separate single (unlabeled) nucleotides from a strand of DNA, confine them in their original order in a solid matrix, and detect the spectroscopic emission of the separated nucleotides to reconstruct DNA sequence information (Ulmer, 1997; Mitsis and Kwagh, 1999; Dapprich, 1999). This is the approach that is being developed by Praelux, Inc., a company with a goal to develop single-molecule DNA sequencing. Theoretically, this latter method should not be as susceptible to length limitations as the former enzymatic degradation method, but it does require numerous manipulations before any sequence information can be obtained.

Li-cor, Inc. is developing an enzyme synthesis based strategy for single-molecule sequencing as set forth in PCT application WO 00/36151. The Li-cor method involves multiply modifying each dNTP by attaching a fluorescent tag to the γ-phosphate and a quenching moiety to the another site on the dNTP, preferably on the base. The quenching moiety is added to prevent emission from the fluorescent tag attached to an unincorporated dNTP. Upon incorporation the fluorescent tag and quenching moiety are separated, resulting in emission from the tag. The tag (contained on the pyrophosphate) flows away from the polymerase active site, but the modified (quenched) base becomes part of the DNA polymer.

Although some single-molecular sequencing systems have been disclosed, many of them anticipate or require base modification. See, e.g., Patent Application Serial Numbers WO 01/16375 A2, WO 01/23610 A2, WO 01/25480, WO 00/06770, WO 99/05315, WO 00/60114, WO 00/36151, WO 00/36512, and WO 00/70073, incorporated herein by reference. Base modifications may distort DNA structure (which normally consists of A-form DNA nearest the enzyme active site; Li et al., 1998a). Since the dNTP and approximately 7 of the 3'-nearest bases in the newly synthesized strand contact internal regions of the polymerase (Li et al., 1998a), the A-form DNA may be important for maximizing minor groove contacts between the enzyme and the DNA. If the DNA structure is affected due to base modification, enzyme fidelity and/or function may be altered. Thus, there is still a need in the art for a fast and efficient enzymatic DNA sequencing system for single molecular DNA sequences.

SUMMARY OF THE INVENTION

Single-Molecule Sequencing

The present invention provides a polymerizing agent modified with at least one molecular or atomic tag located at or near, associated with or covalently bonded to a site on the polymerizing agent, where a detectable property of the tag undergoes a change before, during and/or after monomer incorporation. The monomers can be organic, inorganic or bio-organic monomers such as nucleotides for DNA, RNA, mixed DNA/RNA sequences, amino acids, monosaccharides, synthetic analogs of naturally occurring nucleotides, synthetic analogs of naturally occurring amino acids or synthetic analogs of naturally occurring monosaccharides, synthetic organic or inorganic monomers, or the like.

The present invention provides a depolymerizing agent modified with at least one molecular or atomic tag located at or near, associated with or covalently bonded to a site on the depolymerizing agent, where a detectable property of the tag undergoes a change before, during and/or after monomer removal. The polymers can be DNA, RNA, mixed DNA/RNA sequences containing only naturally occurring nucleotides or a mixture of naturally occurring nucleotides and synthetic analogs thereof, polypeptide sequences containing only naturally occurring amino acids or a mixture of naturally occurring amino acids and synthetic analogs thereof, polysaccharide or carbohydrate sequences containing only naturally occurring monosaccharides or a mixture of naturally occurring monosaccharides and synthetic analogs thereof, or polymers containing synthetic organic or inorganic monomers, or the like.

The present invention also provides a system that enables detecting a signal corresponding to a detectable property evidencing changes in interactions between a synthesizing/polymerizing agent or a depolymerizing agent (molecule) and its substrates (monomers or depolymerizable polymers) and decoding the signal into monomer order specific information or monomer sequence information, preferably in real-time or near real-time.

Single Site Tagged Polymerase

The present invention provides a polymerase modified with at least one molecular or atomic tag located at or near, associated with, or covalently bonded to a site on the polymerase, where a detectable property of the tag undergoes a change before, during and/or after monomer incorporation. The monomers can be nucleotides for DNA, RNA or mixed DNA/RNA monomers or synthetic analogs polymerizable by the polymerase.

The present invention provides an exonuclease modified with at least one molecular or atomic tag located at or near, associated with, or covalently bonded to a site on the exonuclease, where a detectable property of the tag undergoes a change before, during and/or after monomer release. The polymers can be DNA, RNA or mixed DNA/RNA sequences comprised of naturally occurring monomers or synthetic analogs depolymerizable by the exonuclease.

The present invention provides a polymerase modified with at least one molecular or atomic tag located at or near, associated with, or covalently bonded to a site that undergoes a conformational change before, during and/or after monomer incorporation, where the tag has a first detection propensity when the polymerase is in a first conformational state and a second detection propensity when the polymerase is in a second conformational state.

The present invention provides a polymerase modified with at least one chromophore located at or near, associated with, or covalently bonded to a site that undergoes a conformational change before, during and/or after monomer incorporation, where an intensity and/or frequency of emitted light of the chromophore has a first value when the polymerase is in a first conformational state and a second value when the polymerase is in a second conformational state.

The present invention provides a polymerase modified with at least one fluorescently active molecular tag located at or near, associated with, or covalently bonded to a site that undergoes a conformational change before, during and/or after monomer incorporation, where the tag has a first fluorescence propensity when the polymerase is in a first conformational state and a second fluorescence propensity when the polymerase is in a second conformational state.

The present invention provides a polymerase modified with a molecular tag located at or near, associated with, or covalently bonded to a site that undergoes a conformational change before, during and/or after monomer incorporation, where the tag is substantially detectable when the polymerase is in a first conformational state and substantially non-detectable when the polymerase is in a second conformational state or substantially non-detectable when the polymerase is in the first conformational state and substantially detectable when the polymerase is in the second conformational state.

The present invention provides a polymerase modified with at least one molecular or atomic tag located at or near, associated with, or covalently bonded to a site that interacts with a tag on the released pyrophosphate group, where the polymerase tag has a first detection propensity before interacting with the tag on the released pyrophosphate group and a second detection propensity when interacting with the tag on the released pyrophosphate group. In a preferred embodiment, this change in detection propensity is cyclical occurring as each pyrophosphate group is released.

The present invention provides a polymerase modified with at least one chromophore located at or near, associated with, or covalently bonded to a site that interacts with a tag on the released pyrophosphate group, where an intensity and/or frequency of light emitted by the chromophore has a first value before the chromophore interacts with the tag on the released pyrophosphate and a second value when interacting with the tag on the released pyrophosphate group. In a preferred embodiment, this change in detection propensity is cyclical occurring as each pyrophosphate group is released.

The present invention provides a polymerase modified with at least one fluorescently active molecular tag located at or near, associated with, or covalently bonded to a site that interacts with a tag on the released pyrophosphate group, where the polymerase tag changes from a first state prior to release of the pyrophosphate group and a second state as the pyrophosphate group diffuses away from the site of release. In a preferred embodiment, this change in detection propensity is cyclical occurring as each pyrophosphate group is released.

The present invention provides a polymerase modified with a molecular tag located at or near, associated with, or covalently bonded to a site that interacts with a tag on the released pyrophosphate group, where the polymerase tag changes from a substantially detectable state prior to pyrophosphate release to a substantially non-detectable state when the polymerase tag interacts with the tag on the pyrophosphate group after group release, or changes from a substantially non-detectable state prior to pyrophosphate release to a substantially detectable state when the polymerase tag interacts with the tag on the pyrophosphate group after group release.

Multiple Site Tagged Polymerizing or Depolymerizing Agents

The present invention provides a monomer polymerizing agent modified with at least one pair of molecular and/or atomic tags located at or near, associated with, or covalently bonded to sites on the polymerizing agent, where a detectable property of at least one tag of the pair undergoes a change before, during and/or after monomer incorporation or where a detectable property of at least one tag of the pair undergoes a change before, during and/or after monomer incorporation due to a change in inter-tag interaction.

The present invention provides a depolymerizing agent modified with at least one pair of molecular and/or atomic tags located at or near, associated with, or covalently bonded to sites on the depolymerizing agent, where a detectable property of at least one tag of the pair undergoes a change before, during and/or after monomer release or where a detectable property of at least one tag of the pair undergoes a change before, during and/or after monomer release due to a change in inter-tag interaction.

The present invention provides a monomer polymerizing agent modified with at least one pair of molecular and/or atomic tags located at or near, associated with, or covalently bonded to sites on the polymerizing agent, where a detectable property of at least one tag of the pair has a first value when the polymerizing agent is in a first state and a second value when the polymerizing agent is in a second state, where the polymerizing agent changes from the first state to the second state and back to the first state during a monomer incorporation cycle.

The present invention provides a depolymerizing agent modified with at least one pair of molecular and/or atomic tags located at or near, associated with or covalently bonded to sites on the polymerizing agent, where a detectable property of at least one tag of the pair has a first value when the depolymerizing agent is in a first state and a second value when the depolymerizing agent is in a second state, where the depolymerizing agent changes from the first state to the second state and back to the first state during a monomer release cycle.

Preferably, the first and second states are different so that a change in the detected signal occurs. However, a no-change result may evidence other properties of the polymerizing media or depolymerizing media.

Multiple Site Tagged Polymerase

The present invention provides a polymerase modified with at least one pair of molecular tags located at or near, associated with, or covalently bonded to sites at least one of the tags undergoes a change during monomer incorporation, where a detectable property of the pair has a first value when the polymerase is in a first state and a second value when the polymerase is in a second state, where the polymerase changes from the first state to the second state and back to the first state during a monomer incorporation cycle.

The present invention provides a polymerase modified with at least one pair of molecular tags located at or near, associated with or covalently bonded to sites at least one of the tags undergoes conformational change during monomer incorporation, where the detectably property of the pair has a first value when the polymerase is in a first conformational state and a second value when the polymerase is in a second conformational state, where the polymerase changes from the first state to the second state and back to the first state during a monomer incorporation cycle.

The present invention provides a polymerase modified with at least one pair of molecules or atoms located at or near, associated with or covalently bonded to sites at least one of the tags undergoes conformational change during monomer incorporation, where the pair interact to form a chromophore when the polymerase is in a first conformational state or a second conformational state, where the polymerase changes from the first state to the second state and back to the first state during a monomer incorporation cycle.

The present invention provides a polymerase modified with at least one pair of molecular tags located at or near, associated with or covalently bonded to sites at least one of the tags undergoes conformational change during monomer incorporation, where the tags have a first fluorescence propensity when the polymerase is in a first conformational state and a second fluorescence propensity when the polymerase is in a second conformational state, where the polymerase changes from the first state to the second state and back to the first state during a monomer incorporation cycle.

The present invention provides a polymerase modified with at least one pair of molecular tags located at or near, associated with or covalently bonded to sites at least one of the tags undergoes conformational change during monomer incorporation, where the pair is substantially active when the polymerase is in a first conformational state and substantially inactive when the polymerase is in a second conformational state or substantially inactive when the polymerase is in the first conformational state and substantially active when the polymerase is in the second conformational state, where the polymerase changes from the first state to the second state and back to the first state during a monomer incorporation cycle.

The present invention provides a polymerase modified with at least one pair of molecular tags located at or near, associated with, or covalently bonded to sites at least one of the tags undergoes a change during and/or after pyrophosphate release during the monomer incorporation process, where a detectable property of the pair has a first value when the tag is in a first state prior to pyrophosphate release and a second value when the tag is in a second state during and/or after pyrophosphate release, where the tag changes from its first state to its second state and back to its first state during a monomer incorporation cycle.

The present invention provides a polymerase modified with at least one pair of molecular tags located at or near, associated with or covalently bonded to sites at least one of the tags undergoes a change in position due to a conformational change in the polymerase during the pyrophosphate release process, where the detectably property of the pair has a first value when the tag is in its first position and a second value when the tag is in its second position, where the tag changes from its first position to its second position and back to its first position during a release cycle.

The present invention provides a polymerase modified with at least one pair of molecules or atoms located at or near, associated with or covalently bonded to sites, where the tags change relative separation due to a conformational change in the polymerase during pyrophosphate release, where the tags interact to form a chromophore having a first emission profile when the tags are a first distance apart and a second profile when the tags are a second distance apart, where the separation distance changes from its first state to its second state and back to its first state during a pyrophosphate release cycle.

The present invention provides a polymerase modified with at least one pair of molecular tags located at or near, associated with or covalently bonded to sites, where the tags change relative separation due to a conformational change in the polymerase during pyrophosphate release, where the tags have a first fluorescence propensity when the polymerase is in a first conformational state and a second fluorescence propensity when the polymerase is in a second conformational state, where the propensity changes from its the first value to its second value and back again during a pyrophosphate release cycle.

The present invention provides a polymerase modified with at least one pair of molecular tags located at or near, associated with or covalently bonded to sites, where the tags change relative separation due to a conformational change in the polymerase during pyrophosphate release, where the pair is substantially fluorescently active when the tags have a first separation and substantially fluorescently inactive when the tags have a second separation or substantially fluorescently inactive when the tags have the first separation and substantially fluorescently active when the tags have the second separation, where the fluorescence activity undergoes one cycle during a pyrophosphate release cycle.

It should be recognized that when a property changes from a first state to a second state and back again, then the property undergoes a cycle. Preferably, the first and second states are different so that a change in the detected signal occurs. However, a no-change result may evidence other properties of the polymerizing medium or depolymerizing medium.

Methods Using Tagged Polymerizing Agent

The present invention provides a method for determining when a monomer is incorporated into a growing molecular chain comprising the steps of monitoring a detectable property of an atomic or molecular tag, where the tag is located at or near, associated with, or covalently bonded to a site on a polymerizing agent, where the detectable property of the tag undergoes a change before, during and/or after monomer incorporation.

The present invention provides a method for determining when a monomer is incorporated into a growing molecular chain comprising the steps of monitoring a detectable property of an atomic or molecular tag, where the tag is located at or near, associated with, or covalently bonded to a site on a polymerizing agent, where the detectable property has a first value when the agent is in a first state and a second value when the agent is in a second state, where the agent changes from the first state to the second state and back to the first state during a monomer incorporation cycle.

Preferably, the first and second states are different so that a change in the detected signal occurs. However, a no-change result may evidence other properties of the polymerizing medium.

Methods Using Tagged Polymerase

The present invention provides a method for determining when or whether a monomer is incorporated into a growing molecular chain comprising the steps of monitoring a detectable property of a tag, where the tag is located at or near, associated with, or covalently bonded to a site on a polymerase, where the site undergoes a change during monomer incorporation and where the detectable property has a first value when the polymerase is in a first state and a second value when the polymerase is in a second state, where the values signify that the site has undergone the change and where the polymerase changes from the first state to the second state and back to the first state during a monomer incorporation cycle.

The present invention provides a method for determining when or whether a monomer is incorporated into a growing molecular chain comprising the steps of monitoring a detectable property of a tag, where the tag is located at or near, associated with, or covalently bonded to a site on a polymerase, where the site undergoes a conformational change during monomer incorporation and where the detectable property has a first value when the polymerase is in a first conformational state and a second value when the polymerase is in a second conformational state, where the values signify that the site has undergone the change and where the polymerase changes from the first state to the second state and back to the first state during a monomer incorporation cycle.

The present invention provides a method for determining when or whether a monomer is incorporated into a growing molecular chain comprising the steps of exposing a tagged polymerase to light, monitoring an intensity and/or frequency of fluorescent light emitted by the tagged polymerase, where the tagged polymerase comprises a polymerase including a tag located at or near, associated with, or covalently bonded to a site that undergoes conformational change during monomer incorporation and where the tag emits fluorescent light at a first intensity and/or frequency when the polymerase is in a first conformational state and a second intensity and/or frequency when the polymerase is in a second conformational state, where the change in intensities and/or frequencies signifies that the site has undergone the change and where the polymerase changes from the first state to the second state and back to the first state during a monomer incorporation cycle.

The present invention also provides the above methods using a plurality of tagged polymerases permitting parallel and/or massively parallel sequencing simultaneously. Such parallelism can be used to ensure confidence. Such parallelism can also be used to quickly detect the degree of homology in DNA sequences for a given gene across species or to quickly screen patient DNA for specific genetic traits or to quickly screen DNA sequences for polymorphisms.

The present invention also provides a method for determining if or when a monomer is incorporated into a growing DNA chain associated with a polymerase, where a tag is located on the polymerase so that as the pyrophosphate group is released after base incorporation and prior to its diffusion away from the polymerase, the polymerase tag interacts with the tag on the pyrophosphate causing a change in a detectable property of one of the tags or a detectable property associated with both tags in the case of a fluorescent pair.

Preferably, the first and second states are different so that a change in the detected signal occurs. However, a nochange result may evidence other properties of the polymerizing media.

Apparatuses Using Tagged Polymerizing Agent

The present invention provides a single-molecule sequencing apparatus comprising a substrate having deposited thereon at least one tagged polymerizing agent. The tagged polymerizing agent can be placed on the surface of the substrate in an appropriate polymerizing medium or the polymerizing agent can be confined in a region, area, well, groove, channel or other similar structure on the substrate. The substrate can also include a monomer region, area, well, groove, channel, reservoir or other similar structure on the substrate connected to the polymerizing agent confinement structure by at least one connecting structure capable of supporting molecular transport of monomer to the polymerizing agent such as a channel, groove, or the like. Alternatively, the substrate can include structures containing each monomer, where each structure is connected to the polymerizing agent confinement structure by a connecting structure capable of supporting molecular transport of monomer to the polymerizing agent. The substrate can also be subdivided into a plurality of polymerizing agent confinement structures, where each structure is connected to a monomer reservoir. Alternatively, each polymerizing agent confinement structure can have its own monomer reservoir or sufficient monomer reservoirs so that each reservoir contains a specific monomer.

The present invention also provides a single-molecule sequencing apparatus comprising a substrate having at least one tagged polymerizing agent attached to the surface of the substrate by a molecular tether or linking group, where one end of the tether or linking group is bonded to a site on the surface of the substrate and the other end is bonded to a site on the polymerizing agent or bonded to a site on a molecule strongly associated with the polymerizing agent. In this context, the term "bonded to" means that chemical and/or physical interactions sufficient to maintain the polymerizing agent within a given region of the substrate under normal polymerizing conditions. The chemical and/or physical interactions include, without limitation, covalent bonding, ionic bonding, hydrogen bonding, apolar bonding, attractive electrostatic interactions, dipole interactions, or any other electrical or quantum mechanical interaction sufficient in toto to maintain the polymerizing agent in a desired region of the substrate. The substrate having tethered tagged polymerizing agent attached thereon can be placed in container containing an appropriate polymerizing medium. Alternatively, the tagged polymerizing agent can be tethered or anchored on or within a region, area, well, groove, channel or other similar structure on the substrate capable of being filled with an appropriate polymerizing medium. The substrate can also include a monomer region, area, well, groove, channel or other similar structure on the substrate connected to the polymerizing agent structure by at least one a connecting structure capable of supporting molecular transports of monomer to the polymerizing agent. Alternatively, the substrate can include structures containing each monomer, where each structure is connected to the polymerizing agent structure by a connecting structure capable of supporting molecular transports of monomer to the polymerizing agent. The substrate can also be subdivided into a plurality of polymerizing agent structures each having at least one tethered polymerizing agent, where each structure is connected to a monomer reservoir. Alternatively, each polymerizing agent structure can have its own monomer reservoir or sufficient monomer reservoirs, one reservoir of each specific monomer.

The monomers for use in these apparatus including, without limitation, dNTPs, tagged dNTPs, ddNTPs, tagged ddNTPs, amino acids, tagged amino acids, mono saccharides, tagged monosaccharides or appropriate mixtures or combinations thereof depending on the type of polymer being sequenced.

Apparatus Using Tagged Polymerase

The present invention provides a single-molecule sequencing apparatus comprising a substrate having deposited thereon at least one tagged polymerase. The tagged polymerase can be placed on the surface of the substrate in an appropriate polymerizing medium or the polymerase can be confined in a region, area, well, groove, channel or other similar structure on the substrate capable of being filled with an appropriate polymerizing medium. The substrate can also include a monomer region, area, well, groove, channel or other similar structure on the substrate connected to the polymerase confinement structure by at least one connecting structure capable of supporting molecular transports of monomer to the polymerase. Alternatively, the substrate can include structures containing each monomer, where each structure is connected to the polymerase confinement structure by a connecting structure capable of supporting molecular transports of the monomer to the polymerase in the polymerase confinement structures. The substrate can also be subdivided into a plurality of polymerase confinement structures, where each structure is connected to a monomer reservoir. Alternatively, each polymerase confinement structure can have its own monomer reservoir or four reservoirs, each reservoir containing a specific monomer.

The present invention also provides a single-molecule sequencing apparatus comprising a substrate having at least one tagged polymerase attached to the surface of the substrate by a molecular tether or linking group, where one end of the tether or linking group is bonded to a site on the surface of the substrate and the other end is bonded (either directly or indirectly) to a site on the polymerase or bonded to a site on a molecule strongly associated with the polymerase. In this context, the term "bonded to" means that chemical and/or physical interactions sufficient to maintain the polymerase within a given region of the substrate under normal polymerizing conditions. The chemical and/or physical interactions include, without limitation, covalent bonding, ionic bonding, hydrogen bonding, apolar bonding, attractive electrostatic interactions, dipole interactions, or any other electrical or quantum mechanical interaction sufficient in toto to maintain the polymerase in its desired region. The substrate having tethered tagged polymerizing agent attached thereon can be placed in container containing an appropriate polymerizing medium. Alternatively, the tagged polymerizing agent can be tethered or anchored on or within a region, area, well, groove, channel or other similar structure on the substrate capable of being filled with an appropriate polymerizing medium. The substrate can also include a monomer region, area, well, groove, channel or other similar structure on the substrate connected to the polymerase structure by at least one channel. Alternatively, the substrate can include structures containing each monomer, where each structure is connected to the polymerase structure by a connecting structure that supports molecular transports of the monomer to the polymerase in the polymerase confinement structures. The substrate can also be subdivided into a plurality of polymerase structures each having at least one tethered polymerase, where each structure is connected to a monomer reservoir. Alternatively, each polymerase structure can have its own monomer reservoir or four reservoirs, each reservoir containing a specific monomer.

The monomers for use in these apparatus including, without limitation, dNTPs, tagged dNTPs, ddNTPs, tagged ddNTPs, or mixtures or combinations thereof.

Methods Using the Single-Molecule Sequencing Apparatuses

The present invention provides a method for single-molecule sequencing comprising the step of supplying a plurality of monomers to a tagged polymerizing agent confined on or tethered to a substrate and monitoring a detectable property of the tag over time. The method can also include a step of relating changes in the detectable property to the occurrence (timing) of monomer addition and/or to the identity of each incorporated monomer and/or to the near simultaneous determination of the sequence of incorporated monomers.

The present invention provides a method for single-molecule sequencing comprising the step of supplying a plurality of monomers to a tagged polymerizing agent confined on or tethered to a substrate, exposing the tagged polymerizing agent to light either continuously or periodically and measuring an intensity and/or frequency of fluorescent light emitted by the tag over time. The method can further comprise relating the changes in the measured intensity and/or frequency of emitted fluorescent light from the tag over time to the occurrence (timing) of monomer addition and/or to the identity of each incorporated monomer and/or to the near simultaneous determination of the sequence of the incorporated monomers.

The present invention provides a method for single-molecule sequencing comprising the step of supplying a plurality of monomers to a tagged polymerase confined on or tethered to a substrate and monitoring a detectable property of the tag over time. The method can also include a step of relating changes in the detectable property over time to the occurrence (timing) of monomer addition and/or to the identity of each incorporated monomer and/or to the near simultaneous determination of the sequence of the incorporated monomers.

The present invention provides a method for single-molecule sequencing comprising the step of supplying a plurality of monomers to a tagged polymerase confined on a substrate, exposing the tagged polymerase to light continuously or periodically and measuring an intensity and/or frequency of fluorescent light emitted by the tagged polymerase over time. The method can further comprise relating changes in the measured intensity and/or frequency of emitted fluorescent light from the tag over time to the occurrence (timing) of monomer addition and/or to the identity of each incorporated monomer and/or to the near simultaneous determination of the sequence of the incorporated monomers.

Cooperatively Tagged Systems

The present invention provides cooperatively tagged polymerizing agents and tagged monomers, where a detectable property of at least one of the tags changes when the tags interact before, during and/or after monomer insertion. In one preferred embodiment, the tag on the polymerase is positioned such that the tags interact before, during and/or after each monomer insertion. In the of case tags that are released from the monomers after monomer insert such as of $\beta$ and/or $\gamma$ phosphate tagged dNTPs, i.e., the tags reside on the $\beta$ and/or $\gamma$ phosphate groups, the tag on the polymerizing agent can be designed to interact with the tag on the monomer only after the tag is released from the polymerizing agent after monomer insertion. Tag placement within a polymerizing agent can be optimized to enhance interaction between the polymerase and dNTP tags by attaching the polymerase tag to sites on the polymerase that move during an incorporation event changing the relative separation of the two tags or optimized to enhance interaction between the polymerase tag and the tag on the pyrophosphate as it is release during base incorporation and prior to its diffusion away from the polymerizing agent.

The present invention provides cooperatively tagged polymerizing agents and tagged monomers, where a detectable property of at least one of the tags changes when the tags are within a distance sufficient to cause a measurable change in the detectable property. If the detectable property is fluorescence induced in one tag by energy transfer to the other tag or due to one tag quenching the fluorescence of the other tag or causing a measurable change in the fluorescence intensity and/or frequency, the measurable change is caused by bringing the tags into close proximity to each other, i.e., decrease the distance separating the tags. Generally, the distance needed to cause a measurable change in the detectable property is within (less than or equal to) about 100 Å, preferably within about 50 Å, particularly within about 25 Å, especially within about 15 Å and most preferably within about 10 Å. Of course, one skilled in the art will recognize that a distance sufficient to cause a measurable change in a detectable property of a tag will depend on many parameters including the location of the tag, the nature of the tag, the solvent system, external fields, excitation source intensity and frequency band width, temperature, pressure, etc.

The present invention provides a tagged polymerizing agent and tagged monomer precursor(s), where an intensity and/or frequency of fluorescence light emitted by at least one tag changes when the tags interact before, during and/or after monomer insertion.

The present invention provides cooperatively tagged depolymerizing agents and tagged depolymerizable polymer, where a detectable property of at least one of the tags changes when the tags interact before, during and/or after monomer release. The tag on the depolymerizing agent can be designed so that the tags interact before, during and/or after each monomer release.

The present invention provides cooperatively tagged depolymerizing agents and tagged polymers, where a detectable property of at least one of the tags changes when the tags are within a distance sufficient to cause a change in measurable change in the detectable property. If the detectable property is fluorescence induced in one tag by energy transfer to the other tag or due to one tag quenching the fluorescence of the other tag or causing a measurable change in the fluorescence intensity and/or frequency, the measurable change is caused by bringing to tags into close proximity to each other, i.e., decrease the distance separating the tags. Generally, the distance needed to cause a measurable change in the detectable property is within (less than or equal to) about 100 Å, preferably within about 50 Å, particularly within about 25 Å, especially within about 15 Å and most preferably within about 10 Å. Of course, one skilled in the art will recognize that a distance sufficient to cause a measurable change in a detectable property of a tag will depend on many parameters including the location of the tag, the nature of the tag, the solvent system, external fields, excitation source intensity and frequency band width, temperature, pressure, etc.

The present invention provides a tagged depolymerizing agents and a tagged polymer, where an intensity and/or frequency of fluorescence light emitted by at least one tag changes when the tags interact before, during and/or after monomer release.

Cooperatively Tagged Systems Using a Polymerase

The present invention provides cooperatively tagged polymerase and tagged monomers, where a detectable property of at least one of the tags changes when the tags interact before, during and/or after monomer insertion. The tag on the polymerase can be designed so that the tags interact before, during and/or after each monomer insertion. In the of case tags that are released from the monomers after monomer insert such as of β and/or γ phosphate tagged dNTPs, i.e., the tags reside on the β and/or γ phosphate groups, the tag on the polymerizing agent can be designed to interact with the tag on the monomer only after the tag is released from the polymerizing agent after monomer insertion. In the first case, the polymerase tag must be located on a site of the polymerase which allows the polymerase tag to interact with the monomer tag during the monomer insertion process—initial binding and bonding into the growing polymer. While in the second case, the polymerase tag must be located on a site of the polymerase which allows the polymerase tag to interact with the monomer tag now on the released pyrophosphate prior to its diffusion away from the polymerase and into the polymerizing medium.

The present invention provides cooperatively tagged polymerase and tagged monomers, where a detectable property of at least one of the tags changes when the tags are within a distance sufficient or in close proximity to cause a measurable change in the detectable property. If the detectable property is fluorescence induced in one tag by energy transfer to the other tag or due to one tag quenching the fluorescence of the other tag or causing a measurable change in the fluorescence intensity and/or frequency, the measurable change is caused by bringing to tags into close proximity to each other, i.e., decrease the distance separating the tags. Generally, the distance or close proximity is a distance between about 100 Å and about 10 Å. Alternatively, the distance is less than or equal to about 100 Å, preferably less than or equal to about 50 Å, particularly less than or equal to about 25 Å, especially less than or equal to about 15 Å and most preferably less than or equal to about 10 Å. Of course, one skilled in the art will recognize that a distance sufficient to cause a measurable change in a detectable property of a tag will depend on many parameters including the location of the tags, the nature of the tags, the solvent system (polymerizing medium), external fields, excitation source intensity and frequency band width, temperature, pressure, etc.

The present invention provides a tagged polymerase and tagged monomer precursors, where the tags form a fluorescently active pair such as a donor-acceptor pair and an intensity and/or frequency of fluorescence light emitted by at least one tag (generally the acceptor tag in donor-acceptor pairs) changes when the tags interact.

The present invention provides a tagged polymerase and a tagged monomer precursors, where the tags form a fluorescently active pair such as a donor-acceptor pair and an intensity and/or frequency of fluorescence light emitted by at least one tag (generally the acceptor tag in donor-acceptor pairs) changes when the tags are a distance sufficient or in close proximity to change either the intensity and/or frequency of the fluorescent light. Generally, the distance or close proximity is a distance between about 100 Å and about 10 Å. Alternatively, the distance is less than or equal to about 100 Å, preferably less than or equal to about 50 Å, particularly less than or equal to about 25 Å, especially less than or equal to about 15 Å and most preferably less than or equal to about 10 Å. Of course, one skilled in the art will recognize that a distance sufficient to cause a measurable change in a detectable property of a tag will depend on many parameters including the location of the tag, the nature of the tag, the solvent system, external fields, excitation source intensity and frequency band width, temperature, pressure, etc.

The present invention provides a single-molecule sequencing apparatus comprising a container having at least one tagged polymerase confined on or tethered to an interior surface thereof and having a solution containing a plurality of tagged monomers in contact with the interior surface.

Molecular Data Stream Reading Methods and Apparatus

The present invention provides a method for single-molecule sequencing comprising the step of supplying a plurality of tagged monomers to a tagged polymerase confined on an interior surface of a container, exposing the tagged polymerase to light and measuring an intensity and/or frequency of fluorescent light emitted by the tagged polymerase during each successive monomer addition or insertion into a growing polymer chain. The method can further comprise relating the measured intensity and/or frequency of emitted fluorescent light to incorporation events and/or to the identification of each inserted or added monomer resulting in a near real-time or real-time readout of the sequence of the a growing nucleic acid sequence—DNA sequence, RNA sequence or mixed DNA/RNA sequences.

The present invention also provides a system for retrieving stored information comprising a molecule having a sequence of known elements representing a data stream, a single-molecule sequencer comprising a polymerase having at least one tag associated therewith, an excitation source adapted to excite at least one tag on the polymerase, and a detector adapted to detect a response from the excited tag on the polymerase, where the response from the at least one tag changes during polymerization of a complementary sequence of elements and the change in response represents a content of the data stream.

The present invention also provides a system for determining sequence information from a single-molecule comprising a molecule having a sequence of known elements, a single-molecule sequencer comprising a polymerase having at least one tag associated therewith, a excitation source adapted to excite at least one tag on the polymerase, and a detector adapted to detect a response from the excited tag on the polymerase, where the response from at least one tag changes during polymerization of a complementary sequence of elements representing the element sequence of the molecule.

The present invention also provides a system for determining sequence information from a single-molecule comprising a molecule having a sequence of known elements, a single-molecule sequencer comprising a polymerase having at least one fluorescent tag associated therewith, an excitation light source adapted to excite at least one fluorescent tag on the polymerase and/or monomer and a fluorescent light detector adapted to detect at least an intensity of emitted fluorescent light from at least one fluorescent tag on the polymerase and/or monomer, where the signal intensity changes each time a new nucleotide or nucleotide analog is polymerized into a complementary sequence and either the duration of the emission or lack of emission or the wavelength range of the emitted light evidences the particular nucleotide or nucleotide analog polymerized into the sequence so that at the completion of the sequencing the data stream is retrieved.

The present invention also provides a system for storing and retrieving data comprising a sequence of nucleotides or nucleotide analogs representing a given data stream; a single-molecule sequencer comprising a polymerase having at least one fluorescent tag covalently attached thereto; an excitation light source adapted to excite the at least one fluorescent tag on the polymerase and/or monomer; and a fluorescent light detector adapted to detect emitted fluorescent light from at least one fluorescent tag on the polymerase and/or monomer, where at least one fluorescent tag emits or fails to emit fluorescent light each time a new nucleotide or nucleotide analog is polymerized into a complementary sequence and either the duration of the emission or lack of emission or the wavelength range of the emitted light evidences the particular nucleotide or nucleotide analog polymerized into the sequence so that at the completion of the sequencing the data stream is retrieved.

The term monomer as used herein means any compound that can be incorporated into a growing molecular chain by a given polymerase. Such monomers include, without limitations, naturally occurring nucleotides (e.g., ATP, GTP, TTP, UTP, CTP, dATP, dGTP, dTTP, dUTP, dCTP, synthetic analogs), precursors for each nucleotide, non-naturally occurring nucleotides and their precursors or any other molecule that can be incorporated into a growing polymer chain by a given polymerase. Additionally, amino acids (natural or synthetic) for protein or protein analog synthesis, mono saccharides for carbohydrate synthesis or other monomeric syntheses.

The term polymerase as used herein means any molecule or molecular assembly that can polymerize a set of monomers into a polymer having a predetermined sequence of the monomers, including, without limitation, naturally occurring polymerases or reverse transcriptases, mutated naturally occurring polymerases or reverse transcriptases, where the mutation involves the replacement of one or more or many amino acids with other amino acids, the insertion or deletion of one or more or many amino acids from the polymerases or reverse transcriptases, or the conjugation of parts of one or more polymerases or reverse transcriptases, non-naturally occurring polymerases or reverse transcriptases. The term polymerase also embraces synthetic molecules or molecular assembly that can polymerize a polymer having a pre-determined sequence of monomers, or any other molecule or molecular assembly that may have additional sequences that facilitate purification and/or immobilization and/or molecular interaction of the tags, and that can polymerize a polymer having a pre-determined or specified or templated sequence of monomers.

Single Site Tagged Polymerizing or Depolymerizing Agents

The present invention provides a composition comprising a polymerizing agent including at least one molecular and/or atomic tag located at or near, associated with or covalently bonded to a site on the agent, where a detectable property of the tag undergoes a change before, during and/or after monomer incorporation.

The present invention provides a composition comprising a polymerizing agent including at least one molecular and/or atomic tag located at or near, associated with or covalently bonded to a site on the agent, where a detectable property has a first value when the polymerase is in a first state and a second value when the polymerase is in a second state during monomer incorporation.

The present invention provides a composition comprising a depolymerizing agent including at least one molecular and/or atomic tag located at or near, associated with or covalently bonded to a site on the agent, where a detectable property of the tag undergoes a change before, during and/or after monomer removal.

The present invention provides a composition comprising a polymerizing agent including at least one molecular and/or atomic tag located at or near, associated with or covalently bonded to a site on the agent, where a detectable property has a first value when the polymerase is in a first state and a second value when the polymerase is in a second state during monomer removal.

Single Site Tagged Polymerase

The present invention provides a composition comprising a polymerase including at least one molecular and/or atomic tag located at or near, associated with or covalently bonded to a site on the polymerase, where a detectable property of the tag undergoes a change before, during and/or after monomer incorporation.

The present invention provides a composition comprising a polymerase including at least one molecular and/or atomic tag located at or near, associated with or covalently bonded to a site on the polymerase, where a detectable property has a first value when the polymerase is in a first state and a second value when the polymerase is in a second state during monomer incorporation.

The present invention provides a composition comprising an exonuclease including at least one molecular and/or atomic tag located at or near, associated with or covalently bonded to a site on the agent, where a detectable property of the tag undergoes a change before, during and/or after monomer removal.

The present invention provides a composition comprising an exonuclease including at least one molecular and/or atomic tag located at or near, associated with or covalently bonded to a site on the agent, where a detectable property has a first value when the polymerase is in a first state and a second value when the polymerase is in a second state during monomer removal.

The present invention provides a composition comprising an enzyme modified to produce a detectable response prior to, during and/or after interaction with an appropriately modified monomer, where the monomers are nucleotides, nucleotide analogs, amino acids, amino acid analogs, monosaccharides, monosaccharide analogs or mixtures or combinations thereof.

The present invention provides a composition comprising a polymerase including at least one molecular tag located at or near, associated with or covalently bonded to a site that undergoes conformational change during monomer incorporation, where the tag has a first detection propensity when the polymerase is in a first conformational state and a second detection propensity when the polymerase is in a second conformational state.

The present invention provides a composition comprising a polymerase including at least one chromophore located at or near, associated with or covalently bonded to a site that undergoes conformational change during monomer incorporation, where an intensity and/or frequency of emitted light of the tag has a first value when the polymerase is in a first conformational state and a second value when the polymerase is in a second conformational state.

The present invention provides a composition comprising a polymerase including at least one molecular tag located at or near, associated with or covalently bonded to a site that undergoes conformational change during monomer incorporation, where the tag has a first fluorescence propensity when the polymerase is in a first conformational state and a second fluorescence propensity when the polymerase is in a second conformational state.

The present invention provides a composition comprising a polymerase including a molecular tag located at or near, associated with or covalently bonded to a site that undergoes conformational change during monomer incorporation, where the tag is substantially active when the polymerase is in a first conformational state and substantially inactive when the polymerase is in a second conformational state or substantially inactive when the polymerase is in the first conformational state and substantially active when the polymerase is in the second conformational state.

Multiple Site Tagged Polymerizing and Depolymerizing Agents

The present invention provides a composition comprising a polymerizing agent including at least one pair of molecular tags located at or near, associated with or covalently bonded to a site of the agent, where a detectable property of at least one of the tags undergoes a change before, during and/or after monomer incorporation.

The present invention provides a composition comprising a polymerizing agent including at least one pair of molecular tags located at or near, associated with or covalently bonded to a site of the agent, where a detectable property has a first value when the polymerase is in a first state and a second value when the polymerase is in a second state during monomer incorporation.

The present invention provides a composition comprising a depolymerizing agent including at least one pair of molecular tags located at or near, associated with or covalently bonded to a site of the agent, where a detectable property of at least one of the tags undergoes a change before, during and/or after monomer removal.

The present invention provides a composition comprising a depolymerizing agent including at least one pair of molecular tags located at or near, associated with or covalently bonded to a site of the agent, where a detectable property has a first value when the polymerase is in a first state and a second value when the polymerase is in a second state during monomer removal.

Multiple Site Tagged Polymerase

The present invention provides a composition comprising a polymerase including at least one pair of molecular tags located at or near, associated with or covalently bonded to a site of the polymerase, where a detectable property of at least one of the tags undergoes a change before, during and/or after monomer incorporation.

The present invention provides a composition comprising a polymerase including at least one pair of molecular tags located at or near, associated with or covalently bonded to a site of the polymerase, where a detectable property has a first value when the polymerase is in a first state and a second value when the polymerase is in a second state during monomer incorporation.

The present invention provides a composition comprising an exonuclease including at least one pair of molecular tags located at or near, associated with or covalently bonded to a site of the polymerase, where a detectable property of at least one of the tags undergoes a change before, during and/or after monomer removal.

The present invention provides a composition comprising an exonuclease including at least one pair of molecular tags located at or near, associated with or covalently bonded to a site of the polymerase, where a detectable property has a first value when the polymerase is in a first state and a second value when the polymerase is in a second state during monomer removal.

The present invention provides a composition comprising a polymerase including at least one pair of molecular tags located at or near, associated with or covalently bonded to a site that undergoes conformational change during monomer incorporation, where the detectable property of the pair has a first value when the polymerase is in a first conformational state and a second value when the polymerase is in a second conformational state.

The present invention provides a composition comprising a polymerase including at least one pair of molecules or atoms located at or near, associated with or covalently bonded to a site that undergoes conformational change during monomer incorporation, where the pair interact to form a chromophore when the polymerase is in a first conformational state or a second conformational state.

The present invention provides a composition comprising a polymerase including at least one pair of molecular tags located at or near, associated with or covalently bonded to a site that undergoes conformational change during monomer incorporation, where the tags have a first fluorescence propensity when the polymerase is in a first conformational state and a second fluorescence propensity when the polymerase is in a second conformational state.

The present invention provides a composition comprising a polymerase including at least one pair of molecular tags located at or near, associated with or covalently bonded to a site that undergoes conformational change during monomer incorporation, where the pair is substantially active when the polymerase is in a first conformational state and substantially inactive when the polymerase is in a second conformational state or substantially inactive when the polymerase is in the first conformational state and substantially active when the polymerase is in the second conformational state.

Methods Using Tagged Polymerase

The present invention provides a method for determining when a monomer is incorporated into a growing molecular chain comprising the steps of monitoring a detectable property of a tag, where the tag is located at or near, associated with or covalently bonded to a site on a polymerase or associated with or covalently bonded to a site on the monomer, where the site undergoes a change during monomer incorporation and where the detectable property has a first value when the polymerase is in a first state and a second value when the polymerase is in a second state and cycles from the first value to the second value during each monomer addition.

The present invention provides a method for determining when a monomer is incorporated into a growing molecular chain comprising the steps of monitoring a detectable property of a tag, where the tag is located at or near, associated with or covalently bonded to a site on a polymerase or associated with or covalently bonded to a site on the monomer, where the site undergoes a conformational change during monomer incorporation and where the detectable property has a first value when the polymerase is in a first conformational state and a second value when the polymerase is in a second conformational state and cycles from the first value to the second value during each monomer addition.

The present invention provides a method for determining when a monomer is incorporated into a growing molecular chain comprising the steps of exposing a tagged polymerase to light, monitoring an intensity and/or frequency of fluorescent light emitted by the tagged polymerase and/or monomer, where the tagged polymerase comprises a polymerase including a tag located at or near, associated with or covalently bonded to a site that undergoes conformational change during monomer incorporation or associated with or covalently bonded to a site on the monomer and where the tag emits fluorescent light at a first intensity and/or frequency when the polymerase is in a first conformational state and a second intensity and/or frequency when the polymerase is in a second conformational state and cycles from the first value to the second value during each monomer addition.

Single-Molecule Sequencing Apparatus Using Tagged Polymerase

The present invention provides a composition comprising a single-molecule sequencing apparatus comprising a substrate having a chamber or chip surface in which at least one tagged polymerase is confined therein and a plurality of chambers, each of which includes a specific monomer and a plurality of channels interconnecting the chambers, where each replication complex is sufficiently distant to enable data collection from each complex individually.

The present invention provides a method for single-molecule sequencing comprising the steps of supplying a plurality of monomers to a tagged polymerase confined on a substrate, exposing the tagged polymerase to light and measuring an intensity and/or frequency of fluorescent light emitted by the tagged polymerase. The method can further comprise the step of relating the measured intensity and/or frequency of emitted fluorescent light to incorporation of a specific monomer into a growing DNA chain.

Cooperatively Tagged Monomers and Tagged Polymerizing Agent

The present invention provides a composition comprising a cooperatively tagged polymerizing agent and tagged monomers, where a detectable property of at least one of the tags changes when the tags interact.

The present invention provides a composition comprising a cooperatively tagged depolymerizing agent and tagged depolymerizable monomers, where a detectable property of at least one of the tags changes when the tags interact.

Cooperatively Tagged Monomers and Tagged Polymerizing Agent

The present invention provides a composition comprising a cooperatively tagged polymerase and tagged monomers, where a detectable property of at least one of the tags changes when the tags interact.

The present invention provides a composition comprising a cooperatively tagged polymerase and tagged monomers, where a detectable property of at least one of the tags changes when the tag are within a distance sufficient to cause a change in the intensity and/or frequency of emitted fluorescent light.

The present invention provides a composition comprising a tagged polymerase and tagged monomer precursors, where an intensity and/or frequency of fluorescence light emitted by at least one tag changes when the tags interact.

The present invention provides a composition comprising a tagged polymerase and a tagged monomer precursors, where an intensity and/or frequency of fluorescence light emitted by at least one tag changes when the tags are within a distance sufficient to cause a change in the intensity and/or frequency of emitted fluorescent light.

The present invention provides a single-molecule sequencing apparatus comprising a container having at least one tagged polymerase confined on an interior surface thereof and having a solution containing a plurality of tagged monomers in contact with the interior surface or a subset of tagged monomers and a subset of untagged monomers which together provide all monomers precursor for polymerization.

The present invention provides a method for single-molecule sequencing comprising the steps of supplying a plurality of tagged monomers to a tagged polymerase confined on an interior surface of a container, exposing the tagged polymerase to light and measuring an intensity and/or frequency of fluorescent light emitted by the tagged polymerase. The method can further comprise relating the measured intensity and/or frequency of emitted fluorescent light to incorporation of a specific monomer into a growing DNA chain.

The present invention provides a system for retrieving stored information comprising: (a) a molecule having a sequence of elements representing a data stream; (b) a single-molecule sequencer comprising a polymerase having at least one tag associated therewith; (c) an excitation source adapted to excite the at least one tag on the polymerase; and (d) a detector adapted to detect a response from the tag on the polymerase or on the monomers; where the response from at least one tag changes during polymerization of a complementary sequence of elements and the change in response represents a data stream content.

The present invention provides a system for determining sequence information from a single-molecule comprising: (a) a molecule having a sequence of elements; (b) a single-molecule sequencer comprising a polymerase having at least one tag associated therewith; (c) an excitation source adapted to excite at least one tag on the polymerase or on the monomers; and (d) a detector adapted to detect a response from the tag on the polymerase; where the response from at least one tag changes during polymerization of a complementary sequence of elements representing the element sequence of the molecule.

The present invention provides a system for determining sequence information from an individual molecule comprising: (a) a molecule having a sequence of elements; (b) a single-molecule sequencer comprising a polymerase having at least one fluorescent tag associated therewith; (c) an excitation light source adapted to excite the at least one fluorescent tag on the polymerase or on the monomers; and (d) a fluorescent light detector adapted to detect at least an intensity of emitted fluorescent light from the at least one fluorescent tag on the polymerase; where the intensity change of at least one fluorescent tag emits or fails to emit fluorescent light each time a new nucleotide or nucleotide analog is polymerized into a complementary sequence and either the duration of the emission or lack of emission or the wavelength range of the emitted light evidences the particular nucleotide or nucleotide analog polymerized into the sequence so that at the completion of the sequencing the data stream is retrieved.

The present invention provides a system for storing and retrieving data comprising: (a) a sequence of nucleotides or nucleotide analogs representing a given data stream; (b) a single-molecule sequencer comprising a polymerase having at least one fluorescent tag covalently attached thereto; (c) an excitation light source adapted to excite at least one fluorescent tag on the polymerase; and (d) a fluorescent light detector adapted to detect emitted fluorescent light from at least one fluorescent tag on the polymerase; where at least one fluorescent tag emits or fails to emit fluorescent light each time a new nucleotide or nucleotide analog is polymerized into a complementary sequence and either the duration of the emission or lack of emission or the wavelength range of the emitted light evidences the particular nucleotide or nucleotide analog polymerized into the sequence so that at the completion of the sequencing the data stream is retrieved.

The present invention provides a system for storing and retrieving data comprising: (a) a sequence of nucleotides or nucleotide analogs representing a given data stream; (b) a single-molecule sequencer comprising a polymerase having at least one fluorescent tag covalently attached thereto; (c) an excitation light source adapted to excite the at least one fluorescent tag on the polymerase or the monomers; and (d) a fluorescent light detector adapted to detect emitted fluorescent light from at least one fluorescent tag on the polymerase or the monomers; where at least one fluorescent tag emits or fails to emit fluorescent light each time a new nucleotide or nucleotide analog is polymerized into a complementary sequence and either the duration of the emission or lack of emission or the wavelength range of the emitted light evidences the particular nucleotide or nucleotide analog polymerized into the sequence so that at the completion of the sequencing the data stream is retrieved.

The present invention provides a method for sequencing a molecular sequence comprising the steps of: (a) a sequenced of nucleotides or nucleotide analogs representing a given data stream; (b) a single-molecule sequencer comprising a polymerase having at least one fluorescent tag covalently attached thereto; (c) an excitation light source adapted to excite at least one fluorescent tag on the polymerase or the monomers; and (d) a fluorescent light detector adapted to detect emitted fluorescent light from at least one fluorescent tag on the polymerase; where at least one fluorescent tag emits or fails to emit fluorescent light each time a new nucleotide or nucleotide analog is polymerized into a complementary sequence and either the duration of the emission or lack of emission or the wavelength range of the emitted light evidences the particular nucleotide or nucleotide analog polymerized into the sequence so that at the completion of the sequencing the data stream is retrieved.

The present invention provides a method for synthesizing a γ-phosphate modified nucleotide comprising the steps of attaching a molecular tag to a pyrophosphate group and contacting the modified pyrophosphate with a dNMP to produce a γ-phosphate tagged dNTP.

The present invention provides a method for 5' end-labeling a biomolecule comprising the step of contacting the biomolecule with a kinase able to transfer a γ-phosphate of a γ-phosphate labeled ATP to the 5' end of the biomolecule resulting in a covalently modified biomolecule.

The present invention provides a method for end-labeling a polypeptide or carbohydrate comprising the step of contacting the polypeptide or carbohydrate with an agent able to transfer an atomic or molecular tag to either a carboxy or amino end of a protein or polypeptide or to either the γ-phosphate of a γ-phosphate labeled ATP to the 5' end of the biomolecule resulting in a covalently modified biomolecule.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
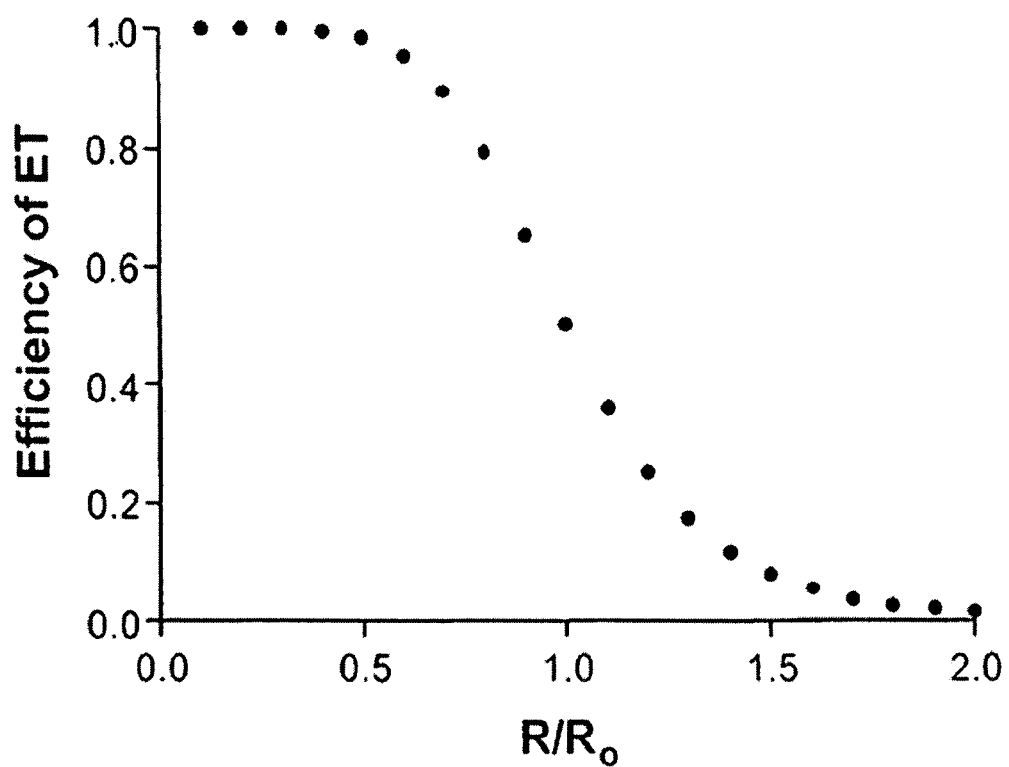
FIG. 1 depicts FRET activity as a function of distance separating the fluorescent donor and acceptor.

The inventors have devised a methodology using tagged monomers such as dNTPs and/or tagged polymerizing agents such as polymerase and/or tagged agents associated with the polymerizing agent such as polymerase associated proteins or probes to directly readout the exact monomer sequence such as a base sequence of an RNA or DNA sequence during polymerase activity. The methodology of this invention is adaptable to protein synthesis or to carbohydrate synthesis or to the synthesis of any molecular sequence where the sequence of monomers provides usable information such as the sequence of a RNA or DNA molecule, a protein, a carbohydrate, a mixed biomolecule or an inorganic or organic sequence of monomers which stores a data stream. The methods and apparatuses using these methods are designed to create new ways to address basic research questions such as monitoring conformation changes occurring during replication and assaying polymerase incorporation fidelity in a variety of sequence contexts. The single-molecule detection systems of this invention are designed to improve fluorescent molecule chemistry, computer modeling, base-calling algorithms, and genetic engineering of biomolecules, especially for real-time or near real-time sequencing. The inventors have also found that the methodology can be adapted to depolymerizing agents such as exonucleases where the polymer sequence is determined by depolymerization instead of polymerization. Moreover, the single-molecule systems of this invention are amendable to parallel and/or massively parallel assays, where tagged polymerases are patterned in arrays on a substrate. The data collected from such arrays can be used to improve sequence confidence and/or to simultaneously sequence DNA regions from many different sources to identify similarities or differences.

The pattern of emission signals is collected, either directly, such as by an Intensified Charge Coupled Devise (ICCD) or through an intermediate or series of intermediates to amplify signal prior to electronic detection, where the signals are decoded and confidence values are assigned to each base to reveal the sequence complementary to that of the template. Thus, the present invention also provides techniques for amplifying the fluorescent light emitted from a fluorescent tag using physical light amplification techniques or molecular cascading agent to amplify the light produced by single-molecular fluorescent events.

The single-molecule DNA sequencing systems of this invention have the potential to replace current DNA sequencing technologies, because the methodology can decrease time, labor, and costs associated with the sequencing process, and can lead to highly scalable sequencing systems, improving the DNA sequence discovery process by at least one to two orders of magnitude per reaction.

The single-molecule DNA sequencing technology of this invention can: (1) make it easier to classify an organism or identify variations within an organism by simply sequencing the genome or a portion thereof; (2) make rapid identification of a pathogen or a genetically-modified pathogen easier, especially in extreme circumstances such as in pathogens used in warfare; and (3) make rapid identification of persons for either law enforcement and military applications easier.

One embodiment of the single-molecule sequencing technology of this invention involves strategically positioning a pair of tags on a DNA polymerase so that as a dNTP is incorporated during the polymerization reaction, the tags change relative separation. This relative change causes a change in a detectable property, such as the intensity and/or frequency of fluorescence from one or both of the tags. A time profile of these changes in the detectable property evidences each monomer incorporation event and provides evidence about which particular dNTP is being incorporated at each incorporation event. The pair of tags do not have to be covalently attached to the polymerase, but can be attached to molecules that associate with the polymerase in such a way that the relative separation of the tags change during base incorporation.

Another embodiment of the single-molecule sequencing technology of this invention involves a single tag strategically positioned on a DNA polymerase that interacts with a tag on a dNTP or separate tags on each DNTP. The tags could be different for each DNTP such as color-coded tags which emit a different color of fluorescent light. As the next dNTP is incorporated during the polymerization process, the identity of the base is indicated by a signature fluorescent signal (color) or a change in a fluorescent signal intensity and/or frequency. The rate of polymerase incorporation can be varied and/or controlled to create an essentially "real-time" or near "real-time" or real-time readout of polymerase activity and base sequence. Sequence data can be collected at a rate of >100,000 bases per hour from each polymerase.

In another embodiment of the single-molecule sequencing technology of this invention, the tagged polymerases each include a donor tag and an acceptor tag situated or located on or within the polymerase, where the distance between the tags changes during dNTP binding, DNTP incorporation and/or chain extension. This change in inter-tag distance results in a change in the intensity and/or wavelength of emitted fluorescent light from the fluorescing tag. Monitoring the changes in intensity and/or frequency of the emitted light provides information or data about polymerization events and the identity of incorporated bases.

In another embodiment, the tags on the polymerases are designed to interact with the tags on the dNTPs, where the interaction changes a detectable property of one or both of the tags. Each fluorescently tagged polymerase is monitored for polymerization using tagged dNTPs to determine the efficacy of base incorporation data derived therefrom. Specific assays and protocols have been developed along with specific analytical equipment to measure and quantify the fluorescent data allowing the determination and identification of each incorporated dNTP. Concurrently, the inventors have identified tagged dNTPs that are polymerized by suitable polymerases and have developed software that analyze the fluorescence emitted from the reaction and interpret base identity. One skilled in the art will recognize that appropriate fluorescently active pairs are well-known in the art and commercially available from such vendors as Molecular Probes located in Oregon or Biosearch Technologies, Inc. in Novato, Calif.

The tagged DNA polymerase for use in this invention are genetically engineered to provide one or more tag binding sites that allow the different embodiments of this invention to operate. Once a suitable polymerase candidate is identified, specific amino acids within the polymerase are mutated and/or modified such reactions well-known in the art; provided, however, that the mutation and/or modification do not significantly adversely affect polymerization efficiency. The mutated and/or modified amino acids are adapted to facilitate tag attachment such as a dye or fluorescent donor or acceptor molecule in the case of light activated tags. Once formed, the engineered polymerase can be contacted with one or more appropriate tags and used in the apparatuses and methods of this invention.

Engineering a polymerase to function as a direct molecular sensor of DNA base identity provides a route to a fast and potentially real-time enzymatic DNA sequencing system. The single-molecule DNA sequencing system of this invention can significantly reduce time, labor, and costs associated with the sequencing process and is highly scalable. The single-molecule DNA sequencing system of this invention: (1) can improve the sequence discovery process by at least two orders of magnitude per reaction; (2) is not constrained by the length limitations associated with the degradation-based, single-molecule methods; and (3) allows direct sequencing of desired (target) DNA sequences, especially genomes without the need for cloning or PCR amplification, both of which introduce errors in the sequence. The systems of this invention can make easier the task of classifying an organism or identifying variations within an organism by simply sequencing the genome in question or any desired portion of the genome. The system of this invention is adapted to rapidly identify pathogens or engineered pathogens, which has importance for assessing health-related effects, and for general DNA diagnostics, including cancer detection and/or characterization, genome analysis, or a more comprehensive form of genetic variation detection. The single-molecule DNA sequencing system of this invention can become an enabling platform technology for single-molecule genetic analysis.

The single-molecule sequencing systems of this invention have the following advantages: (1) the systems eliminates sequencing reaction processing, gel or capillary loading, electrophoresis, and data assembly; (2) the systems results in significant savings in labor, time, and costs; (3) the systems allows near real-time or real-time data acquisition, processing and determination of incorporation events (timing, duration, etc.), base sequence, etc.; (4) the systems allows parallel or massively parallel sample processing in microarray format; (5) the systems allows rapid genome sequencing, in time frames of a day or less; (6) the systems requires very small amount of material for analysis; (7) the systems allows rapid genetic identification, screening and characterization of animals including humans or pathogen; (8) the systems allows large increases in sequence throughput; (9) the system can avoid error introduced in PCR, RT-PCR, and transcription processes; (10) the systems can allow accurate sequence information for allele-specific mutation detection; (11) the systems allows rapid medical diagnostics, e.g., Single Nucleotide Polymorphism (SNP) detection; (12) the systems allows improvement in basic research, e.g., examination of polymerase incorporation rates in a variety of different sequence contexts; analysis of errors in different contexts; epigenotypic analysis; analysis of protein glycosylation; protein identification; (13) the systems allows the creation of new robust (rugged) single-molecule detection apparatus; (14) the systems allows the development of systems and procedures that are compatible with biomolecules; (15) the systems allows the development genetic nanomachines or nanotechnology; (16) the systems allows the construction of large genetic databases and (17) the system has high sensitivity for low mutation event detection.

Brief Overview of Single-Molecule DNA Sequencing

In one embodiment of the single-molecule DNA sequencing system of this invention, a single tag is attached to an appropriate site on a polymerase and a unique tag is attached to each of the four nucleotides: dATP, dTTP, dCTP and dGTP. The tags on each dNTPs are designed to have a unique emission signature (i.e., different emission frequency spectrum or color), which is directly detected upon incorporation. As a tagged dNTP is incorporated into a growing DNA polymer, a characteristic fluorescent signal or base emission signature is emitted due to the interaction of polymerase tag and the dNTP tag. The fluorescent signals, i.e., the emission intensity and/or frequency, are then detected and analyzed to determine DNA base sequence.

One criteria for selection of the tagged polymerase and/or dNTPs for use in this invention is that the tags on either the polymerase and/or the dNTPs do not interfere with Watson-Crick base-pairing or significantly adversely impact polymerase activity. The inventors have found that dNTPs containing tags attached to the terminal (gamma) phosphate are incorporated by a native Taq polymerase either in combination with untagged dNTPs or using only tagged dNTPs. Tagging the dNTPs on the β and/or γ phosphate group is preferred because the resulting DNA strands do not include any of the dNTP tags in their molecular make up, minimizing enzyme distortion and background fluorescence.

One embodiment of the sequencing system of this invention involves placing a fluorescent donor such as fluorescein or a fluorescein-type molecule on the polymerase and unique fluorescent acceptors such as a d-rhodamine or a similar molecule on each dNTP, where each unique acceptor, when interacting with the donor on the polymerase, generates a fluorescent spectrum including at least one distinguishable frequency or spectral feature. As an incoming, tagged dNTP is bound by the polymerase for DNA elongation, the detected fluorescent signal or spectrum is analyzed and the identity of the incorporated base is determined.

Another embodiment of the sequencing system of this invention involves a fluorescent tag on the polymerase and unique quenchers on the dNTPs, where the quenchers preferably have distinguishable quenching efficiencies for the polymerase tag. Consequently, the identity of each incoming quencher tagged dNTP is determined by its unique quenching efficiency of the emission of the polymerase fluorescent tag. Again, the signals produced during incorporation are detected and analyzed to determine each base incorporated, the sequence of which generates the DNA base sequence.

Reagents

Suitable polymerizing agents for use in this invention include, without limitation, any polymerizing agent that polymerizes monomers relative to a specific template such as a DNA or RNA polymerase, reverse transcriptase, or the like or that polymerizes monomers in a step-wise fashion.

Suitable polymerases for use in this invention include, without limitation, any polymerase that can be isolated from its host in sufficient amounts for purification and use and/or genetically engineered into other organisms for expression, isolation and purification in amounts sufficient for use in this invention such as DNA or RNA polymerases that polymerize DNA, RNA or mixed sequences, into extended nucleic acid polymers. Preferred polymerases for use in this invention include mutants or mutated variants of native polymerases where the mutants have one or more amino acids replaced by amino acids amenable to attaching an atomic or molecular tag, which have a detectable property. Exemplary DNA polymerases include, without limitation, HIV I-Reverse Transcriptase using either RNA or DNA templates, DNA pol I from *T. aquaticus* or *E. coli*, Bateriophage T4 DNA pol, T7 DNA pol or the like. Exemplary RNA polymerases include, without limitation, T7 RNA polymerase or the like.

Suitable depolymerizing agents for use in this invention include, without limitation, any depolymerizing agent that depolymerizes monomers in a step-wise fashion such as exonucleases in the case of DNA, RNA or mixed DNA/RNA polymers, proteases in the case of polypeptides and enzymes or enzyme systems that sequentially depolymerize polysaccharides.

Suitable monomers for use in this invention include, without limitation, any monomer that can be step-wise polymerized into a polymer using a polymerizing agent. Suitable nucleotides for use in this invention include, without limitation, naturally occurring nucleotides, synthetic analogs thereof, analog having atomic and/or molecular tags attached thereto, or mixtures or combinations thereof.

Suitable atomic tag for use in this invention include, without limitation, any atomic element amenable to attachment to a specific site in a polymerizing agent or dNTP, especially Europium shift agents, nmr active atoms ot the like.

Suitable atomic tag for use in this invention include, without limitation, any atomic element amenable to attachment to a specific site in a polymerizing agent or dNTP, especially fluorescent dyes such as d-Rhodamine acceptor dyes including dichloro[R110], dichloro[R6G], dichloro [TAMRA], dichloro[ROX] or the like, fluorescein donor dye including fluorescein, 6-FAM, or the like; Acridine including Acridine orange, Acridine yellow, Proflavin, pH 7, or the like; Aromatic Hydrocarbon including 2-Methylbenzoxazole, Ethyl p-dimethylaminobenzoate, Phenol, Pyrrole, benzene, toluene, or the like; Arylmethine Dyes including Auramine O, Crystal violet, H2O, Crystal violet, glycerol, Malachite Green or the like; Coumarin dyes including 7-Methoxycoumarin-4-acetic acid, Coumarin 1, Coumarin 30, Coumarin 314, Coumarin 343, Coumarin 6 or the like; Cyanine Dye including 1,1'-diethyl-2,2'-cyanine iodide, Cryptocyanine, Indocarbocyanine (C3)dye, Inodicarbocyanine (C5)dye, Indotricarbocyanine (C7)dye, Oxacarbocyanine (C3)dye, Oxadicarbocyanine (C5)dye, Oxatricarbocyanine (C7)dye, Pinacyanol iodide, Stains all, Thiacarbocyanine (C3)dye, ethanol, Thiacarbocyanine (C3) dye, n-propanol, Thiadicarbocyanine (C5)dye, Thiatricarbocyanine (C7)dye, or the like; Dipyrrin dyes including N,N'-Difluoroboryl-1,9-dimethyl-5-(4-iodophenyl)-dipyrrin, N,N'-Difluoroboryl-1,9-dimethyl-5-(4-(2-trimethylsilylethynyl), N,N'-Difluoroboryl-1,9-dimethyl-5-phenydipyrrin, or the like; Merocyanines including 4-(dicyanomethylene)-2-methyl-6-(p-dimethylaminostyryl)-4H-pyran (DCM), acetonitrile, 4-(dicyanomethylene)-2-methyl-6-(p-dimethylaminostyryl)-4H-pyran (DCM), methanol, 4-Dimethylamino-4'-nitrostilbene, Merocyanine 540, or the like; Miscellaneous Dye including 4',6-Diamidino-2-phenylindole (DAPI), 4',6-Diamidino-2-phenylindole (DAPD, dimethylsulfoxide, 7-Benzylamino-4-nitrobenz-2-oxa-1,3-diazole, Dansyl glycine, H2O, Dansyl glycine, dioxane, Hoechst 33258, DMF, Hoechst 33258, H2O, Lucifer yellow CH, Piroxicam, Quinine sulfate, 0.05 M H2SO4, Quinine sulfate, 0.5 M H2SO4, Squarylium dye III, or the like; Oligophenylenes including 2,5-Diphenyloxazole (PPO), Biphenyl, POPOP, p-Quaterphenyl, p-Terphenyl, or the like; Oxazines including Cresyl violet perchlorate, Nile Blue, methanol, Nile Red, Nile blue, ethanol, Oxazine 1, Oxazine 170, or the like; Polycyclic Aromatic Hydrocarbons including 9,10-Bis(phenylethynyl)anthracene, 9,10-Diphenylanthracene, Anthracene, Naphthalene, Perylene, Pyrene, or the like; polyene/polyynes including 1,2-diphenylacetylene, 1,4-diphenylbutadiene, 1,4-diphenylbutadiyne, 1,6-Diphenylhexatriene, Beta-carotene, Stilbene, or the like; Redox-active Chromophores including Anthraquinone, Azobenzene, Benzoquinone, Ferrocene, Riboflavin, Tris(2,2'-bipyridyl)ruthenium(II), Tetrapyrrole, Bilirubin, Chlorophyll a, diethyl ether, Chlorophyll a, methanol, Chlorophyll b, Diprotonated-tetraphenylporphyrin, Hematin, Magnesium octaethylporphyrin, Magnesium octaethylporphyrin (MgOEP), Magnesium phthalocyanine (MgPc), PrOH, Magnesium phthalocyanine (MgPc), pyridine, Magnesium tetramesitylporphyrin (MgTMP), Magnesium tetraphenylporphyrin (MgTPP), Octaethylporphyrin, Phthalocyanine (Pc), Porphin, Tetra-t-butylazaporphine, Tetra-t-butylnaphthalocyanine, Tetrakis(2,6-dichlorophenyl)porphyrin, Tetrakis(o-aminophenyl)porphyrin, Tetramesitylporphyrin (TMP), Tetraphenylporphyrin (TPP), Vitamin B12, Zinc octaethylporphyrin (ZnOEP), Zinc phthalocyanine (ZnPc), pyridine, Zinc tetramesitylporphyrin (ZnTMP), Zinc tetramesitylporphyrin radical cation, Zinc tetraphenylporphyrin (ZnTPP), or the like; Xanthenes including Eosin Y, Fluorescein, basic ethanol, Fluorescein, ethanol, Rhodamine 123, Rhodamine 6G, Rhodamine B, Rose bengal, Sulforhodamine 101, or the like; or mixtures or combination thereof or synthetic derivatives thereof or FRET fluorophore-quencher pairs including DLO-FB 1 (5'-FAM/3'-BHQ-1) DLO-TEB 1 (5'-TET/3'-BHQ-1), DLO-JB1 (5'-JOE/3'-BHQ-1), DLO-HB1 (5'-HEX/3'-BHQ-1), DLO-C3B2 (5'-Cy3/3'-BHQ-2) DLO-TAB2 (5'-TAMRA/3'-BHQ-2), DLO-RB2 (5'-ROX/3'-BHQ-2), DLO-C5B3 (5'-Cy5/3'-BHQ-3), DLO-C55B3 (5'-Cy5.5/3'-BHQ-3), MBO-FB1 (5'-FAM/3'-BHQ-1), MBO-TEB1 (5'TET/3'-BHQ-1), MBO-JB1 (5'-JOE/3'-BHQ-1), MBO-HB1 (5'-HEX/3'-BHQ-1), MBO-C3B2 (5'-Cy3/3'-BHQ-2), MBO-TAB2 (5'-TAMRA/3'-BHQ-2), MBO-RB2 (5'-ROX/3'-BHQ-2); MBO-C5B3 (5'-Cy5/3'-BHQ-3), MBO-C55B3 (5'-Cy5.5/3'-BHQ-3) or similar FRET pairs available from Biosearch Technologies, Inc. of Novato, Calif., tags with nmr active groups, tags with spectral features that can be easily identified such as IR, far IR, visible UV, far UV or the like.

Enzyme Choice

The inventors have found that the DNA polymerase from *Thermus aquaticus*—Taq DNA polymerase I—is ideally suited for use in the single-molecule apparatuses, systems and methods of this invention. Taq DNA Polymerase, sometimes simply referred to herein as Taq, has many attributes that the inventors can utilize in constructing tagged polymerases for use in the inventions disclosed in this application. Of course, ordinary artisans will recognize that other polymerases can be adapted for use in the single-molecule sequencing systems of this invention.

Since Taq DNA polymerase I tolerates so many mutations within or near its active site (as reviewed in Patel et al, J.

Mol Biol., volume 308, pages 823-837, and incorporated herein by reference), the enzyme is more tolerant of enzyme tagging modification(s) and also able to incorporate a wider range of modified nucleotide substrates.

Crystal Structures are Available for Tag DNA Polymerase

There are 13 structures solved for Taq DNA polymerase, with or without DNA template/primer, dNTP, or ddNTP, which allows sufficient information for the selection of amino acid sites within the polymerase to which an atomic and/or molecular tag such as a fluorescent tag can be attached without adversely affecting polymerase activity. See, e.g., Eom et al., 1996; Li et al., 1998a; Li et al., 1998b. Additionally, the inventors have a written program to aid in identifying optimal tag addition sites. The program compares structural data associated with the Taq polymerase in its open and closed form to identify regions in the polymerase structure that are optimally positioned to optimize the difference in conformation extremes between a tag on the polymerase and the DNTP or to optimize a change in separation between two tags on the polymerase, thereby increasing or maximizing changes in a detectable property of one of the tags or tag pair.

Tag DNA Polymerase is Efficiently Expressed in *E. Coli*

The Taq DNA polymerase is efficiently expressed in *E. coli* allowing efficient production and purification of the nascent polymerase and variants thereof for rapid identification, characterization and optimization of an engineered Taq DNA polymerase for use in the single-molecule DNA sequencing systems of this invention.

No Cysteines are Present in the Protein Sequence

The Taq DNA polymerase contains no cysteines, which allows the easy generation of cysteine-containing mutants in which a single cysteine is placed or substituted for an existing amino acid at strategic sites, where the inserted cysteine serves as a tag attachment site.

The Processivity of the Enzyme can be Modified

Although native Taq DNA polymerase may not represent an optimal polymerase for sequencing system of this invention because it is not a very processive polymerase (50-80 nucleotides are incorporated before dissociation), the low processivity may be compensated for by appropriately modifying the base calling software. Alternatively, the processivity of the Taq DNA Polymerase can be enhanced through genetic engineering by inserting into the polymerase gene a processivity enhancing sequence. Highly processive polymerases are expected to minimize complications that may arise from template dissociation effects, which can alter polymerization rate. The processivity of Taq can be genetically altered by introducing the 76 amino acid 'processivity domain' from T7 DNA polymerase between the H and $H_1$ helices (at the tip of 'thumb' region within the polymerase) of Taq. The processivity domain also includes the thioredoxin binding domain (TBD) from T7 DNA polymerase causing the Taq polymerase to be thioredoxin-dependent increasing both the processivity and specific activity of Taq polymerase. See, e.g., Bedford et al., 1997; Bedford et al., 1999.

Taq DNA Polymerase Possesses a 5' to 3' Exonuclease Activity and is Thermostable Single-stranded M13 DNA and synthetic oligonucleotides are used in the initial studies. After polymerase activity is optimized, the sequencing system can be used to directly determine sequence information from an isolated chromosome —a double-stranded DNA molecule. Generally, heating a sample of double-stranded DNA is sufficient to produce or maintain the double-stranded DNA in stranded DNA form for sequencing.

To favor the single-stranded state, the 5' to 3' exonuclease activity of the native Taq DNA polymerase in the enzyme engineered for single-molecule DNA sequencing is retained. This activity of the polymerase is exploited by the 'TaqMan' assay. The exonuclease activity removes a duplex strand that may renature downstream from the replication site using a nick-translation reaction mechanism. Synthesis from the engineered polymerase is initiated either by a synthetic oligonucleotide primer (if a specific reaction start is necessary) or by a nick in the DNA molecule (if multiple reactions are processed) to determine the sequence of an entire DNA molecule.

The Polymerase is Free from 3' to 5' Exonuclease Activity

The Taq DNA polymerase is does not contain 3' to 5' exonuclease activity, which means that the polymerase cannot replace a base, for which fluorescent signal was detected, with another base which would produce another signature fluorescent signal.

All polymerases make replication errors. The 3' to 5' exonuclease activity is used to proofread the newly replicated DNA strand. Since Taq DNA polymerase lacks this proofreading function, an error in base incorporation becomes an error in DNA replication. Error rates for Taq DNA polymerase are 1 error per~100,000 bases synthesized, which is sufficiently low to assure a relatively high fidelity. See, e.g., Eckert and Kunkel, 1990; Cline et al., 1996. It has been suggested and verified for a polymerase that the elimination of this exonuclease activity uncovers a decreased fidelity during incorporation. Thus, Taq polymerase must—by necessity—be more accurate during initial nucleotide selection and/or incorporation, and is therefore an excellent choice of use in the present inventions.

The error rate of engineered polymerases of this invention are assayed by determining their error rates in synthesizing known sequences. The error rate determines the optimal number of reactions to be run in parallel so that sequencing information can be assigned with confidence. The optimal number can be 1 or 10 or more. For example, the inventors have discovered that base context influences polymerase accuracy and reaction kinetics, and this information is used to assign confidence values to individual base calls. However, depending on the goal of a particular sequencing project, it may be more important to generate a genome sequence as rapidly as possible. For example, it may be preferable to generate, or draft, the genome sequence of a pathogen at reduced accuracy for initial identification purposes or for fast screening of potential pathogens.

Taq DNA Polymerase is the Enzyme of Choice for Single-Molecule DNA Seguencing

Engineering the polymerase to function as a direct molecular sensor of DNA base identity provides the fastest enzymatic DNA sequencing system possible. For the reasons detailed above, Taq DNA polymerase is the optimal enzyme to genetically modify and adapt for single-molecule DNA sequencing. Additionally, basic research questions concerning DNA polymerase structure and function during replication can be addressed using this technology advancing single-molecule detection systems and molecular models in other disciplines. The inventors have found that native Taq DNA polymerase incorporates gamma-tagged dNTPs, yielding extended DNA polymers. Importantly, incorporation of a modified nucleotide is not detrimental to polymerase activity and extension of primer strands by incorporation of a γ-tagged nucleotide conforms to Watson-Crick base pairing rules.

Detecting Tagged Polymerase-Nucleotide Interactions

One preferred method for detecting polymerase-nucleotide interactions involves a fluorescence resonance energy transfer-based (FRET-based) method to maximize signal and minimize noise. A FRET-based method exists when the emission from an acceptor is more intense than the emission from a donor, i.e., the acceptor has a higher fluorescence quantum yield than the donor at the excitation frequency. The efficiency of FRET method can be estimated form computational models. See, e.g., Furey et al., 1998; Clegg et al., 1993; Mathies et al., 1990. The efficiency of energy transfer (E) is computed from the equation (1):

$$E=1/(1+[R/R^0]^6) \quad (1)$$

where $R_0$ is the Förster critical distance at E=0.5. $R_0$ is calculated from equation (2):

$$R_0=(9.79\times10^3)(\kappa^2 n^{-4} Q_D J_{DA})^{1/6} \quad (2)$$

where n is the refractive index of the medium (n=1.4 for aqueous solution), $\kappa^2$ is a geometric orientation factor related to the relative angle of the two transition dipoles ($\kappa^2$ is generally assumed to be ⅔), $J_{DA}$ [M$^{-1}$ cm$^3$] is the overlap integral representing the normalized spectral overlap of the donor emission and acceptor absorption, and $Q_D$ is the quantum yield. The overlap integral is computed from equation (3):

$$J_{DA}=[\int F_D(\lambda)\epsilon_A(\lambda)\lambda^4 d\lambda]/[\int F_D(\lambda)d\lambda] \quad (3)$$

where $F_D$ is the donor emission, $\epsilon_A$ is the acceptor absorption. $Q_D$ is calculated from equation (4):

$$Q_D=Q_{RF}(I_D/I_{RF})(A_{RF}/A_D) \quad (4)$$

where $I_D$ and $I_{RF}$ are the fluorescence intensities of donor and a reference compound (fluorescein in 0.1N NaOH), and $A_{RF}$ and $A_D$ are the absorbances of the reference compound and donor. $Q_{RF}$ is the quantum yield of fluorescein in 0.1N NaOH and is taken to be 0.90.

R, the distance between the donor and acceptor, is measured by looking at different configurations (e.g., conformations) of the polymerase in order to obtain a conformationally averaged value. If both tags are on the polymerase, then R is the distance between the donor and acceptor in the open and closed conformation, while if the donor is on the polymerase and the acceptor on the dNTP, R is the distance between the donor and acceptor when the dNTP is bound to the polymerase and the polymerase is its closed form.

The distance between the tagged γ-phosphate and the selected amino acid sites for labeling in the open versus closed polymerase conformation delineates optimal dye combinations. If the distance (R) between the donor and acceptor is the same as $R_0$ ($R_0$ is the Förster critical distance), FRET efficiency (E) is 50%. If R is more than 1.5 $R_0$, the energy transfer efficiency becomes negligible (E<0.02). Sites within the enzyme at which R/$R_0$ differ by more than 1.6 in the open versus closed forms are identified and, if necessary, these distances and/or distance differences can be increased through genetic engineering. A plot of FRET efficiency verses distance is shown in FIG. 1.

Fluorescent Dye Selection Process

Dye sets are chosen to maximize energy transfer efficiency between a tagged dNTP and a tag on the polymerase when the polymerase is in its closed configuration and to minimize energy transfer efficiency between the tag on the dNTP (either non-productively bound or in solution) and the tag on the polymerase when the polymerase is in its open configuration. Given a molarity of each nucleotide in the reaction medium of no more than about 1 μM, an average distance between tagged nucleotides is calculated to be greater than or equal to about 250 Å. Because this distance is several fold larger than the distance separating sites on the polymerase in its open to closed conformational, minimal FRET background between the polymerase and free dNTPs is observed. Preferably, nucleotide concentrations are reduced below 1 μM. Reducing dNTP concentrations to levels of at least <10% of the $K_m$, further minimizes background fluorescence and provides a convenient method for controlling the rate of the polymerase reaction for the real-time monitoring. Under such conditions, the velocity of the polymerization reaction is linearly proportional to the dNTP concentration and, thus, highly sensitive to regulation. Additionally, the use of a single excitation wavelength allows improved identification of unique tags on each dNTP. A single, lower-wavelength excitation laser is used to achieve high selectivity.

In one preferred embodiment, a fluorescence donor is attached to a site on the polymerase comprising a replaced amino acid more amenable to donor attachment such as cysteine and four unique fluorescence acceptors are attached to each dNTP. For example, fluorescein is attached to a site on the polymerase and rhodamine, rhodamine derivatives and/or fluorescein derivatives are attached to each dNTP. Each donor-acceptor fluorophore pair is designed to have an absorption spectra sufficiently distinct from the other pairs to allow separate identification after excitation. Preferably, the donor is selected such that the excitation light activates the donor, which then efficiency transfers the excitation energy to one of the acceptors. After energy transfer, the acceptor emits it unique fluorescence signature. The emission of the fluorescence donor must significant overlap with the absorption spectra of the fluorescence acceptors for efficient energy transfer. However, the methods of this invention can also be performed using two, three or four unique fluorescence donor-acceptor pairs, by running parallel reactions.

Fluorophore choice is a function of not only its enzyme compatibility, but also its spectral and photophysical properties. For instance, it is critical that the acceptor fluorophore does not have any significant absorption at the excitation wavelength of the donor fluorophore, and less critical (but also desirable) is that the donor fluorophore does not have emission at the detection wavelength of the acceptor fluorophore. These spectral properties can be attenuated by chemical modifications of the fluorophore ring systems.

Although the dNTPs are amenable to tagging at several sites including the base, the sugar and the phosphate groups, the dNTPs are preferably tagged at either the β and/or γ phosphate. Tagging the terminal phosphates of dNTP has a unique advantage. When the incoming, tagged dNTP is bound to the active site of the polymerase, significant FRET from the donor on the polymerase to the acceptor on the dNTP occurs. The unique fluorescence of the acceptor identifies which dNTP is incorporated. Once the tagged dNTP is incorporated into the growing DNA chain, the fluorescence acceptor, which is now attached to the pyrophosphate group, is released to the medium with the cleaved pyrophosphate group. In fact, the growing DNA chain includes no fluorescence acceptor molecules at all. In essence, FRET occurs only between the donor on the polymerase and incoming acceptor-labeled dNTP, one at a time. This approach is better than the alternative attachment of the acceptor to a site within the dNMP moiety of the dNTP or the use of multiply-modified dNTPs. If the acceptor is attached to a site other than the β or γ phosphate group, it becomes part of the growing DNA chain and the DNA chain will contain multiple fluorescence acceptors. Interference with the polymerization reaction and FRET measurements would likely occur.

If the fluorescence from the tagged dNTPs in the polymerizing medium (background) is problematic, collisional quenchers can be added to the polymerizing medium that do not covalently interact with the acceptors on the dNTPs and quench fluorescence from the tagged dNTPs in the medium. Of course, the quenchers are also adapted to have insignificant contact with the donor on the polymerase. To minimize interaction between the collisional quenchers and the donor on the polymerase, the polymerase tag is preferably localized internally and shielded from the collisional quenchers or the collisional quencher can be made sterically bulky or associate with a sterically bulky group to decrease interaction between the quencher and the polymerase.

Another preferred method for detecting polymerase-nucleotide interactions involves using nucleotide-specific quenching agents to quench the emission of a fluorescent tag on the polymerase. Thus, the polymerase is tagged with a fluorophore, while each dNTP is labeled with a quencher for the fluorophore. Typically, DABCYL(4-(4'-dimethylaminophenylazo)benzoic acid is a universal quencher, which absorbs energy from a fluorophore, such as 5-(2'-aminoethyl)aminonaphthalene-1-sulfonic acid (AEANS) and dissipates heat. Preferably, a quencher is selected for each dNTP so that when each quencher is brought into close proximity to the fluorophore, a distinguishable quenching efficiency is obtained. Therefore, the degree of quenching is used to identify each dNTP as it is being incorporated into the growing DNA chain. One advantage of this preferred detection method is that fluorescence emission comes from a single source rendering background noise negligible. Although less preferred, if only two or three suitable quenchers are identified, then two or three of the four dNTPs are labeled and a series of polymerization reaction are made each time with a different pair of the labeled dNTPs. Combining the results from these runs, generates a complete sequence of the DNA molecule.

Site Selection for Labeling the TAQ Polymerase and dNTPs

Although the present invention is directed to attaching any type of atomic and/or molecular tag that has a detectable property, the processes for site selection and tag attachment are illustrated using a preferred class of tags, namely fluorescent tags.

Fluorescent Labeling of Polymerase and/or dNTPs

The fluorescence probes or quenchers attached to the polymerase or dNTPs are designed to minimize adverse effects on the DNA polymerization reaction. The inventors have developed synthetic methods for chemically tagging the polymerase and dNTPs with fluorescence probes or quenchers.

In general, the polymerase is tagged by replacing a selected amino acid codon in the DNA sequence encoding the polymerase with a codon for an amino acid that more easily reacts with a molecular tag such as cysteine via mutagenesis. Once a mutated DNA sequence is prepared, the mutant is inserted into E. coli for expression. After expression, the mutant polymerase is isolated and purified. The purified mutant polymerase is then tested for polymerase activity. After activity verification, the mutant polymerase is reacted with a slight molar excess of a desired tag to achieve near stoichiometric labeling. Alternatively, the polymerase can be treated with an excess amount of the tag and labeling followed as a function of time. The tagging reaction is than stopped when near stoichiometric labeling is obtained.

If the mutant polymerase includes several sites including the target residue that can undergo tagging with the desired molecular tag, then the tagging reaction can also be carried out under special reaction conditions such as using a protecting group or competitive inhibitor and a reversible blocking group, which are later removed. If the target amino acid residue in the mutant polymerase is close to the active dNTP binding site, a saturating level of a protecting group or a competitive inhibitor is first added to protect the target residue and a reversible blocking group is subsequently added to inactivate non-target residues. The protecting group or competitive inhibitor is then removed from the target residue, and the mutant polymerase is treated with the desired tag to label the target residue. Finally, the blocking groups are chemically removed from non-target residues in the mutant polymerase and removed to obtain a tagged mutant polymerase with the tag substantially to completely isolated on the target residue.

Alternatively, if the target residue is not near the active site, the polymerase can be treated with a blocking group to inactivate non-target residues. After removal of unreacted blocking group, the mutant polymerase is treated with the desired tag for labeling the target residue. Finally, the blocking groups are chemically removed from the non-target residues in the mutant polymerase and removed to obtain the tagged mutant polymerase.

Amino Acid Site Selection for the Tag Polymerase

The inventors have identified amino acids in the Taq polymerase that are likely to withstand mutation and subsequent tag attachment such as the attachment of a fluorescent tag. While many sites are capable of cysteine replacement and tag attachment, preferred sites in the polymerase were identified using the following criteria: (1) they are not in contact with other proteins; (2) they do not alter the conformation or folding of the polymerase; and (3) they are not involved in the function of the protein. The selections were accomplished using a combination of mutational studies including sequence analyses data, computational studies including molecular docking data and assaying for polymerase activity and fidelity. After site mutation, computational studies will be used to refine the molecular models and help to identify other potential sites for mutation.

Regions of the protein surface that are not important for function were identified, indirectly, by investigating the variation in sequence as a function of evolutionary time and protein function using the evolutionary trace method. See, e.g., Lichtarge et al., 1996. In this approach, amino acid residues that are important for structure or function are found by comparing evolutionary mutations and structural homologies. The polymerases are ideal systems for this type of study, as there are many crystal and co-crystal structures and many available sequences. The inventors have excluded regions of structural/functional importance from sites selection for mutation/labeling. In addition, visual inspection and overlays of available crystal structures of the polymerase in different conformational states, provided further assistance in identifying amino acid sites near the binding site for dNTPs. Some of the chosen amino acids sites are somewhat internally located and preferably surround active regions in the polymerase that undergo changes during base incorporation, such as the dNTP binding regions, base incorporation regions, pyrophosphate release regions, etc. These internal sites are preferred because a tag on these sites show reduced background signals during detection, i.e., reduce interaction between the polymerase enzyme and non-specifically associated tagged dNTPs, when fluorescently tagged dNTPs are used.

Once tagged mutant polymerases are prepared and energy minimized in a full solvent environment, estimates of the effect on the structure of the polymerase due to the mutation and/or labeling are generated to provide information about relative tag positioning and separation. This data is then used to estimate FRET efficiencies prior to measurement. Of course, if the dNTPs are tagged with quenchers, then these considerations are not as important.

Another aspect of this invention involves the construction of molecular mechanics force field parameters for atomic and/or molecular tags such as fluorescent tags used to tag the dNTPs and the polymerase and parameters for the fluorescent tagged amino acid on the polymerase and/or dNTP. Force field parameters are using quantum mechanical studies to obtain partial charge distributions and energies for relevant intramolecular conformations (i.e., for the dihedral angle definitions) derived from known polymerase crystal structures.

Ionization states of each ionizable residue are estimated using an electrostatic model in which the protein is treated as a low dielectric region and the solvent as a high dielectric, using the UHBD program. See, e.g., Antosiewicz et al., 1994; Briggs and Antosiewicz, 1999; Madura et al., 1995. The electrostatic free energies of ionization of each ionizable residue are computed by solving the Poisson-Boltzmann equation for each residue. These individual ionization free energies are modified to take into account coupled titration behavior resulting in a set of self-consistent predicted ionization states. These predicted ionization free energies are then recalculated so that shifts in ionization caused by the binding of a dNTP are taken into account. Unexpected ionization states are subject to further computational and experimental studies, leading to a set of partial charges for each residue in the protein, i.e., each ionizable residue in the protein can have a different charge state depending on the type of attached tag or amino acid substitution.

To further aid in amino acid site selection, an electrostatic potential map is generated from properties of the molecular surface of the Taq polymerase/DNA complex, screened by solvent and, optionally, by dissolved ions (i.e., ionic strength) using mainly the UHBD program. The map provides guidance about binding locations for the dNTPs and the electrostatic environment at proposed mutation/labeling sites.

The molecular models generated are designed to be continually refined taking into account new experimental data, allowing the construction of improved molecular models, improved molecular dynamics calculations and improved force field parameters so that the models better predict system behavior for refining tag chemistry and/or tag positioning, predicting new polymerase mutants, base incorporation rates and polymerase fidelity.

Molecular docking simulations are used to predict the docked orientation of the natural and fluorescently labeled dNTPs, within the polymerase binding pocket. The best-docked configurations are energy minimized in the presence of an explicit solvent environment. In conjunction with amino acid sites in the polymerase selected for labeling, the docking studies are used to analyze how the tags interact and to predict FRET efficiency for each selected amino acid site.

With the exception of the electrostatics calculations, all docking, quantum mechanics, molecular mechanics, and molecular dynamics calculations are and will be performed using the HyperChem (v6.0) computer program. The HyperChem software runs on PCs under a Windows operating system. A number of computer programs for data analysis or for FRET prediction (as described below) are and will be written on a PC using the Linux operating system and the UHBD program running under Linux.

Analysis of Polymerase Structures

Co-crystal structures solved for DNA polymerase I (DNA pol I) from *E. coli, T. aquaticus, B. stearothermophilus*, T7 bacteriophage, and human pol β demonstrate that (replicative) polymerases share mechanistic and structural features. The structures that capture Taq DNA polymerase in an 'open' (non-productive) conformation and in a 'closed' (productive) conformation are of particular importance for identifying regions of the polymerase that undergo changes during base incorporation. The addition of the nucleotide to the polymerase/primer/template complex is responsible for the transition from its open to its closed conformation. Comparison of these structures provides information about the conformational changes that occur within the polymerase during nucleotide incorporation. Specifically, in the closed conformation, the tip of the fingers domain is rotated inward by 46°, thereby positioning the dNTP at the 3' end of the primer strand in the polymerase active site. The geometry of this terminal base pair is precisely matched with that of its binding pocket. The binding of the correct, complementary base facilitates formation of the closed conformation, whereas incorrect dNTP binding does not induce this conformational change. Reaction chemistry occurs when the enzyme is in the closed conformation.

Figure 2:
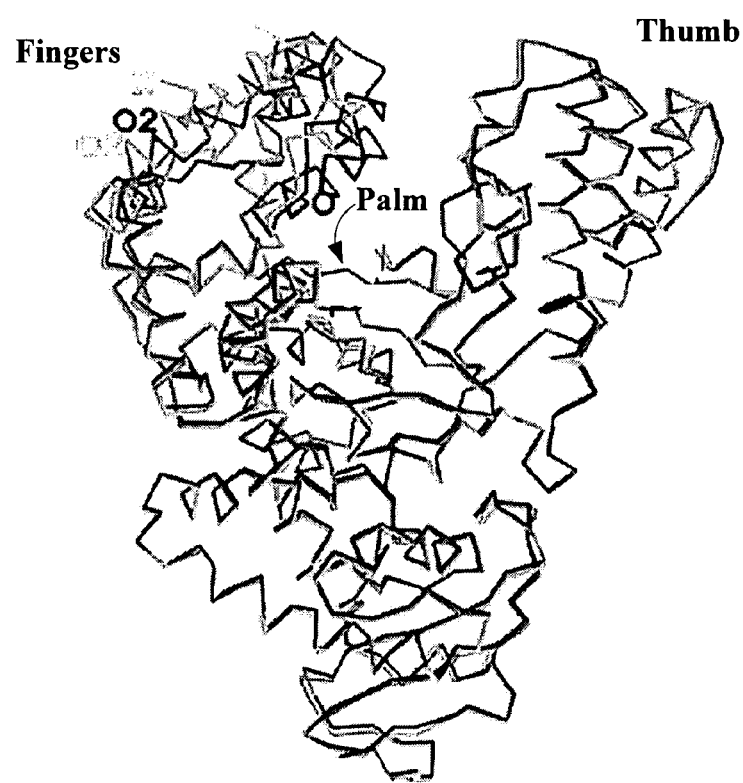
FIG. 2 depicts the open and closed ternary complex forms of the large fragment of Taq DNA pol I (Klentaq 1)

Referring now to FIG. 2, the open and closed ternary complex forms of the large fragment of Taq DNA pol I (Klentaq 1) are shown in a superimposition of their Cα tracings. The ternary complex contains the enzyme, the ddCTP and the primer/template duplex DNA. The open structure is shown in magenta and the closed structure is shown in yellow. The disorganized appearance in the upper left portion of the protein shows movement of the 'fingers' domain in open and closed conformations.

Using a program to determine the change in position of amino acids in the open and closed conformation of the polymerase relative to the gamma phosphate of a bound ddGTP from two different crystal structures of the Taq polymerase containing the primer and bound ddGTP, lists of the 20 amino acid sites that undergo the largest change in position for mutation and labeling were identified. The distances were calculated for each amino acid between their alpha and beta carbon atoms and the gamma phosphate group of the bound ddGTP. Lists derived from the two different sets of crystallographic data for the Taq polymerase are given in Tables I, II, III and IV.

TABLE I

The 20 Amino Acid Sites Undergoing the Largest Positional Change in 2ktq Data Between the Open Form of the Polymerase to the Closed Form of the Polymerase Relative to the Alpha Carbon of the Residue

| Residue Location | Residue Identity | Change in Distance (Å) |
|---|---|---|
| 517 | Alanine | 9.10 |
| 516 | Alanine | 6.86 |

TABLE I-continued

The 20 Amino Acid Sites Undergoing the Largest Positional Change in 2ktq Data Between the Open Form of the Polymerase to the Closed Form of the Polymerase Relative to the Alpha Carbon of the Residue

| Residue Location | Residue Identity | Change in Distance (Å) |
| --- | --- | --- |
| 515 | Serine | 6.53 |
| 513 | Serine | 6.40 |
| 518 | Valine | 5.12 |
| 514 | Threonine | 3.94 |
| 488 | Asparagine | 3.73 |
| 487 | Arginine | 3.50 |
| 489 | Glutamine | 3.13 |
| 495 | Phenylalanine | 3.05 |
| 491 | Glutamic acid | 2.90 |
| 486 | Serine | 2.78 |
| 490 | Leucine | 2.62 |
| 586 | Valine | 2.61 |
| 492 | Arginine | 2.60 |
| 462 | Glutamic acid | 2.59 |
| 483 | Asparagine | 2.47 |
| 685 | Proline | 2.46 |
| 587 | Arginine | 2.44 |
| 521 | Alanine | 2.38 |

TABLE II

The 20 Amino Acid Sites Undergoing the Largest Positional Change in 2ktq Data Between the Open Form of the Polymerase to the Closed Form of the Polymerase Relative to the Beta Carbon of the Residue

| Residue Location | Residue Identity | Change in Distance (Å) |
| --- | --- | --- |
| 517 | Alanine | 10.98 |
| 516 | Alanine | 9.05 |
| 515 | Serine | 8.02 |
| 513 | Serine | 7.46 |
| 518 | Valine | 5.47 |
| 685 | Proline | 5.16 |
| 487 | Arginine | 4.24 |
| 495 | Phenylalanine | 3.94 |
| 488 | Aspartic Acid | 3.88 |
| 520 | Glutamic Acid | 3.66 |
| 491 | Glutamic Acid | 3.41 |
| 587 | Arginine | 3.39 |
| 521 | Alanine | 3.33 |
| 498 | Leucine | 3.21 |
| 489 | Glutamine | 3.08 |
| 514 | Threonine | 2.97 |
| 581 | Leucine | 2.93 |
| 483 | Asparagine | 2.92 |
| 497 | Glutamic Acid | 2.91 |
| 462 | Glutamic Acid | 2.83 |

TABLE III

The 20 Amino Acid Sites Undergoing the Largest Positional Change in 3ktq Data Between the Open Form of the Polymerase to the Closed Form of the Polymerase Relative to the Alpha Carbon of the Residue

| Residue Location | Residue Identity | Change in Distance (Å) |
| --- | --- | --- |
| 517 | Alanine | 8.95 |
| 656 | Proline | 8.75 |
| 657 | Leucine | 8.59 |
| 655 | Aspartic Acid | 8.05 |
| 660 | Arginine | 7.35 |
| 658 | Metionine | 7.06 |

TABLE III-continued

The 20 Amino Acid Sites Undergoing the Largest Positional Change in 3ktq Data Between the Open Form of the Polymerase to the Closed Form of the Polymerase Relative to the Alpha Carbon of the Residue

| Residue Location | Residue Identity | Change in Distance (Å) |
| --- | --- | --- |
| 659 | Arginine | 6.69 |
| 654 | Valine | 6.60 |
| 513 | Serine | 6.59 |
| 516 | Alanine | 6.57 |
| 515 | Serine | 6.36 |
| 653 | Alanine | 6.16 |
| 661 | Alanine | 5.94 |
| 652 | Glutamic Acid | 5.44 |
| 647 | Phenylalanine | 5.25 |
| 649 | Valine | 5.22 |
| 518 | Valine | 5.15 |
| 644 | Serine | 5.08 |
| 643 | Alanine | 5.01 |
| 650 | Proline | 4.72 |

TABLE IV

The 20 Amino Acid Sites Undergoing the Largest Positional Change in 3ktq Data Between the Open Form of the Polymerase to the Closed Form of the Polymerase Relative to the Beta Carbon of the Residue

| Residue Location | Residue Identity | Change in Distance (Å) |
| --- | --- | --- |
| 517 | Alanine | 10.85 |
| 656 | Proline | 9.05 |
| 657 | Leucine | 8.75 |
| 516 | Alanine | 8.68 |
| 655 | Aspartic Acid | 8.24 |
| 515 | Serine | 7.92 |
| 660 | Arginine | 7.89 |
| 513 | Serine | 7.60 |
| 659 | Arginine | 6.98 |
| 658 | Metionine | 6.77 |
| 654 | Valine | 6.25 |
| 653 | Alanine | 6.14 |
| 661 | Alanine | 6.04 |
| 643 | Alanine | 5.74 |
| 649 | Valine | 5.55 |
| 647 | Phenylalanine | 5.45 |
| 518 | Valine | 5.42 |
| 652 | Glutamic Acid | 5.13 |
| 644 | Serine | 4.89 |
| 487 | Arginine | 4.77 |

The above listed amino acids represent preferred amino acid sites for cysteine replacement and subsequent tag attachment, because these sites represent the sites in the Taq polymerase the undergo significant changes in position during base incorporation.

To further refine the amino acid site selection, visualization of the polymerase in its open and closed conformational extremes for these identified amino acid sites is used so that the final selected amino acid sites maximize signal and minimize background noise, when modified to carry fluorescent tags for analysis using the FRET methodology. Amino acid changes that are not predicted to significantly affect the protein's secondary structure or activity make up a refined set of amino acid sites in the Taq polymerase for mutagenesis and fluorescent modification so that the tag is shielded from interaction with free dNTPs. The following three panels illustrate the protocol used in this invention to refine amino acid site selection from the about list of amino acids that undergo the largest change in position relative to a bound ddGTP as the polymerase transitions from the open to the closed form.

Figure 3A:
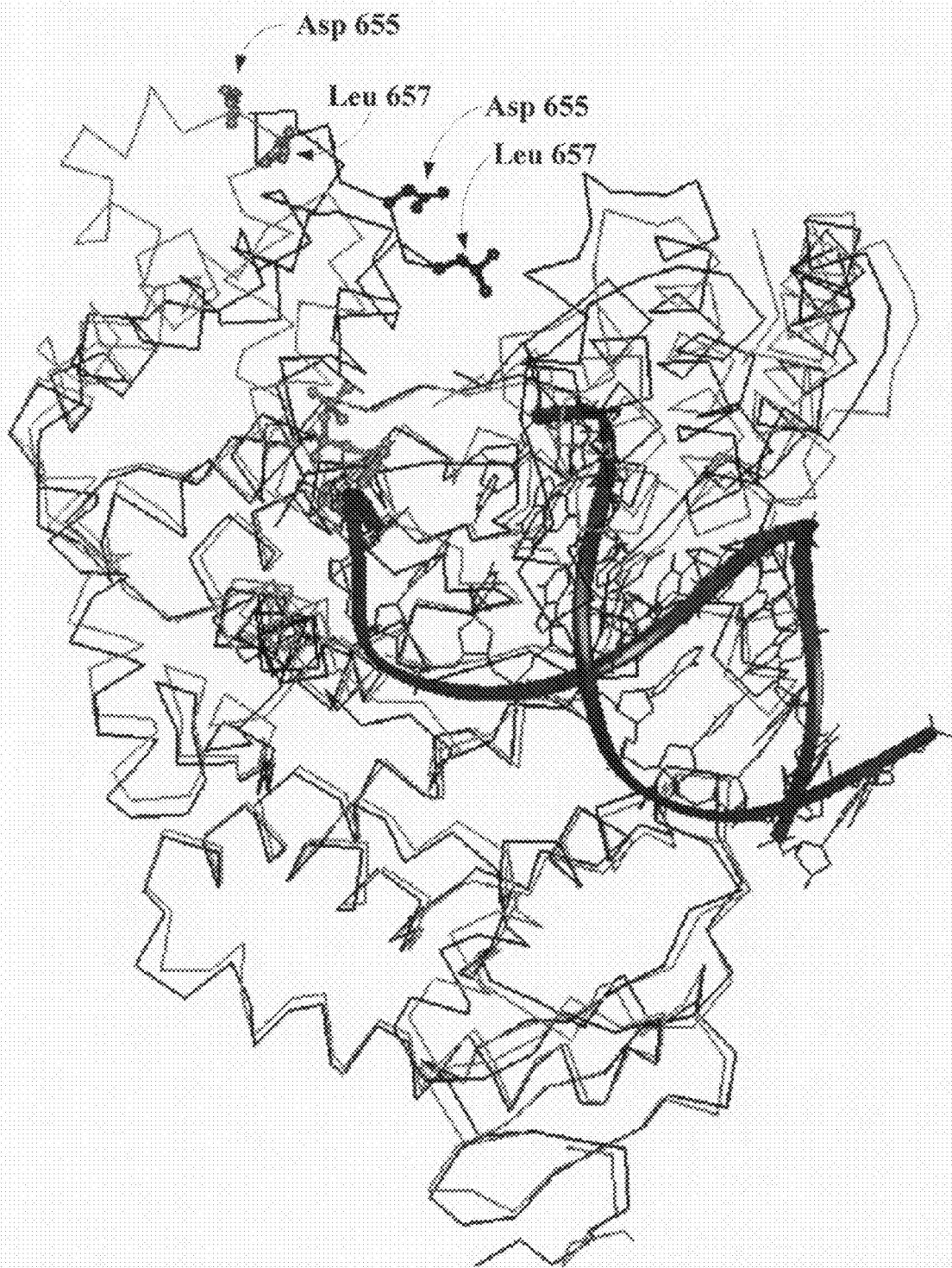
FIGS. 3A-C depicts an overlay between 3ktq (closed 'black') and 1tau (open 'light blue'), the large fragment of Taq DNA polymerase I.
Figure 3B:
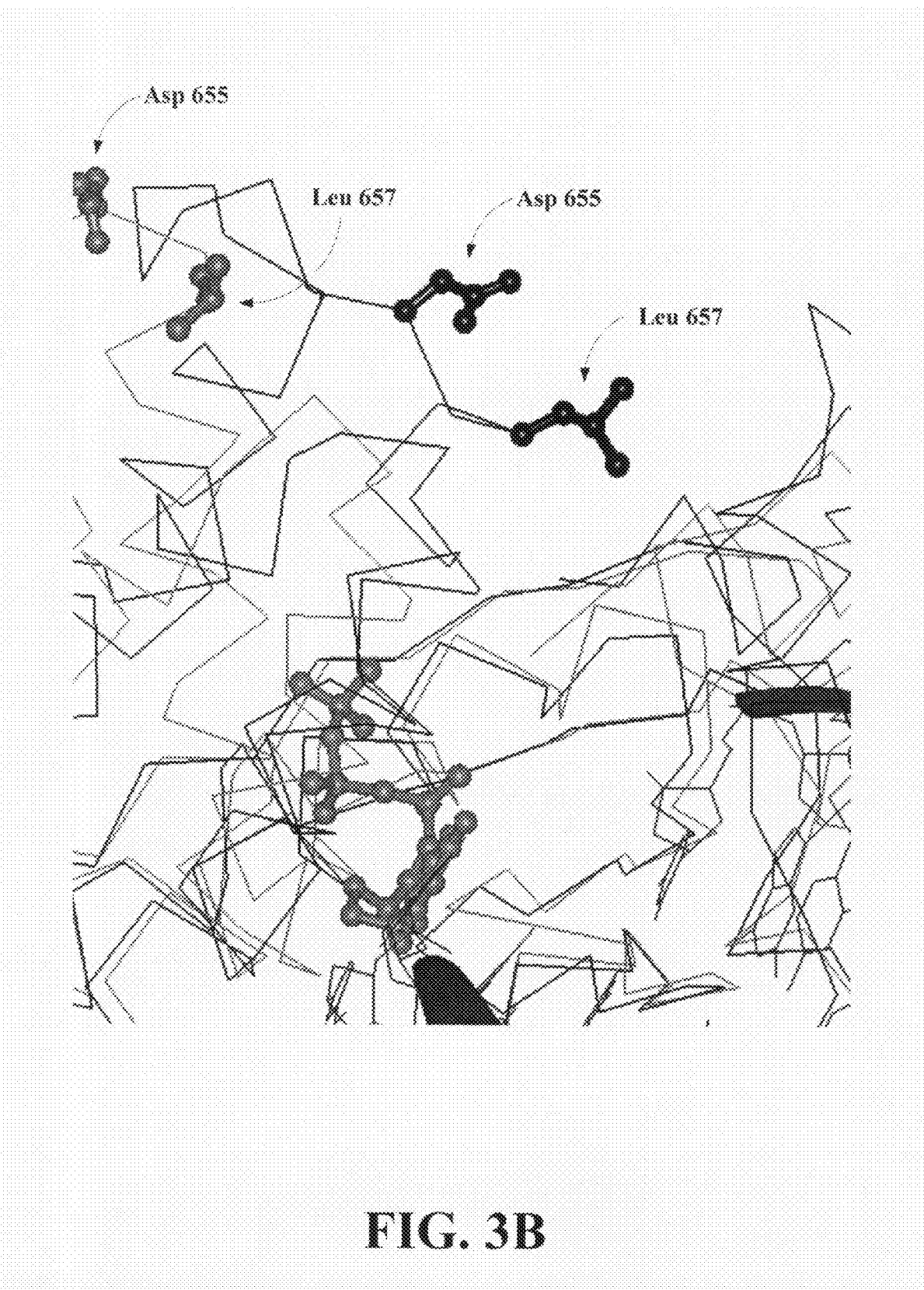
Figure 3C:
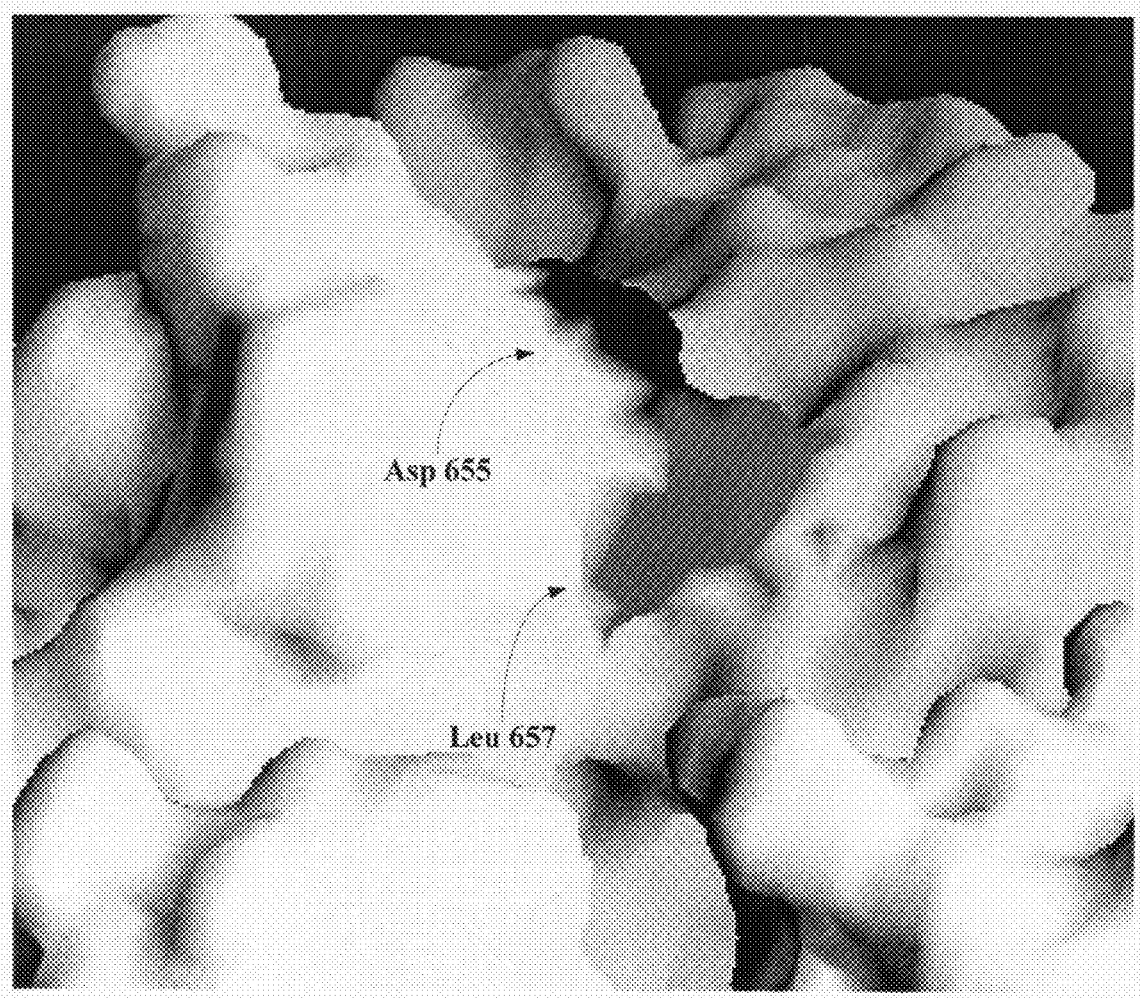

Referring now to FIGS. 3A-C, an overlay between 3ktq (closed 'black') and 1tau (open 'light blue'), the large fragment of Taq DNA polymerase I is shown. Looking at FIG. 3A, the bound DNA from 3ktq is shown in red while the ddCTP bound to 3ktq is in green. Three residues were visually identified as moving the most when the polymerase goes from open (1tau) to closed (3ktq), namely, Asp655, Pro656, and Leu657. Based on further analyses of the structures, Pro656 appears to have the role of capping the O-helix. Leu657's side chain is very close to another part of the protein in the closed (3ktq) form. Addition of a larger side chain/tag is thought to diminish the ability of the polymerase to achieve a fully closed, active conformation. Conversely, Asp655 is entirely solvent exposed in both the closed and open conformations of the polymerase. Looking at FIG. 3B, a close-up view of the active site from the overlay of the 3ktq (closed) and 1tau (open) conformations of Taq polymerase is shown. The large displacements between the open and closed conformations are evident. Looking at FIG. 3C, a close-up view of a molecular surface representation of 3ktq (in the absence of DNA and ddCTP). The molecular surface is colored in two areas, blue for Asp655 and green for Leu657. In this representation, it is evident that Leu657 is in close proximity to another part of the protein, because the green part of the molecular surface, in the thumb domain, is "connected" to a part of the fingers domain. This view shows this region of the polymerase looking into the palm of the hand with fingers to the right and thumb to the left.

Mutagenesis and Sequencing of Polymerase Variants

The gene encoding Taq DNA polymerase was obtained and will be expressed in pTTQ 18 in *E. coli* strain DH1. See, e.g., Engelke et al., 1990. The inventors have identified candidate amino acids for mutagenesis including the amino acids in Tables I-IV, the refined lists or mixtures or combinations thereof. The inventors using standard molecular methods well-known in the art introduced a cysteine codon, individually, at each of target amino acid sites. See, e.g., Sambrook et al., 1989 and Allen et al., 1998. DNA is purified from isolated colonies expressing the mutant polymerase, sequenced using dye-terminator fluorescent chemistry, detected on an ABI PRISM 377 Automated Sequencer, and analyzed using Sequencher™ available from GeneCodes, Inc.

Expression and Purification of Enzyme Variants

The inventors have demonstrated that the Taq polymerase is capable of incorporating γ-tagged dNTPs to synthesize extended DNA sequences. The next step involves the construction of mutants capable of carrying a tag designed to interact with the tags on the dNTPS and optimization of the polymerase for single-molecule sequencing. The mutants are constructed using standard site specific mutagenesis as described above and in the experimental section. The constructs are then inserted into and expressed in *E. coli*. Mutant Taq polymerase is then obtained after sufficient *E. coli* is grown for subsequence polymerase isolation and purification.

Although *E. coli* can be grown to optical densities exceeding 100 by computer-controlled feedback-based supply of non-fermentative substrates, the resulting three kg of *E. coli* cell paste will be excessive during polymerase optimization. Of course, when optimized polymerases construct are prepared, then this large scale production will be used. During the development of optimized polymerases, the mutants are derived from *E. coli* cell masses grown in 10 L well-oxygenated batch cultures using a rich medium available from Amgen. For fast polymerase mutant screening, the mutants are prepared by growing *E. coli* in 2 L baffled shake glasses. Cell paste are then harvested using a 6 L preparative centrifuge, lysed by French press, and cleared of cell debris by centrifugation. To reduce interference from *E. coli* nucleic acid sequences, it is preferably to also remove other nucleic acids. Removal is achieved using either nucleases (and subsequent heat denaturation of the nuclease) or, preferably using a variation of the compaction agent-based nucleic acid precipitation protocol as described in Murphy et al., Nature Biotechnology 17, 822, 1999.

Because the thermal stability of Taq polymerase is considerably greater than typical *E. coli* proteins, purification of Taq polymerase or its mutants from contaminating Taq polymerase proteins is achieved by a simple heat treatment of the crude polymerase at 75° C. for 60 minutes, which reduces *E. coli* protein contamination by approximately 100-fold. This reduction in *E. coli* protein contamination combined with the high initial expression level, produces nearly pure Taq polymerase or its mutants in a convenient initial step; provide, of course, that the mutant polymerase retains the thermal stability of the native polymerase.

For routine sequencing and PCR screening, further limited purification is generally required. A single anion-exchange step, typically on Q Sepharose at pH 8.0, is generally sufficient to produce a product pure enough to these tests. Preferably, a second purification step will also be performed to insure that contamination does not cloud the results of subsequent testing. The second purification step involves SDS-PAGE and CD-monitored melting experiments.

Selection of Site in dNTP to Accept Fluorescent Tag

Molecular docking simulations were carried out to predict the docked orientation of the natural and fluorescently labeled dNTPs using the AutoDock computer program (Morris et al., 1998; Soares et al., 1999). Conformational flexibility is permitted during the docking simulations making use of an efficient Lamarckian Genetic algorithm implemented in the AutoDock program. A subset of protein side chains is also allowed to move to accommodate the dNTP as it docks. The best docked configurations is then energy minimized in the presence of a solvent environment. Experimental data are available which identify amino acids in the polymerase active site that are involved in catalysis and in contact with the template/primer DNA strands or the dNTP to be incorporated. The computer-aided chemical modeling such as docking studies can be used identify and support sites in the dNTP that can be labeled and to predict the FRET efficiency of dNTPs carrying a specific label at a specific site.

In general, the dNTPs are tagged either by reacting a dNTP with a desired tag or by reacting a precursor such as the pyrophosphate group or the base with a desired tag and then completing the synthesis of the DNTP.

Chemical Modification of Nucleotides for DNA Polymerase Reactions

The inventors have developed syntheses for modifying fluorophore and fluorescence energy transfer compounds to have distinct optical properties for differential signal detection, for nucleotide/nucleoside synthons for incorporation of modifications on base, sugar or phosphate backbone positions, and for producing complementary sets of four deoxynucleotide triphosphates (dNTPs) containing substituents on nucleobases, sugar or phosphate backbone.

Synthesis of γ-Phosphate Modified dNTPs

The inventors have found that the native Taq polymerase is capable of polymerizing phosphate-modified dNTPs or ddNTPs. Again, tagging the dNPTs or ddNTPs at the beta and/or gamma phosphate groups is a preferred because the replicated DNA contains no unnatural bases, polymerase activity is not significantly adversely affected and long DNA strands are produced. The inventors have synthesized γ-ANS-phosphate dNTPs, where the ANS is attached to the phosphate through a phosphamide bond. Although these tagged dNTPs are readily incorporated by the native Taq polymerase and by HIV reverse transcriptase, ANS is only one of a wide range of tags that can be attached through either the β and/or γ phosphate groups.

The present invention uses tagged dNTPs or ddNTPs in combination with polymerase for signal detection. The dNTPs are modified at phosphate positions (alpha, beta and/or gamma) and/or other positions of nucleotides through a covalent bond or affinity association. The tags are designed to be removed from the base before the next monomer is added to the sequence. One method for removing the tag is to place the tag on the gamma and/or beta phosphates. The tag is removed as pyrophosphate dissociates from the growing DNA sequence. Another method is to attach the tag to a position of on the monomer through a cleavable bond. The tag is then removed after incorporation and before the next monomer incorporation cleaving the cleavable bond using light, a chemical bond cleaving reagent in the polymerization medium, and/or heat.

One generalized synthetic routine to synthesizing other γ-tagged dNTPs is given below:

where FR is a fluorescent tag, L is a linker group, X is either H or a counterion depending on the pH of the reaction medium, Z is a group capable of reaction with the hydroxyl group of the pyrophosphate and Z' is group after reaction with the dNMP. Preferably, Z is Cl, Br, I, OH, SH, $NH_2$, NHR, $CO_2H$, $CO_2R$, SiOH, SiOR, GeCH, GeOR, or similar reactive functional groups, where R is an alkyl, aryl, aralkyl, alkaryl, halogenated analogs thereof or hetero atom analogs thereof and Z' is O, NH, NR, $CO_2$, SiO, GeO, where R is an alkyl, aryl, aralkyl, alkaryl, halogenated analogs thereof or hetero atom analogs thereof.

The synthesis involves reacting Z terminated fluorescent tag, FR-L-Z with a pyrophosphate group, $P_2O_6X_3H$, in DCC and dichloromethane to produce a fluorescent tagged pyrophosphate. After the fluorescent tagged pyrophosphate is prepared, it is reacted with a morpholine terminated dNMP in acidic THF to produce a dNTP having a fluorescent tag on its γ-phosphate. Because the final reaction bears a fluorescent tag and is larger than starting materials, separation from unmodified starting material and tagged pyrophosphate is straight forward.

A generalized synthesis of a the FR-L group is shown below:

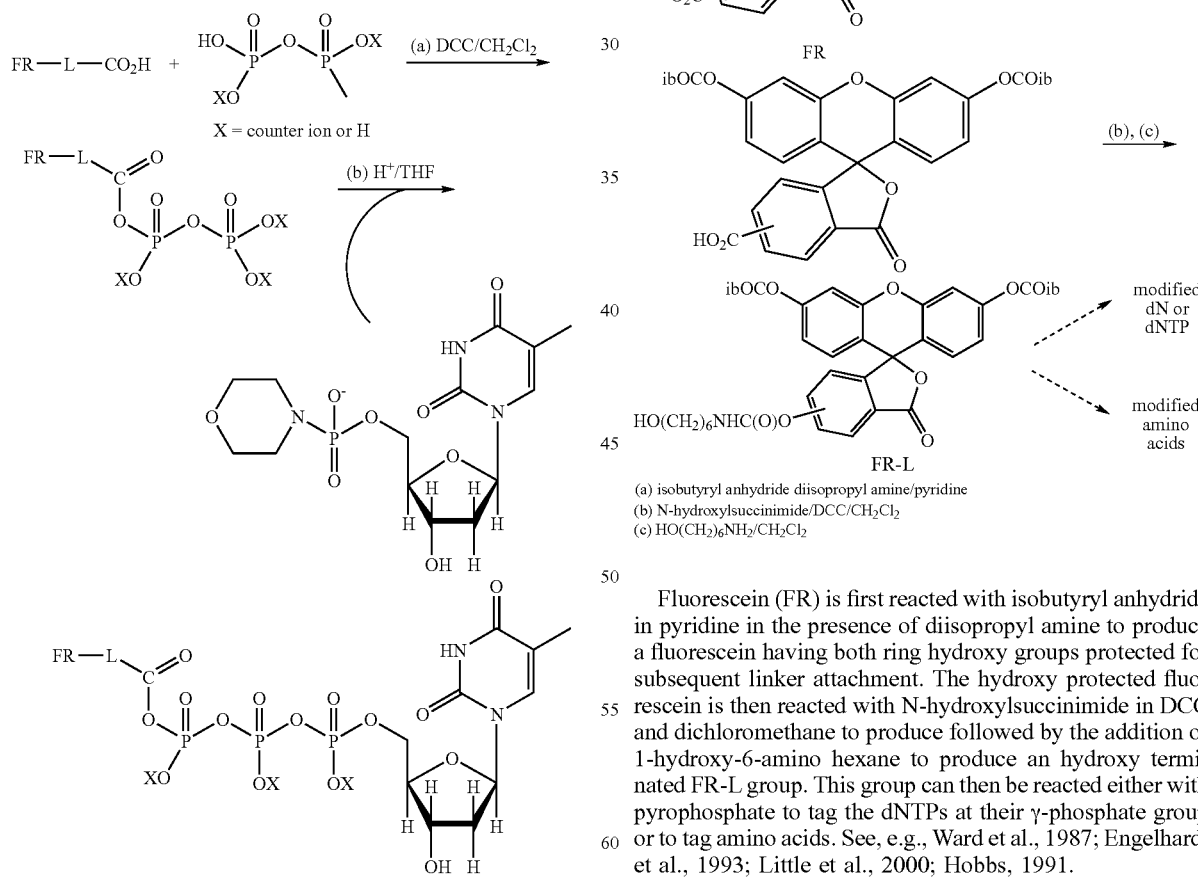

(a) isobutyryl anhydride diisopropyl amine/pyridine
(b) N-hydroxylsuccinimide/DCC/$CH_2Cl_2$
(c) HO($CH_2$)$_6$$NH_2$/$CH_2Cl_2$ Fluorescein (FR) is first reacted with isobutyryl anhydride in pyridine in the presence of diisopropyl amine to produce a fluorescein having both ring hydroxy groups protected for subsequent linker attachment. The hydroxy protected fluorescein is then reacted with N-hydroxylsuccinimide in DCC and dichloromethane to produce followed by the addition of 1-hydroxy-6-amino hexane to produce an hydroxy terminated FR-L group. This group can then be reacted either with pyrophosphate to tag the dNTPs at their γ-phosphate group or to tag amino acids. See, e.g., Ward et al., 1987; Engelhardt et al., 1993; Little et al., 2000; Hobbs, 1991.

By using different fluorescent tags on each dNTP, tags can be designed so that each tag emits a distinguishable emission spectra. The emission spectra can be distinguished by producing tags with non-overlapping emission frequencies—multicolor—or each tag can have a non-overlapping spectral feature such a unique emission band, a unique absorption band and/or a unique intensity feature. System that use a distinguishable tag on each dNTP improves confidence values associated with the base calling algorithm.

The synthetic scheme shown above for fluorescein is adaptable to other dyes as well such as tetrachlorofluorescein (JOE) or N,N,N',N'-tetramethyl-6-carboxyrhodamine (TAMRA). Typically, the gamma phosphate tagged reactions are carried out in basic aqueous solutions and a carbodiimide, such as DEC. Other fluorophore molecules and dNTPs can be similarly modified.

Synthesis of dNTP Tagged at on the Base

Although tagging the dNTPs at the beta and/or gamma phosphate is preferred, the dNTPs can also be tagged on the base and/or sugar moieties while maintaining their polymerase reaction activity. The sites for modifications are preferably selected to not interfere with Watson-Crick base pairing. A generalized scheme for base modification is shown below:

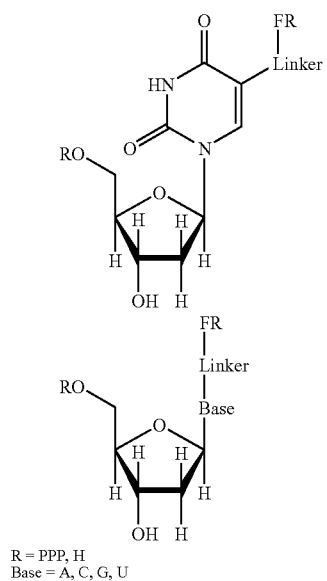

R = PPP, H
Base = A, C, G, U

Polymerase Activity Assays Using a Fluorescently-tagged Enzyme

The activities of polymerase variants are monitored throughout polymerase development. Polymerase activity is assayed after a candidate amino acid is mutated to cysteine and after fluorescent tagging of the cysteine. The assay used to monitor the ability of the native Taq polymerase to incorporate fluorescently-tagged dNTPs is also used to screen polymerase variants. Since the mutant Taq polymerases have altered amino acid sequences, the assays provide mutant characterization data such as thermostability, fidelity, polymerization rate, affinity for modified versus natural bases.

Mutant Taq polymerase activity assays are carried out under conditions similar to those used to examine the incorporation of fluorescently-tagged dNTPs into DNA polymers by the native Taq polymerase. To examine mutant Taq polymerase activity, the purified mutant Taq polymerase is incubated in polymerase reaction buffer with a $5'$-$^{32}$P end-labeled primer/single-stranded template duplex, and appropriate tagged dNTP(s). The polymerase's ability to incorporate a fluorescently-tagged dNTP is monitored by assaying the relative amount of fluorescence associated with the extended primer on either an ABI377 DNA Sequencer (for fluorescently tagged bases), a Fuji BAS1000 phosphorimaging system, or other appropriate or similar detectors or detection systems. This assay is used to confirm that the mutant polymerase incorporates tagged dNTP and to confirm that fluorescent signatures are obtained during base incorporation. These assays use an end-labeled primer, the fluorescently-tagged dNTP and the appropriate base beyond the fluorescent tag. The products are then size separated and analyzed for extension. Reactions are either performed under constant temperature reaction conditions or thermocycled, as necessary.

Primer Extension Assays

The ability of Taq DNA polymerase to incorporate a γ-phosphate dNTP variant is assayed using conditions similar to those developed to examine single base incorporation by a fluorescently-tagged DNA polymerase. See, e.g. Furey et al., 1998. These experiments demonstrate that polymerases bearing a fluorescent tag do not a priori have reduced polymerization activity. The inventors have demonstrated that the native Taq polymerase incorporates γ-tagged dNTP, singly or collectively to produce long DNA chains.

To examine polymerase activity, the polymerase is incubated in polymerase reaction buffer such as Taq DNA polymerase buffer available from Promega Corporation of Madison, Wis. with either a $5'$-$^{32}$P or a fluorescently end-labeled primer (TOP)/single-stranded template (BOT-'X') duplex, and appropriate dNTP(s) as shown in Table V. Reactions are carried out either at constant temperature or thermocycled, as desired or as is necessary. Reaction products are then size-separated and quantified using a phosphorimaging or fluorescent detection system. The relative efficiency of incorporation for each tagged DNTP is determined by comparison with its natural counterpart.

TABLE V

```
Primer Strand:

TOP 5'      GGT ACT AAG CGG CCG CAT G 3'      (SEQ ID NO. 1)

Template Strands:

BOT-T 3'    CCA TGA TTC GCC GGC GTA CTC 5'    (SEQ ID NO. 2)

BOT-C 3'    CCA TGA TTC GCC GGC GTA CCC 5'    (SEQ ID NO. 3)

BOT-G 3'    CCA TGA TTC GCC GGC GTA CGC 5'    (SEQ ID NO. 4)
```

TABLE V-continued

| | | |
|---|---|---|
| BOT-A 3' | CCA TGA TTC GCC GGC GTA CAC 5' | (SEQ ID NO. 5) |
| BOT-3T 3' | CCA TGA TTC GCC GGC GTA CTT TC 5' | (SEQ ID NO. 6) |
| BOT-Sau 3' | CCA TGA TTC GCC GGC GTA CCT AG 5' | (SEQ ID NO. 7) |

In Table V, 'TOP' represents the primer strand of an assay DNA duplex. Variants of the template strand are represented by 'BOT'. The relevant feature of the DNA template is indicated after the hyphen. For example, BOT-T, BOT-C, BOT-G, BOT-A are used to monitor polymerase incorporation efficiency and fidelity for either nucleotides or nucleotide variants of dA, dG, dC, and dT, respectively.

Preliminary assays are performed prior to exhaustive purification of the tagged dNTP to ensure that the polymerase is not inhibited by a chemical that co-purifies with the tagged dNTP, using the 'BOT-Sau' template. The 'BOT-Sau' template was designed to monitor incorporation of natural dGTP prior to tagged dATP (i.e., a positive control for polymerase activity). More extensive purification is then performed for promising tagged nucleotides. Similarly, experiments are carried out to determine whether the polymerase continues extension following incorporation of the tagged dNTPs, individually or collectively, using the same end-labeled 'TOP' primer, the appropriate 'BOT' primer, the fluorescently-tagged dNTP, and the appropriate base 3' of the tagged nucleotide. The products are then size-separated and analyzed to determine the relative extension efficiency.

Assay Fidelity of γ-phosphate Tagged Nucleotide Incorporation

The Taq DNA polymerase lacks 3' to 5' exonuclease activity (proofreading activity). If the polymerase used in single-molecule DNA sequencing possessed a 3' to 5' exonuclease activity, the polymerase would be capable of adding another base to replace one that would be removed by the proofreading activity. This newly added base would produce a signature fluorescent signal evidencing the incorporation of an additional base in the template, resulting in a misidentified DNA sequence, a situation that would render the single-molecule sequencing systems of this invention problematic.

If the error rate for the incorporation of modified dNTPs exceeds a threshold level of about 1 error in 100, the sequencing reactions are preferably run in parallel, with the optimal number required to produce sequence information with a high degree of confidence for each base call determined by the error rate. Larger error rates require more parallel run, while smaller error rates require fewer parallel runs. In fact, if the error rate is low enough, generally less than 1 error in 1,000, preferably 1 error in 5,000 and particularly 1 error in 10,000 incorporated base, then no parallel runs are required. Insertions or deletions are, potentially, more serious types of errors and warrant a minimal redundancy of 3 repeats per sample. If 2 reactions were run, one could not be certain which was correct. Thus, 3 reactions are needed for the high quality data produced by this system.

The BOT-variant templates are used to characterize the accuracy at which each γ-tagged dNTP is incorporated by an engineered polymerase as set forth in Table V. Oligonucleotides serve as DNA templates, and each differing only in the identity of the first base incorporated. Experiments using these templates are used to examine the relative incorporation efficiency of each base and the ability of the polymerase to discriminate between the tagged dNTPs. Initially, experiments with polymerase variants are carried out using relatively simple-sequence, single-stranded DNA templates. A wide array of sequence-characterized templates is available from the University of Houston in Dr. Hardin's laboratory, including a resource of over 300 purified templates. For example, one series of templates contains variable length polyA or polyT sequences. Additional defined-sequence templates are constructed as necessary, facilitating the development of the base-calling algorithms.

Relative Fluorescence Intensity Assays

Direct detection of polymerase action on the tagged dNTP is obtained by solution fluorescence measurements, using SPEX 212 instrument or similar instrument. This instrument was used to successfully detect fluorescent signals from ANS tagged γ-phosphate dNTPs, being incorporated by Taq polymerase at nanomolar concentration levels. The SPEX 212 instrument includes a 450 watt xenon arc source, dual emission and dual excitation monochromators, cooled PMT (recently upgraded to simultaneous T-format anisotropy data collection), and a Hi-Tech stopped-flow accessory. This instrument is capable of detecting an increase in fluorescence intensity and/or change in absorption spectra upon liberation of the tagged pyrophosphate from ANS tagged γ-phosphate dNTPs, as was verified for ANS-pyrophosphate released by Taq and RNA polymerase and venom phosphodiesterase.

Experiments have been and are being performed by incubating γ-phosphate tagged dATP or TTP (Control: non-modified dATP and TTP) in an appropriate buffer (e.g., buffers available from Promega Corporation) in the presence of polymerase (Control: no enzyme) and DNA primer/template [poly(dA). poly(dT)] (Control: no primer/template DNA). When the polymerase incorporates a tagged dNTP, changes in fluorescence intensity and/or frequency, absorption and/or emission spectra, and DNA polymer concentration are detected. Changes in these measurables as a function of time and/or temperature for experimental versus control cuvettes allows for unambiguous determination of whether a polymerase is incorporating the γ-phosphate tagged dNTP. Excitation and fluorescence emission can be optimized for each tagged dNTP based on changes in these measurables.

Development of a Single-Molecule Detection System

The detection of fluorescence from single molecules is preferably carried out using microscopy. Confocal-scanning microscopy can be used in this application, but a non-scanning approach is preferred. An microscope useful for detecting fluorescent signals due to polymerase activity include any type of microscope, with oil-immersion type microscopes being preferred. The microscopes are preferably located in an environment in which vibration and temperature variations are controlled, and fitted with a highly-sensitive digital camera. While many different cameras can be to record the fluorescent signals, the preferred cameras are intensified CCD type cameras such as the iPentaMax from Princeton Instruments.

The method of detection involves illuminating the samples at wavelengths sufficient to induce fluorescence of the tags, preferably in an internal-reflection format. If the fluorescent tags are a donor-acceptor pair, then the excitation frequency must be sufficient to excite the donor. Although any type of light source can be used, the preferred light source is a laser. It will often be advantageous to image the same sample in multiple fluorescence emission wavelengths, either in rapid succession or simultaneously. For simultaneous multi-color imaging, an image splitter is preferred to allow the same CCD to collect all of the color images simultaneously. Alternatively, multiple cameras can be used, each viewing the sample through emission optical filters of different wavelength specificity.

Tag detection in practice, of course, depends upon many variables including the specific tag used as well electrical, fluorescent, chemical, physical, electrochemical, mass isotope, or other properties. Single-molecule fluorescence imaging is obtainable employing a research-grade Nikon Diaphot TMD inverted epifluorescence microscope, upgraded with laser illumination and a more-sensitive camera. Moreover, single-molecule technology is a well-developed and commercially available technology. See, e.g., Peck et al., 1989; Ambrose et al., 1994; Goodwin et al., 1997; Brouwer et al., 1999; Castro and Williams, 1997; Davis et al., 1991; Davis et al., 1992; Goodwin et al., 1997; Keller et al., 1996; Michaelis et al., 2000; Orrit and Bernard, 1990; Orrit et al., 1994; Sauer et al., 1999; Unger et al., 1999; Zhuang et al., 2000.

The epifluorescence microscope can be retrofitted for evanescent-wave excitation using an argon ion laser at 488 nm. The inventors have previously used this illumination geometry in assays for nucleic acid hybridization studies. The existing setup has also been upgraded by replacement of the current CCD camera with a 12-bit 512×512 pixel Princeton Instruments I-PentaMAX generation IV intensified CCD camera, which has been used successfully in a variety of similar single-molecule applications. This camera achieves a quantum efficiency of over 45% in the entire range of emission wavelengths of the dyes to be used, and considerably beyond this range. The vertical alignment of their existing microscope tends to minimize vibration problems, and the instrument is currently mounted on an anti-vibration table.

A preferred high-sensitivity imaging system is based on an Olympus IX70-S8F inverted epifluorescence microscope. The system incorporates low-background components and enables capture of single molecule fluorescence images at rates of greater than 80 frames per second with quantum efficiency between 60-70% in the range of emission wavelengths of the fluorescently active tags.

In imaging the fluorescence of multiple single molecules, it is preferable to minimize the occurrence of multiple fluorescent emitters within a data collection channel such as a single pixel or pixel-bin of the viewing field of the CCD or other digital imaging system. A finite number of data collection channels such as pixels are available in any given digital imaging apparatus. Randomly-spaced, densely-positioned fluorescent emitters generally produce an increased fraction of pixels or pixel bins that are multiply-occupied and problematic in data analysis. As the density of emitters in the viewing field increases so does the number of problematic data channels. While multiple occupancy of distinguishable data collection regions within the viewing field can be reduced by reducing the concentration of emitters in the viewing field, this decrease in concentration of emitters increases the fraction of data collection channels or pixels that see no emitter at all, therefore, leading to inefficient data collection.

A preferred method for increasing and/or maximizing the data collection efficiency involves controlling the spacing between emitters (tagged polymerase molecules). This spacing is achieved in a number of ways. First, the polymerases can be immobilized on a substrate so that only a single polymerase is localized within each data collection channel or pixel region within the viewing field of the imaging system. The immobilization is accomplished by anchoring a capture agent or linking group chemically attached to the substrate. Capture or linking agents can be spaced to useful distances by choosing inherently large capture agents, by conjugating them with or bonding them to molecules which enhance their steric bulk or electrostatic repulsion bulk, or by immobilizing under conditions chosen to maximize repulsion between polymerizing molecular assembly (e.g., low ionic strength to maximize electrostatic repulsion).

Alternatively, the polymerase can be associated with associated proteins that increase the steric bulk of the polymerase or the electrostatic repulsion bulk of the polymerizing system so that each polymerizing molecular assembly cannot approach any closer than a distance greater than the data channel resolution size of the imaging system.

Polymerase Activity Assays Using a Single-Molecule Detection System

These assays are performed essentially as described in for polymerase activity assays described herein. As stated above, the primary difference between assaying polymerase activity for screening purposes involves the immobilization of some part of the polymerizing assembly such as the polymerase, target DNA or a primer associated protein to a solid support to enable viewing of individual replication events. A variety of immobilization options are available, including, without limitation, covalent and/or non-covalent attachment of one of the molecular assemblies on a surface such as an organic surface, an inorganic surface, in or on a nanotubes or other similar nano-structures and/or in or on porous matrices. These immobilization techniques are designed to provide specific areas for detection of the detectable property such as fluorescent, NMR, or the like, where the spacing is sufficient to decrease or minimize data collection channels having multiple emitters. Thus, a preferred data collection method for single-molecule sequencing is to ensure that the fluorescently tagged polymerases are spaced apart within the viewing field of the imagining apparatus so that each data collection channel sees the activity of only a single polymerase.

Analysis of Fluorescent Signals from Single-molecule Sequencing System

The raw data generated by the detector represents between one to four time-dependent fluorescence data streams comprising wavelengths and intensities: one data stream for each fluorescently labeled base being monitored. Assignment of base identities and reliabilities are calculated using the PHRED computer program. If needed, the inventors will write computer programs to interpret the data streams having partial and overlapping data. In such cases, multiple experiments are run so that confidence limits are assigned to each base identity according to the variation in the reliability indices and the difficulties associated with assembling stretches of sequence from fragments. The reliability indices represent the goodness of the fit between the observed wavelengths and intensities of fluorescence compared with ideal values. The result of the signal analyses is a linear DNA sequence with associated probabilities of certainty. Additionally, when required, the data is stored in a database for dynamic querying for identification and comparison purposes. A search term (sequence) of 6-10, 11-16, 17-20, 21-30 bases can be compared against reference sequences to quickly identify perfectly matched sequences or those sharing a user defined level of identity. Multiple experiments are run so that confidence limits can be assigned to each base identity according to the variation in the reliability indices and the difficulties associated with assembling stretches of sequence from fragments. The reliability indices represent the goodness of the fit between the observed wavelengths and intensities of fluorescence compared with the ideal values. The result of the signal analyses is a linear DNA sequence with associated probabilities of certainty.

Informatics: Analysis of Fluorescent Signals from the Single-Molecule Detection System Data collection allows data to be assembled from partial information to obtain sequence information from multiple polymerase molecules in order to determine the overall sequence of the template or target molecule. An important driving force for convolving together results obtained with multiple single-molecules is the impossibility of obtaining data from a single molecule over an indefinite period of time. At a typical dye photobleaching efficiency of $2*10^{-5}$, a typical dye molecule is expected to undergo 50,000 excitation/emission cycles before permanent photobleaching. Data collection from a given molecule may also be interrupted by intersystem crossing to an optically inactive (on the time scales of interest) triplet state. Even with precautions against photobleaching, therefore, data obtained from any given molecule is necessarily fragmentary for template sequences of substantial length, and these subsequences are co-processed in order to derive the overall sequence of a target DNA molecule.

Additionally, in certain instances it is useful to perform reactions with reference controls, similar to microarray assays. Comparison of signal(s) between the reference sequence and the test sample are used to identify differences and similarities in sequences or sequence composition. Such reactions can be used for fast screening of DNA polymers to determine degrees of homololgy between the polymers, to determine polymorphisms in DNA polymers, or to identity pathogens.

EXAMPLES

Cloning and Mutagenesis of Taq Polymerase

Cloning

Bacteriophage lambda host strain Charon 35 harboring the full-length of the *Thermus aquaticus* gene encoding DNA polymerase I (Taq pol I) was obtained from the American Type Culture Collection (ATCC; Manassas, Va.). Taq pol I was amplified directly from the lysate of the infected *E. coli* host using the following DNA oligonucleotide primers:

```
Taq Pol I forward                (SEQ ID NO. 8)
5'-gc gaattc atgaggggga tgctgcccct ctttgagccc-3'

Taq Pol I reverse                (SEQ ID NO. 9)
5'-gc gaattc accctccttgg cggagcgc cagtcctccc-3'
```

The underlined segment of each synthetic DNA oligonucleotide represents engineered EcoRI restriction sites immediately preceding and following the Taq pol I gene. PCR amplification using the reverse primer described above and the following forward primer created an additional construct with an N-terminal deletion of the gene:

```
Taq Pol I_A293_trunk             (SEQ ID NO. 10)
5'-aatccatgggccctggaggaggc ccctggccccgc-3'
```

The underlined segment corresponds to an engineered NcoI restriction site with the first codon encoding for an alanine (ATG start representing an expression vector following the ribosome binding site). Ideally, the full-length and truncated constructs of the Taq pol I gene is ligated to a single EcoRI site (full-length) and in an NcoI/EcoRI digested pRSET-b expression vector. *E. coli* strain JM109 is used as host for all in vivo manipulation of the engineered vectors.

Mutagenesis

Once a suitable construct is generated, individual cysteine mutations are introduced at preferred amino acid positions including positions 513-518, 643, 647, 649 and 653-661 of the native Taq polymerase having the following amino acid sequence:

```
  1 mrgmlplfep kgrvllvdgh hlayrtfhal kglttsrgep vgavvgfaks llkalkedgd 61 avivvfdaka psfrheaygg ykagraptpe dfprqlalik elvdllglar levpgyeadd 121 vlaslakkae kegyevrilt adkdlyglls drihvlhpeg ylitpawlwe kyglrpdqwa 181 dyraltgdes dnlpgvkgig ektarkllee wgsleallkn ldrlkpaire kilahmddlk 241 lswdlakvrt dlplevdfak rrepdrerlr aflerlefgs llhefglles pkaleeapwp 301 ppegafvgfv lsrkepmwad llalaaargg rvhrapepyk alrdlkearg llakdlsvla 361 lreglglppg ddpmllayll dpsnttpegv arryggewte eageraalse rlfanlwgrl 421 egeerllwly reverplsav lahmeatgvr ldvaylrals levaeeiarl eaevfrlagh 481 pfnlnsrdql ervlfdelgl paigktektg krstsaavle alreahpive kilgyreltk 541 lkstyidplp dlihprtgrl htrfngtata tgrlsssdpn lqnipvrtpl ggrirrafia 601 eegwllvald vsqielrvla hlsgdenlir vfqegrdiht etaswmfgvp reavdplmrr
```

-continued
```
661 aaktinfgvl ygmsahrlsq elaipyeeaq afieryfqsf pkvrawiekt leegrrrqyv 721 etlfgrrryv pdlearvksv reaaermafn mpvggtaadl mklamvklfp rleemgarml 781 lgvhdelvle apkeraeava rlakevmegv vplavpleve vgigedwlsa ke(SEQ ID NO.11)
```

The following amino acid residues correspond to the amino acids between amino acid 643 and 661, where xxx represents intervening amino acid residues in the native polymerase:

```
                                          (SEQ ID NO. 12)
643-Ala xxx xxx xxx Phe xxx Val xxx xxx Glu Ala
Val Asp Pro Leu Met Arg Arg Ala -661.
```

Overlapping primers are used to introduce point mutations into the native gene by PCR based mutagenesis (using Pfu DNA polymerase).

Complementary forward and reverse primers each contain a codon that encodes the desired mutated amino acid residue. PCR using these primers results in a knicked, non-methylated, double-stranded plasmid containing the desired mutation. To remove the template DNA, the entire PCR product is treated with DpnI restriction enzyme (cuts at methylated guanosines in the sequence GATC). Following digestion of the template plasmid, the mutated plasmid is transformed and ligation occurs in vivo.

The following synthetic DNA oligonucleotide primers are used for mutagenesis as described below, where the letters designated in lowercase have been modified to yield the desired Cysteine substitution at the indicated position. Mutants are then screened via automated sequencing.

```
Alanine 643 to Cysteine Replacement
Taq Pol I_Ala643Cys_fwd         (SEQ ID NO. 13)
5'-C CAC ACG GAG ACC tgC AGC TGG ATG TTC GGC G-3'

Taq Pol I_Ala643Cys_rev         (SEQ ID NO. 14)
5'-C GCC GAA CAT CCA CGA Gca GGT CTC CGT GTG G-3'

Phenylalanine 647 to Cysteine Replacement
Taq Pol I_Phe647Cys_fwd         (SEQ ID NO. 15)
5'-CC GCC AGC TGG ATG TgC GGC GTC CCC CGG GAG GC
G-3'

Taq Pol I_Phe647Cys_rev         (SEQ ID NO. 16)
5'-GGC CTC CCG GGG GAC GCC GcA CAT CCA CGT GGC G
G-3'

Valine 649 to Cysteine Replacement
Taq Pol I_Val649Cys_fwd         (SEQ ID NO. 17)
5'-GCC AGC TGG ATG TTC GGC tgC CCC CGG GAG GCC GTG
G-3'

Taq Pol I_Val649Cys_rev         (SEQ ID NO. 18)
5'-C CAC GGC CTC CCG GGG Gca GCC GAA CAT CCA GCT
GGC-3'

Glutamic Acid 652 to Cysteine Replacement
Taq Pol I_Glu652Cys_fwd         (SEQ ID NO. 19)
5'-GGC GTC CCC CGG tgc CCC GTG GAG CCC CTG ATG CG
C-3'

Taq Pol I_Glu652Cys_rev         (SEQ ID NO. 20)
5'-GCG CAT CAG GGG GTC CAC GGC gca CCG GGG GAG GC
C-3'

Alanine 653 to Cysteine Replacement
Taq Pol I_Ala653Cys_fwd         (SEQ ID NO. 21)
5'-GGC GTC CCC CGG GAG tgC GTG GAG CCC CTG ATG CG
C-3'

Taq Pol I_Ala653Cys_rev         (SEQ ID NO. 22)
5'-GCG CAT CAG GGG GTC GAG Gca CTC CCG GGG GAG GC
C-3'

Valine 654 to Cysteine Replacement
Taq Pol I_Val654Cys_fwd         (SEQ ID NO. 23)
5'-GTC CCC CGG GAG GCC tgt GAC CCC CTG ATG CGC-3'

Taq Pol I_Val654Cys_rev         (SEQ ID NO. 24)
5'-GCG CAT CAG GGG GTC aca GGC CTC CCG GGG GAC-3'

Aspartic Acid 655 to Cysteine Replacement
Taq Pol I_D655C_fwd             (SEQ ID NO. 25)
5'-CCC CGG GAG GCC GTG tgC CCC CTG ATG CGC CGG-3'

Taq Pol I_D655C_rev             (SEQ ID NO. 26)
5'-CCG GCG CAT CAG GGG Gca CAC GGC CTC CCG GGG-3'

Proline 656 to Cysteine Replacement
Taq Pol I_Pro656Cys_fwd         (SEQ ID NO. 27)
5-CGG GAG GCC GTG GAC tgC CTG ATG CGC CGG GCG-3'

Taq Pol I_Pro656Cys_rev         (SEQ ID NO. 28)
5'-CGC CCG GCG CAT CAG Gca GTC CAC GGC CTC CCG-3'

Leucine 657 to Cysteine Replacement
Taq Pol I_Leu657Cys_fwd         (SEQ ID NO. 29)
5'-GCC GTG GAC CCC tgc ATG CGC CGG GCG GCC-3'

Taq Pol I_Leu657Cys_rev         (SEQ ID NO. 30)
5'-GGC CGC CCG GCG CAT gca GGG GTC CAC GGC-3'

Methionine 658 to Cysteine Replacement
Taq Pol I_Met658Cys_fwd         (SEQ ID NO. 31)
5'-GCC GTG GAG CCC CTG tgt CGC CGG GCG GCC-3'

Taq Pol I_Met658Cys_rev         (SEQ ID NO. 32)
5'-GGC CGG CCG GCG aca CAG GGG GTC CAC GGC-3'

Arginine 659 to Cysteine Replacement
Taq Pol I_Arg659Cys_fwd         (SEQ ID NO. 33)
5'-GCC GTG GAC CCC CTG ATG tgC CGG GCG GCC AAG AC
C-3'

Taq Pol I _Arg659Cys_rev        (SEQ ID NO. 34)
5'-GGT CTT GGC CGG CCG GCa CAT GAG GGG GTC CAC GG
C-3'

Arginine 660 to Cysteine Replacement
Taq Pol I_Arg660Cys_fwd         (SEQ ID NO. 35)
5'-GAC CCC CTG ATG CGG tGc GCG GCC AAG ACC ATC-3'

Taq Pol I_Arg660Cys_rev         (SEQ ID NO. 36)
5'-GAT GGT CTT GGC CGC gCa GCG CAT CAG GGG GTC-3'

Alanine 661 to Cysteine Replacement
Taq Pol I_Ala661Cys_fwd         (SEQ ID NO. 37)
5'-CCC CTG ATG CGC CGG tgc CCC AAG ACC ATC AAC-3'

Taq Pol I_Ala661Cys_rev         (SEQ ID NO. 38)
5'-GTT GAT GGT CTT GGC gca CCG GCG CAT CAG GGG-3'
```

The resulting mutant Taq polymerases are then reacted with a desired atomic or molecular tag to tag the cysteine in the mutant structure through the SH group of the cysteine residue and screened for native and/or tagged dNTP incorporation and incorporation efficiency. The mutant polymerases are also screened for fluorescent activity during base incorporation. Thus, the present invention also relates to mutant Taq polymerase having a cysteine residue added one or more of the sites selected from the group consisting of 513-518, 643, 647, 649 and 653-661. After cysteine replacement and verification of polymerase activity using the modified dNTPs, the mutant Taq polymerases are reacted with a tag through the SH group of the inserted cysteine residue. The resulting amino acid replacement for the positions 513-518. 643. 647. 649 and 653-661:

```
Cys Ser Trp Met Phe Gly Val Pro Arg Glu Ala Val Asp Pro Leu Met   (SEQ ID NO. 39)
643 644 645 646 647 648 649 650 651 652 653 654 655 656 657 658

Arg Arg Ala
659 660 661

Ala Ser Trp Met Cys Gly Val Pro Arg Glu Ala Val Asp Pro Leu Met   (SEQ ID NO. 40)
643 644 645 646 647 648 649 650 651 652 653 654 655 656 657 658

Arg Arg Ala
659 660 661

Ala Ser Trp Met Phe Gly Cys Pro Arg Glu Ala Val Asp Pro Leu Met   (SEQ ID NO. 41)
643 644 645 646 647 648 649 650 651 652 653 654 655 656 657 658

Arg Arg Ala
659 660 661

Ala Ser Trp Met Phe Gly Val Pro Arg Cys Ala Val Asp Pro Leu Met   (SEQ ID NO. 42)
643 644 645 646 647 648 649 650 651 652 653 654 655 656 657 658

Arg Arg Ala
659 660 661

Ala Ser Trp Met Phe Gly Val Pro Arg Glu Cys Val Asp Pro Leu Met   (SEQ ID NO. 43)
643 644 645 646 647 648 649 650 651 652 653 654 655 656 657 658

Arg Arg Ala
659 660 661

Ala Ser Trp Met Phe Gly Val Pro Arg Glu Ala Cys Asp Pro Leu Met   (SEQ ID NO. 44)
643 644 645 646 647 648 649 650 651 652 653 654 655 656 657 658

Arg Arg Ala
659 660 661

Ala Ser Trp Met Phe Gly Val Pro Arg Glu Ala Val Cys Pro Leu Met   (SEQ ID NO. 45)
643 644 645 646 647 648 649 650 651 652 653 654 655 656 657 658

Arg Arg Ala
659 660 661

Ala Ser Trp Met Phe Gly Val Pro Arg Glu Ala Val Asp Cys Leu Met   (SEQ ID NO. 46)
643 644 645 646 647 648 649 650 651 652 653 654 655 656 657 658

Arg Arg Ala
659 660 661

Ala Ser Trp Met Phe Gly Val Pro Arg Glu Ala Val Asp Pro Cys Met   (SEQ ID NO. 47)
643 644 645 646 647 648 649 650 651 652 653 654 655 656 657 658

Arg Arg Ala

Ala Ser Trp Met Phe Gly Val Pro Arg Glu Ala Val Asp Pro Leu Cys   (SEQ ID NO. 48)
643 644 645 646 647 648 649 650 651 652 653 654 655 656 657 658

Arg Arg Ala
659 660 661

Ala Ser Trp Met Phe Gly Val Pro Arg Glu Ala Val Asp Pro Leu Met   (SEQ ID NO. 49)
643 644 645 646 647 648 649 650 651 652 653 654 655 656 657 658

Cys Arg Ala
659 660 661

Ala Ser Trp Met Phe Gly Val Pro Arg Glu Ala Val Asp Pro Leu Met   (SEQ ID NO. 50)
643 644 645 646 647 648 649 650 651 652 653 654 655 656 657 658

Arg Cys Ala
659 660 661
```

```
                                          -continued
Ala Ser Trp Met Phe Gly Val Pro Arg Glu Ala Val Asp Pro Leu Met    (SEQ ID NO. 51)
643 644 645 646 647 648 649 650 651 652 653 654 655 656 657 658

Arg Arg Cys
659 660 661

Cys Thr Ser Ala Ala Val                                            (SEQ ID NO. 52)
513 514 515 516 517 518

Ser Cys Ser Ala Ala Val                                            (SEQ ID NO. 53)
513 514 515 516 517 518

Ser Thr Cys Ala Ala Val                                            (SEQ ID NO. 54)
513 514 515 516 517 518

Ser Thr Ser Cys Ala Val                                            (SEQ ID NO. 55)
513 514 515 516 517 518

Ser Thr Ser Ala Cys Val                                            (SEQ ID NO. 56)
513 514 515 516 517 518

Ser Thr Ser Ala Ala Cys                                            (SEQ ID NO. 57)
513 514 515 516 517 518
```

Synthesis of Modified dNTPs

Synthesis of (γ-AmNS)dATP

Nucleotide analogues which contain fluorophore 1-aminonaphalene-5-sulfonate attached to the γ-phosphate bond were synthesized (*J. Biol. Chem.* 254, 12069-12073, 1979). DATP analog—(γ-AmNS)dATP was synthesized according to the procedures slightly altered from what was described by Yarbrough and co-workers for (γ-AmNS)ATP with some modifications.

Figure 4:
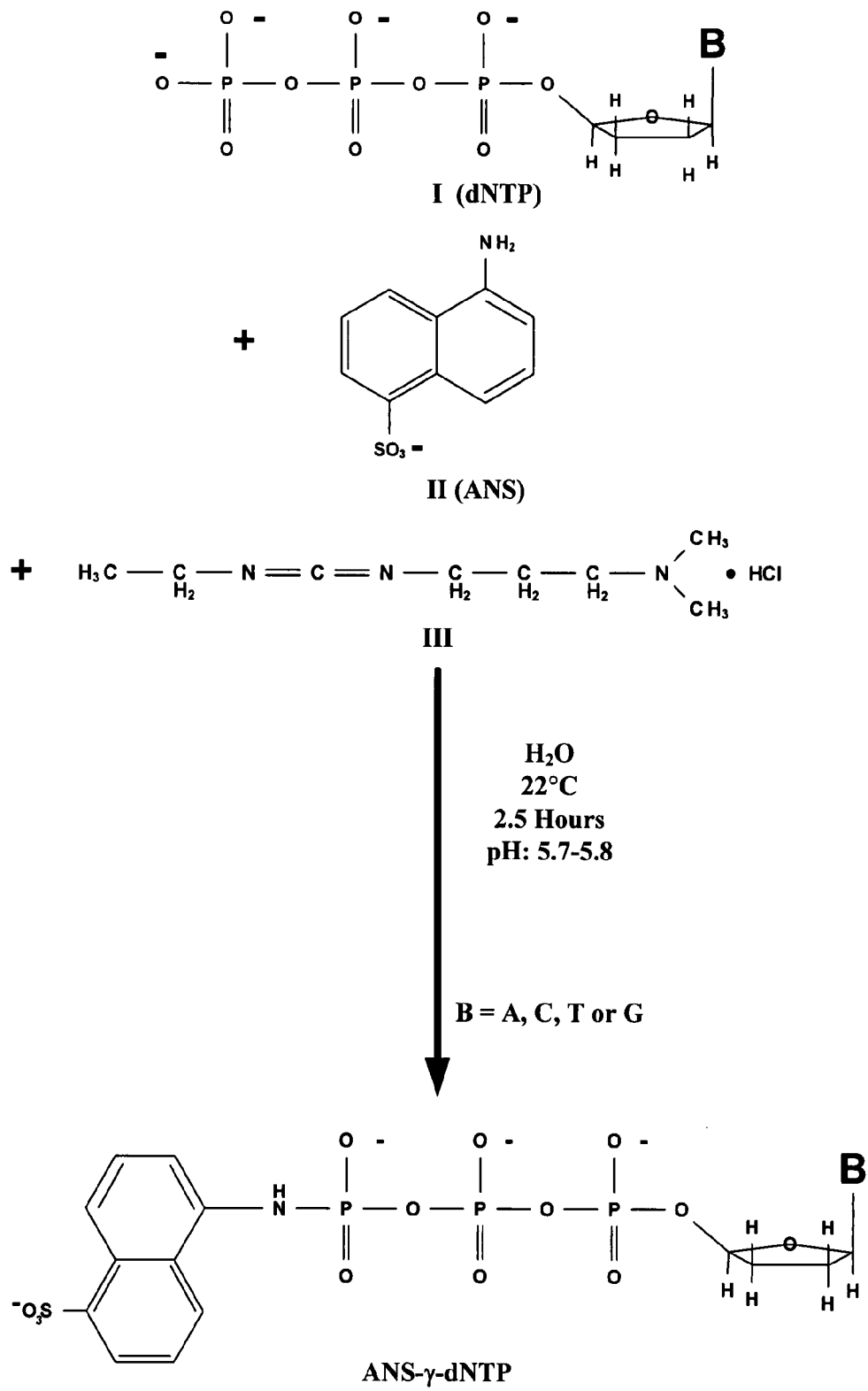
FIG. 4 depicts an image of a 20% denaturing polyacrylamide gel containing size separated radiolabeled products from DNA extension experiments involving γ-ANS-phosphate-dATP.

This example illustrates the preparation of gamma ANS tagged dATP, shown graphically in FIG. 4.

1-Aminonaphthalene-5-sulphonic acid (447 mg, 2 mmol, 40 eq., from Lancaster) was added to 10 mL of $H_2O$, and the pH was adjusted to 5.8 with 1 N NaOH. The insoluble material was removed by syringe filter, yielding a solution which was essentially saturated for this pH value (~0.18 to 0.2 M). 4 mL of 12.5 mM 5'triphosphate-2'-deoxyadenosine disodium salt (0.05 mmol, 1 eq.) and 2 mL of 1 M 1-(3-dimethylaminopropyl)-3-ethyl-carbodiimide hydrochloride (DEC, 2 mmol, 40 eq., from Lancaster) were added to a reaction vessel at 22° C. The reaction was initiated by adding 10 mL of the 1-aminonaphthalene-5-sulfonate solution and allowed to continue for 2.5 h. The pH was kept between 5.65-5.75 by periodic addition of 0.1 N HCl. After 2.5 h, the reaction was diluted to 50 mL and adjusted to a solution of 0.05 M triethylammonium bicarbonate buffer (TEAB, pH~7.5). The reaction product was chromatographed on a 50 mL DEAE-SEPHADEX ion exchanger (A-25-120) column at low temperature that was equilibrated with ~pH 7.5 1.0 M aqueous TEAB (100 mL), 1.0 M aqueous sodium bicarbonate (100 mL), and ~pH 7.5, 0.05 M aqueous TEAB (100 mL). The column was eluted with a linear gradient of ~pH 7.5 aqueous TEAB from 0.05 to 0.9 M. Approximately 10 mL fractions were collected. Absorbance and fluorescence profiles (UV 366 nm) of the fractions were obtained after appropriate dilution. The fluorescent fraction eluted at ~0.7 M buffer after the peak of the unreacted dATP and showed a brilliant blue fluorescence. The product-containing fractions were pooled, dried by lyophilizer and co-evaporated twice with $H_2O$/ethanol (70/30). The residue was taken up in water and lyophilized. $^{31}P$ NMR ($^1H$ decoupled, 600 MHz, $D_2O$, $Me_3PO4$ external reference, 293 K, pH 6.1) δ (ppm) −12.60, −14.10, −25.79. The reference compound dATP gave the following resonance peaks: $^{31}P$ NMR (dATP, $Na^+$) in $D_2O$ 293 K, δ (ppm) −11.53 (γ), −13.92 (α), −24.93 (β).

Using diode array UV detection HPLC, the fraction containing the desired product was easily identified by the distinct absorption of the ANS group at 366 nm. Additionally, $^{31}P$ NMR spectra were recorded for the γ-phosphate tagged dATP and regular dATP in an aqueous solution. For each compound, three characteristic resonances were observed, confirming the triphosphate moiety in the γ-tagged dATP. The combined analyses—$^1H$-NMR, HPLC, and UV spectra—provide supporting information for the formation of the correct compound.

The same synthetic procedure was used to prepare γ-ANS-phosphate modified dGTP, dTTP and dCTP.

γ-Phosphate-tagged dNTP Incorporation by Taq Polymerase

The following examples illustrate that commercially available Taq DNA polymerase efficiently incorporates the ANS-γ-phosphate dNTPs, the syntheses and characterization as described above.

In the first example, illustrates the incorporation of ANS-γ-phosphate dATP to produce extended DNA products from primer templates. The reactions were carried out in extension buffer and the resulting Radiolabeled products were size separated on a 20% denaturing polyacrylamide gel. Data was collected using a phosphorimaging system. Referring now the FIG. 13, Lane 1 contains 5' radiolabeled 'TOP' probe in extension buffer. Lane 2 contains Taq DNA polymerase, 50 μM dGTP incubated with a DNA duplex (radiolabeled TOP with excess 'BOT-Sau'). Lane 3 contains Taq DNA polymerase, 50 μM dATP incubated with a DNA duplex (radiolabeled TOP with excess 'BOT-Sau'). Lane 4 contains Taq DNA polymerase, 50 μM ANS-γ-dATP incubated with a DNA duplex (radiolabeled TOP with excess 'BOT-Sau'). Lane 5 contains Taq DNA polymerase, 50 μM dGTP incubated with a DNA duplex (radio labeled TOP with excess 'BOT-T'). Lane 6 contains spill-over from lane 5. Lane 7 contains Taq DNA polymerase, 50 μM dATP incubated with a DNA duplex (radiolabeled TOP with excess 'BOT-T'). Lane 8 contains Taq DNA polymerase, 50 μM ANS-γ-dATP incubated with a DNA duplex (radiolabeled TOP with excess 'BOT-T'). Lane 9 contains Taq DNA polymerase, 50 μM dGTP incubated with a DNA duplex (radiolabeled TOP with excess 'BOT-3T'). Lane 10 contains Taq DNA polymerase, 50 μM dATP incubated with a DNA duplex (radiolabeled TOP with excess 'BOT-3T'). Lane 11 contains Taq DNA polymerase, ANS-γ-dATP incubated with a DNA duplex (radiolabeled TOP with excess 'BOT-3T'). Lane 12 contains 5' radiolabeled 'TOP' probe in extension buffer. Lane 13 contains 5' radiolabeled 'TOP' probe and Taq DNA polymerase in extension buffer. Oligonucleotide sequences are shown in Table V.

Quantitative comparison of lane 1 with lane 4 demonstrates that very little non-specific, single-base extension was detected when ANS-γ-dATP was included in the reaction, but the first incorporated base should be dGTP (which was not added to the reaction). Quantitative analysis of lanes 1 and 8 demonstrates that approximately 71% of the TOP primer are extended by a template-directed single base when ANS-γ-dATP was included in the reaction and the first incorporated base should be DATP. Thus, Taq DNA polymerase incorporates γ-tagged nucleotides. Equally important to the polymerase's ability to incorporate a γ-tagged nucleotide is its ability to extend the DNA polymer after the modified dATP was incorporated. Comparison of lane 1 with lane 11 demonstrated that a DNA strand was extended after a γ-tagged nucleotide was incorporated. Thus, incorporation of a modified nucleotide was not detrimental to polymerase activity. Note, too, that extension of the primer strand by incorporation of an ANS-γ-nucleotide depended upon Watson-Crick base-pairing rules. In fact, the fidelity of nucleotide incorporation was increased at least 15-fold by the addition of this tag to the γ-phosphate.

This next example illustrates the synthesis of extended DNA polymers using all four ANS tagged γ-phosphate dNTPs. Products generated in these reactions were separated on a 20% denaturing polyacrylamide gel, the gel was dried and imaged following overnight exposure to a Fuji BAS1000 imaging plate. Referring now to FIG. 14, an image of (A) the actual gel, (B) a lightened phosphorimage and (C)) an enhanced phosphorimage. Lane descriptions for A, B, and C follow: Lane 1 is the control containing purified 10-base primer extended to 11 and 12 bases by template-mediated addition of alpha-$^{32}$P dCTP. Lane 2 includes the same primer that was incubated with double-stranded plasmid DNA at 96° C. for 3 minutes (to denature template), the reaction was brought to 37° C. (to anneal primer-template), Taq DNA polymerase and all four natural dNTPs (100 µM, each) were added and the reaction was incubated at 37° C. for 60 minutes. Lane 3 includes the same labeled primer that was incubated with double-stranded DNA plasmid at 96° C. for 3 minutes, the reaction was DNA polymerase and all four gamma-modified dNTPs (100 µM, each) were added and the reaction was incubated at 37° C. for 60 minutes. Lane 4 includes the control, purified 10-base primer that was extended to 11 and 12 bases by the addition of alpha-$^{32}$P-dCTP was cycled in parallel with lanes 5-8 reactions. Lane 5 includes the same $^{32}$P-labeled primer that was incubated with double-stranded plasmid DNA at 96° C. for 3 minutes, the reaction was brought to 37° C. for 10 minutes, during which time Taq DNA polymerase and all four natural dNTPs (100 µM, each) were added. The reaction was cycled 25 times at 96° C. for 10 seconds, 37° C. for 1 minute, and 70° C. for 5 minutes. Lane 6 includes the same $^{32}$P-labeled primer that was incubated with double-stranded plasmid DNA at 96° C. for 3 minutes, the reaction was brought to 37° C. for 10 minutes, during which time Taq DNA polymerase and all four gamma-modified dNTPs (100 µM, each) were added. The reaction was cycled 25 times at 96° C. for 10 seconds, 370C for 1 minute, and 70° C. for 5 minutes. Lane 7 includes nonpurified, 10-base, $^{32}$P-labeled primer that was incubated with double-stranded DNA plasmid at 96° C. for 3 minutes, the reaction was brought to 37° C. for 10 minutes, during which time Taq DNA polymerase and all four natural dNTPs (100 µM, each) were added. The reaction was cycled 25 times at 96° C. for 10 seconds, 37° C. for 1 minute, and 700C for 5 minutes. Lane 8 includes nonpurified, 10-base, $^{32}$P-labeled primer that was incubated with double-stranded DNA plasmid at 96° C. for 3 minutes, the reaction was brought to 37° C. for 10 minutes, during which time Taq DNA polymerase and all four gamma-modified dNTPs were added. The reaction was cycled 25 times at 96° C. for 10 seconds, 37° C. for 1 minute, and 700C for 5 minutes. Evident in the reactions involving tagged dNTPs is a substantial decrease in pyrophosphorolysis as compared to reactions involving natural nucleotides.

This next example illustrates the synthesis of long DNA polymers using all four ANS tagged γ-phosphate dNTPs. Each primer extension reaction was split into two fractions, and one fraction was electrophoresed through a 20% denaturing gel (as described above), while the other was electrophoresed through a 6% denaturing gel to better estimate product lengths. The gel was dried and imaged (overnight) to a Fuji BAS1000 imaging plate. Referring now to FIG. 15, an image of (A) the actual gel, (B) a lightened phosphorimage of the actual gel, and (C)) an enhanced phosphorimage of the actual gel. Lane descriptions for A, B, and C follow: Lane 1 includes 123 Marker with size standards indicated at the left of each panel. Lane 2 contains the control, purified 10-base primer extended to 11 and 12 bases by template-mediated addition of alpha-$^{32}$P dCTP. Lane 3 contains the same $^{32}$P-labeled primer that was incubated with double-stranded plasmid DNA at 96° C. for 3 minutes (to denature template), the reaction was brought to 37° C. (to anneal primer-template), Taq DNA polymerase and all four natural dNTPs (100 µM, each) were added and the reaction was incubated at 37° C. for 60 minutes. Lane 4 includes the same $^{32}$P-labeled primer that was incubated with double-stranded DNA plasmid at 96° C. for 3 minutes, the reaction was brought to 37° C., Taq DNA polymerase and all four gamma-modified dNTPs (100 µM, each) were added and the reaction was incubated at 37° C. for 60 minutes. Lane 5 includes the control, purified 10-base primer that was extended to 11 and 12 bases by the addition of alpha-$^{32}$P-dCTP was cycled in parallel with lanes 5-8 reactions. Lane 6 includes the same $^{32}$P-labeled primer that was incubated with double-stranded plasmid DNA at 96° C. for 3 minutes, the reaction was brought to 37° C. for 10 minutes, during which time Taq DNA polymerase and all four natural dNTPs (100 µM, each) were added. The reaction was cycled 25 times at 96° C. for 10 seconds, 37° C. for 1 minute, and 70° C. for 5 minutes. Lane 7 includes the same $^{32}$P-labeled primer that was incubated with double-stranded plasmid DNA at 96° C. for 3 minutes, the reaction was brought to 37° C. for 10 minutes, during which time Taq DNA polymerase and all four gamma-modified dNTPs (100 µM, each) were added. The reaction was cycled 25 times at 96° C. for 10 seconds, 37° C. for 1 minute, and 70° C. for 5 minutes. Lane 8 includes nonpurified, 10-base, $^{32}$P-labeled primer that was incubated with double-stranded DNA plasmid at 96° C. for 3 minutes, the reaction was brought to 37° C. for 10 minutes, during which time Taq DNA polymerase and all four natural dNTPs (100 µM, each) were added. The reaction was cycled 25 times at 96° C. for 10 seconds, 37° C. for 1 minute, and 700C for 5 minutes. Lane 9 includes nonpurified, 10-base, $^{32}$P-labeled primer that was incubated with double-stranded DNA plasmid at 96° C. for 3 minutes, the reaction was brought to 37° C. for 10 minutes, during which time Taq DNA polymerase and all four gamma-modified dNTPs were added. The reaction was cycled 25 times at 96° C. for 10 seconds, 37° C. for 1 minute, and 70° C. for 5 minutes.

The majority of extension products in this reaction are several hundred bases long for both natural and γ-modified dNTPs, and a significant percentage of these products are too large to enter the gel. Thus, demonstrating the gamma phosphate tagged dNTPs are used by Taq polymerase to generate long DNA polymers that are non-tagged or native DNA polymer chains.

Different Polymerases React Differently to the Gamma-Modified Nucleotides

The indicated enzyme (Taq DNA Polymerase, Sequenase, HIV-1 Reverse Transcriptase, T7 DNA Polymerase, Klenow Fragment, Pfu DNA Polymerase) were incubated in the manufacturers suggested reaction buffer, 50 μM of the indicated nucleotide at 37° C. for 30-60 minutes, and the reaction products were analyzed by size separation through a 20% denaturing gel.

Figure 5:
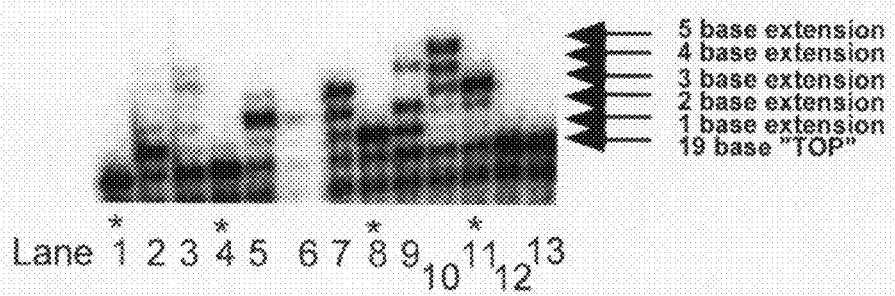
FIG. 5 depicts an image of (A) the actual gel, (B) a lightened phosphorimage and (C) an enhanced phosphorimage of products generated in DNA extension reactions using γ-ANS-phosphate-dNTPs.
Figure 6:
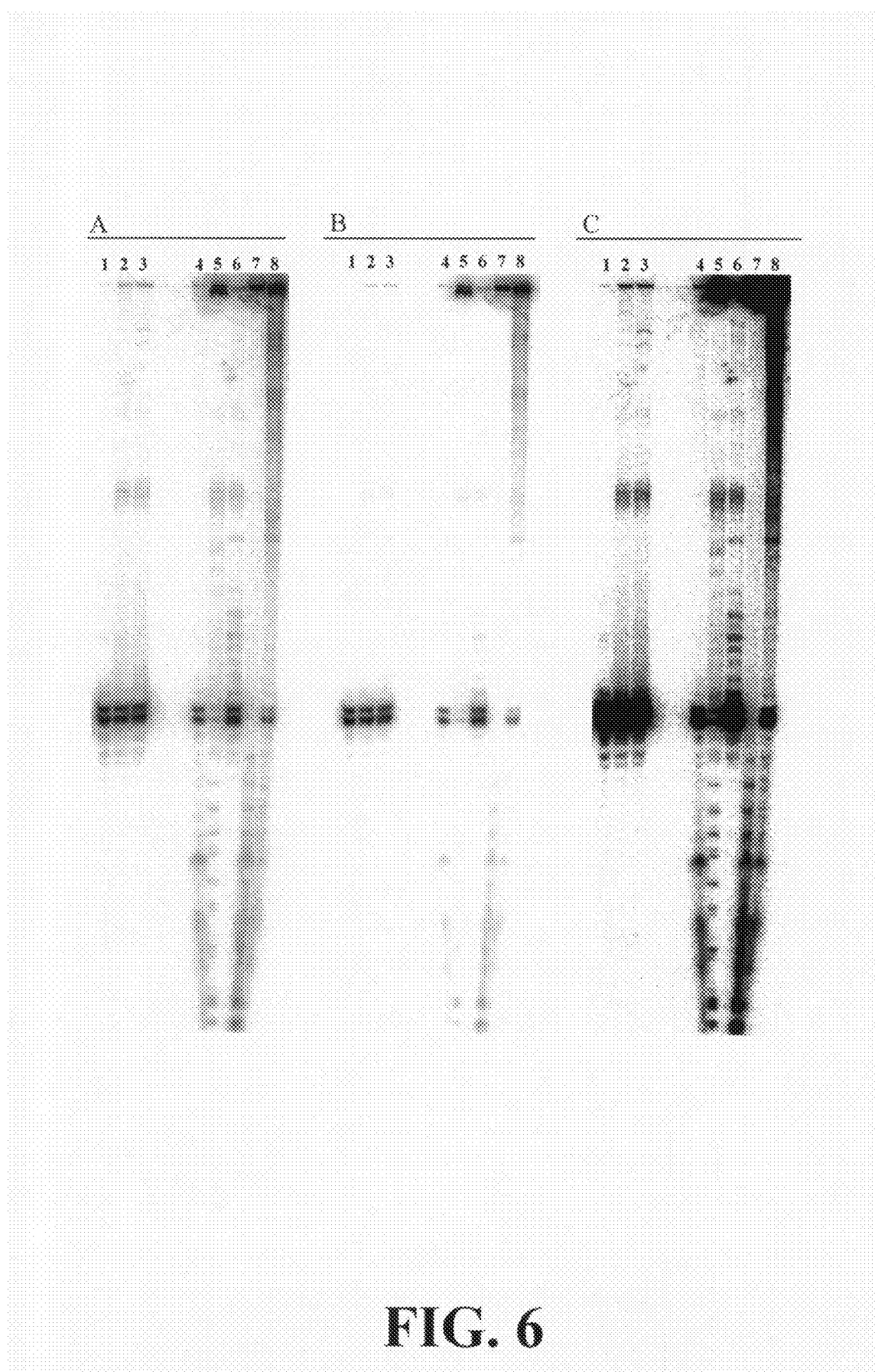
FIG. 6 depicts an image of (A) 6% denaturing polyacrylamide gel, (B) a lightened phosphorimage of the actual gel, and (C) an enhanced phosphorimage of the actual gel containing products generated in DNA extension reactions using γ-ANS-phosphate-dNTPs.
Figure 7:
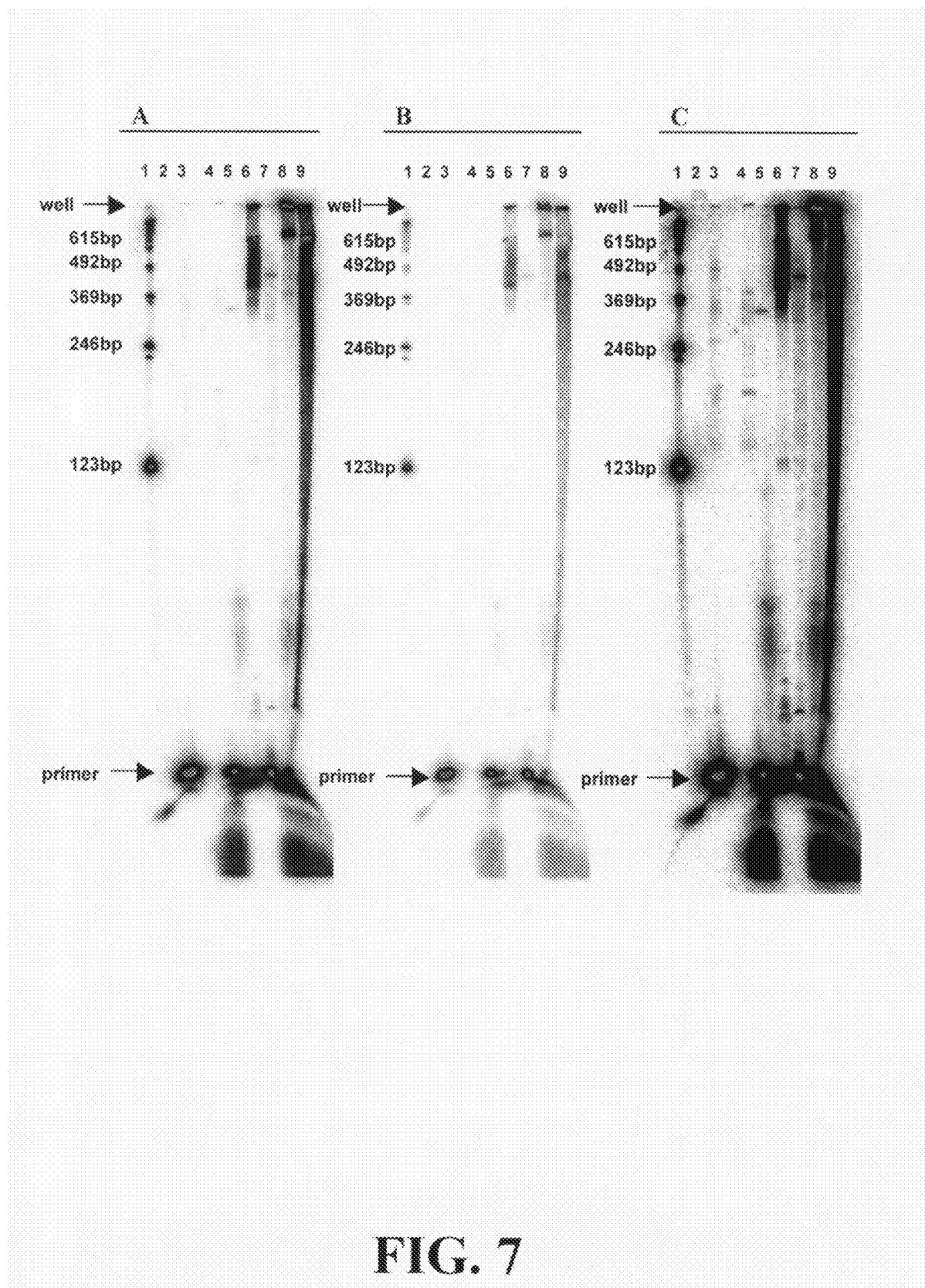
FIG. 7 depicts an image of (A) the actual gel, (B) a lightened phosphorimage of the actual gel, and (C) an enhanced phosphorimage of the actual gel.

Taq DNA polymerase efficiently uses the gamma-modified nucleotides to synthesize extended DNA polymers at increased accuracy as shown in FIG. 4-6.

Figure 8:
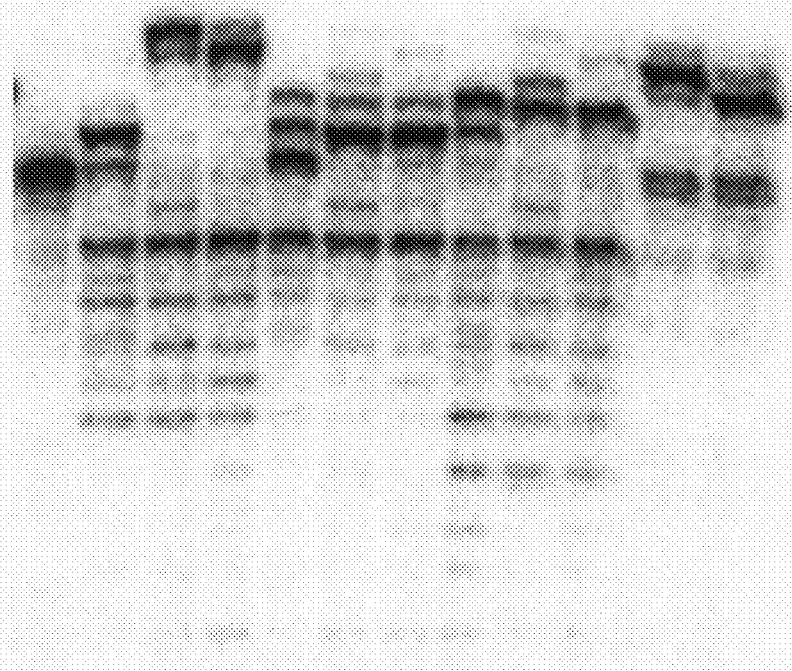
FIG. 8 depicts data for the Klenow fragment from *E. coli* DNA polymerase I incorporation of gamma-modified nucleotides.

The Klenow fragment from *E. coli* DNA polymerase I efficiently uses the gamma-modified nucleotides, but does not exhibit the extreme fidelity improvements observed with other enzymes as shown in FIG. 8.

Figure 9:
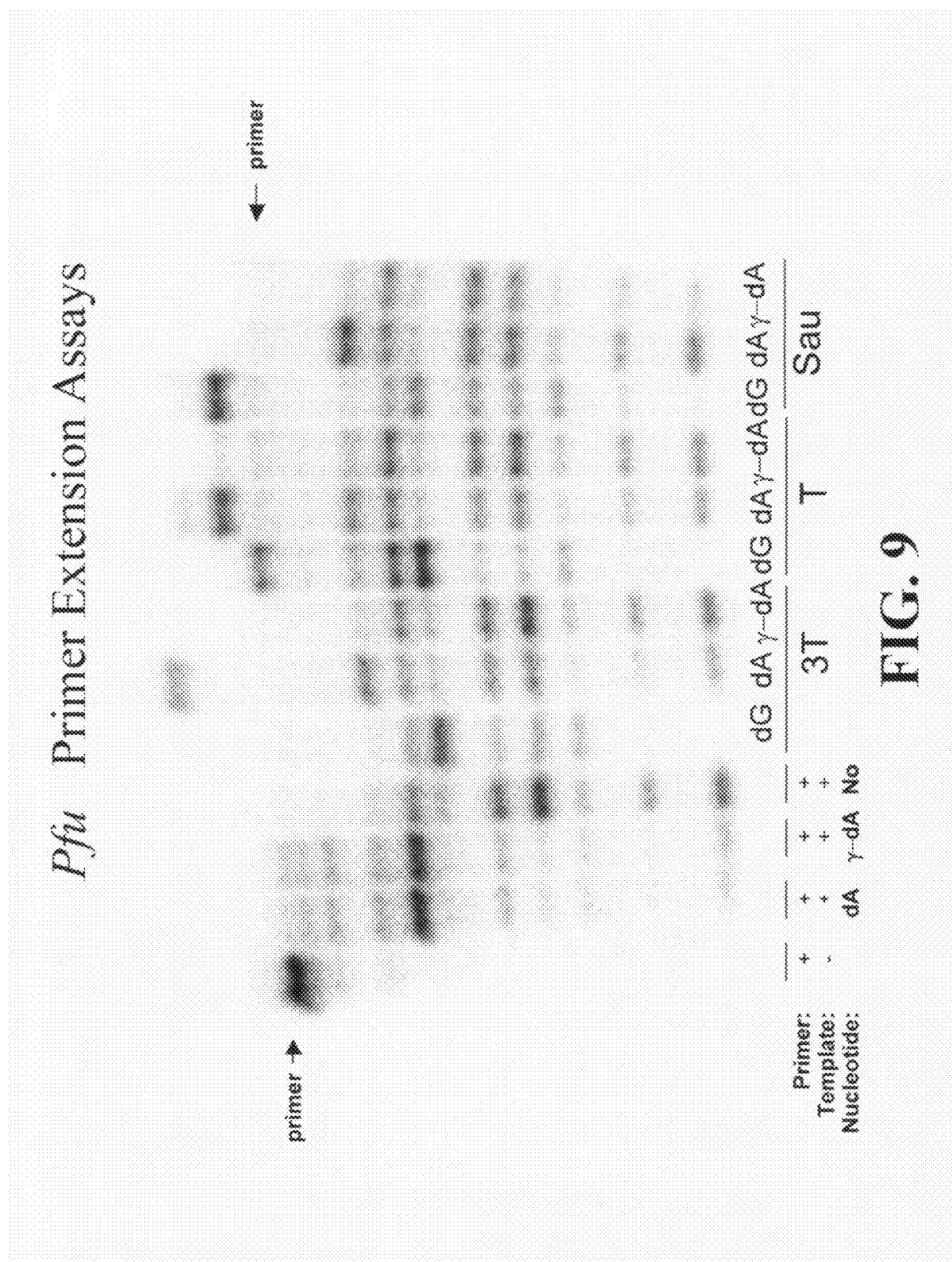
FIG. 9 depicts data for the Pfu DNA polymerase incorporation of gamma-modified nucleotides.

Pfu DNA polymerase does not efficiently use gamma-modified nucleotides and is, thus, not a preferred enzyme for the single-molecule sequencing system as shown in FIG. 9.

Figure 10:
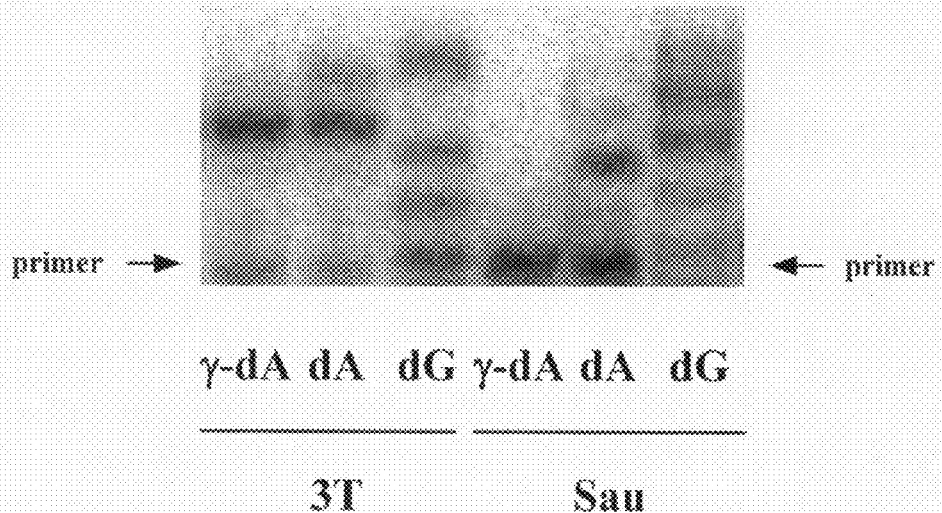
FIG. 10 depicts data for the HIV-1 reverse transcriptase incorporation of gamma-tagged nucleotides.

HIV-1 reverse transcriptase efficiently uses the gamma-tagged nucleotides, and significant fidelity improvement results as shown in FIG. 10.

Figure 11:
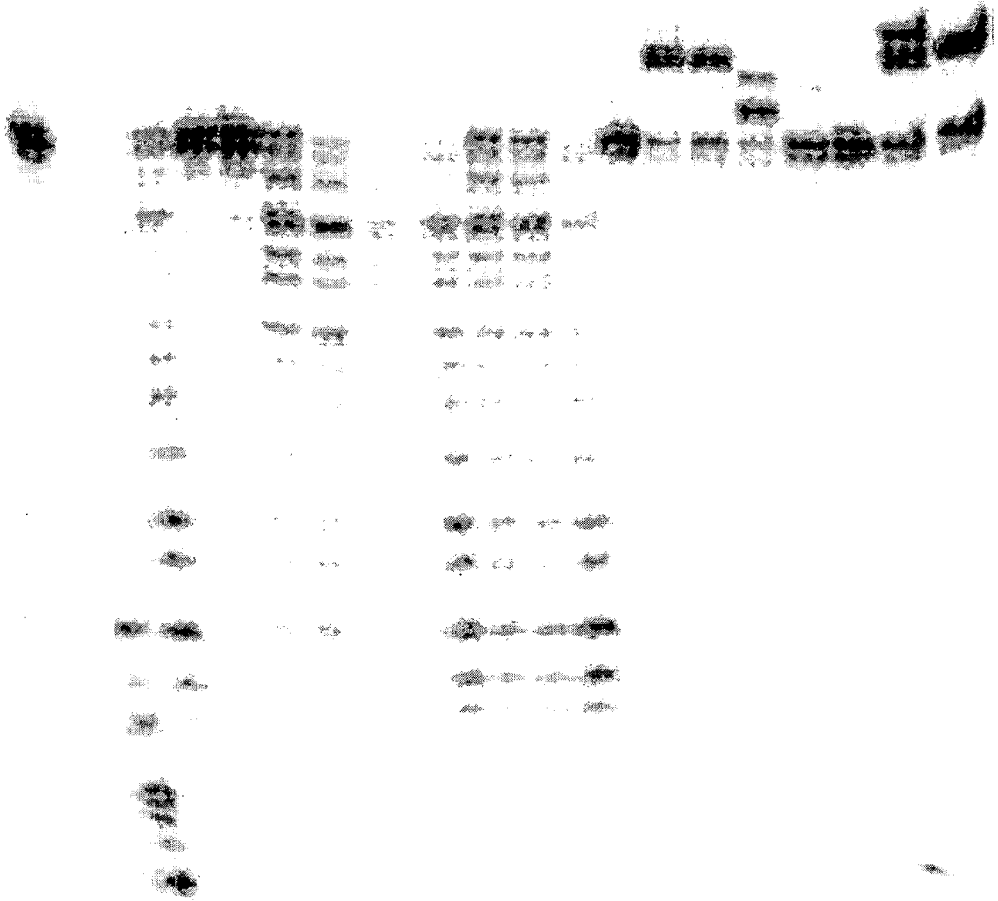
FIG. 11 depicts experimental results for native T7 DNA polymerase and Sequenase incorporation of gamma-tagged nucleotides.

Polymerization activity is difficult to detect in the reaction products generated by native T7 DNA polymerase (due to the presence of the enzymes exonuclease activity). However, its genetically modified derivative, Sequenase, shows that the gamma-modified nucleotides are efficiently incorporated, and that incorporation fidelity is improved, relative to non-modified nucleotides. The experimental results for native T7 DNA polymerase and Sequenase are shown in FIG. 11.

Thus, for the Taq polymerase or the HIV1 reverse transcriptase, improved fidelity, due to the use of the gamma-modified dNTPs of this invention, enables single-molecule DNA sequencing. However, not all polymerases equally utilize the gamma-modified nucleotides of this invention, specifically, Klenow, Sequenase, HIV-1 reverse transcriptase and Taq polymerases incorporate the modified nucleotides of this invention, while the Pfu DNA polymerase does not appear to incorporate the modified nucleotides of this invention.

Improved PCR—Generation of Long DNA Sequences

The fidelity of nucleic acid synthesis is a limiting factor in achieving amplification of long target molecules using PCR. The misincorporation of nucleotides during the synthesis of primer extension products limits the length of target that can be efficiently amplified. The effect on primer extension of a 3'-terminal base that is mismatched with the template is described in Huang et al., 1992, Nucl. Acids Res. 20:4567-4573, incorporated herein by reference. The presence of misincorporated nucleotides may result in prematurely terminated strand synthesis, reducing the number of template strands for future rounds of amplification, and thus reducing the efficiency of long target amplification. Even low levels of nucleotide misincorporation may become critical for sequences longer than 10 kb. The data shown in FIG. 4 shows that the fidelity of DNA synthesis using gamma tagged dNTPs is improved for the native Taq polymerase making longer DNA extension possible without the need for adding polymerases with 3'-to 5' exonuclease, or "proofreading", activity as required in the long-distance PCR method developed by Cheng et al., U.S. Pat. Nos. 5,512,462, incorporated herein by reference. Thus, the present invention provides an improved PCR system for generating increased extension length PCR amplified DNA products comprising contacting a native Taq polymerase with gamma tagged dNTPs of this invention under PCR reaction conditions. The extended length PCR products are due to improved accuracy of base incorporation, resulting from the use of the gamma-modified dNTPs of this invention.

Figure 12:
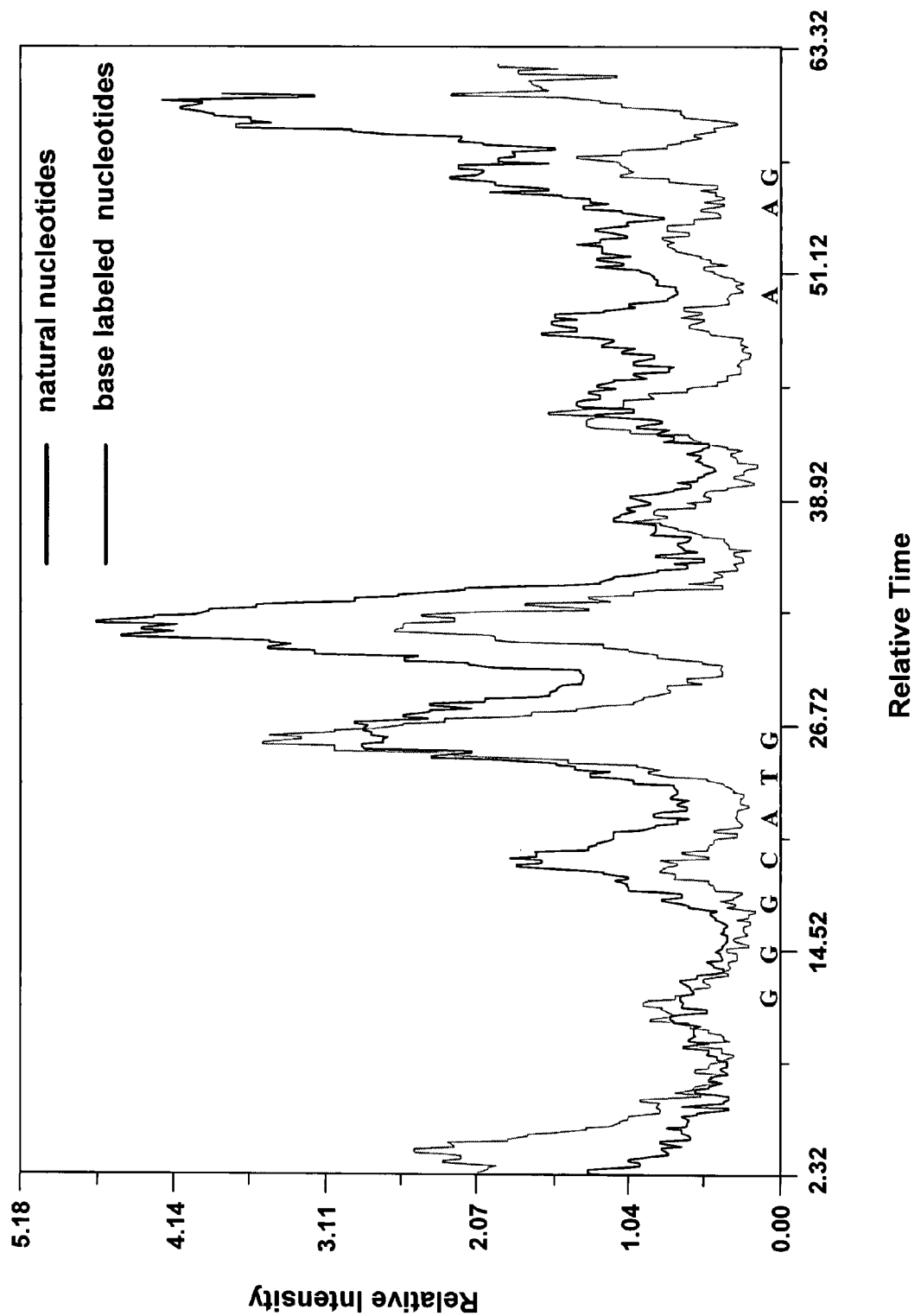
FIG. 12 depicts reaction products produced when the four natural nucleotides (dATP, dCTP, dGTP and dTTP) are used in the synthesis reaction (solid line) and reaction products produced when base-modified nucleotides are used in the synthesis reaction.

Signal Intensity and Reaction Kinetics Provide Information Concerning Base Identity Signal intensities for each nucleotide in the extended DNA strand are used to determine, confirm or support base identity data. Referring now to FIG. 12, the solid line corresponds to reaction products produced when the four natural nucleotides (dATP, dCTP, dGTP and dTTP) are included in the synthesis reaction. The dashed or broken line corresponds to reaction products produced when proprietary, base-modified nucleotides are included in the reaction. As is clearly demonstrated, sequence context and base modification(s) influence reaction product intensity and/or kinetics, and these identifying patterns are incorporated into proprietary base-calling software to provide a high confidence value for base identity at each sequenced position.

All references cited herein and listed in are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for sequencing a plurality of target nucleic acid molecules, the method comprising:

subjecting the plurality of target nucleic acid molecules to a polymerization reaction including a plurality of types of nucleotides or nucleotide analogs to yield a population of growing nucleic acid strands that are complementary to their respective target nucleic acid molecules, wherein the target nucleic acid molecule and/or a nucleic acid polymerase is attached to a support, where at least one of the types of nucleotides or nucleotide analogs includes a first atomic or molecular tag bonded to a nucleotide or nucleotide analog part released during incorporation; and optically identifying a time sequence of incorporation events, at least one of the incorporation events involving the incorporation of a tagged nucleotide or nucleotide analog into at least one growing nucleic acid strand in the population, where each event involving a tagged nucleotide or nucleotide analog is characterized by a change in a detectable property of the first tag.

2. A method for sequencing a plurality of target nucleic acid molecules, the method comprising:

subjecting the plurality of target nucleic acid molecules to a polymerization reaction in the presence of a plurality of types of nucleotides or nucleotide analogs to yield a population of growing nucleic acid strands that are complementary to their respective target nucleic acid molecules, wherein the target nucleic acid molecule and/or a nucleic acid polymerase is attached to a support, where at least one of the types of nucleotides or nucleotide analogs includes a first atomic or molecular tag bonded to a nucleotide or nucleotide analog part released during incorporation; and optically identifying in real-time or near real-time a time sequence of incorporation events, where at least one of the incorporation events involves the incorporation of a tagged nucleotide or nucleotide analog into at least one growing nucleic acid strand in the population, where each event involving a tagged nucleotide or nucleotide analog is characterized by a change in a detectable property of the first tag.

3. The method of claims 1 or 2, wherein the polymerase is selected from the group consisting of a DNA polymerase, reverse transcriptase, and mixtures thereof.

4. The method of claim 3, wherein the polymerase is a thermostable polymerase or a thermodegradable polymerase.

5. The method of claim 1, wherein the target nucleic acid molecules are selected from the group consisting of double-stranded DNA, single-stranded DNA, single stranded DNA hairpins, and DNA/RNA.

6. The method of claim 1, wherein the nucleotide analogs are selected from the group consisting of a ribonucleotide, a deoxyribonucleotide, a modified ribonucleotide, a modified deoxyribonucleotide, a peptide nucleotide, a modified peptide nucleotide, and a modified phosphate-sugar backbone nucleotide.

7. The method of claim 1, wherein the tagged nucleotides or nucleotide analogs types further include one additional tag or a plurality of additional tags.

8. The method of claim 1, wherein the first tags are selected from the group consisting of chromophores, fluorescent moieties, dyes, and fluorescent nanoparticles.

9. The method of claim 7, wherein the additional tag is or the additional tags are attached to the nucleotides or nucleotide analogs at a base, sugar moiety, or alpha phosphate.

10. The method of claim 1, wherein each nucleotide and nucleotide analog type includes a first tag and where the first tags make the nucleotide or nucleotide analog types distinguishable during the identifying step.

11. The method of claim 7, wherein three or less of the plurality of types of nucleotides or nucleotide analogs have a different tag.

12. The method according to claim 7, wherein the different types of nucleotides or nucleotide analogs have the same tag but are distinguished by different properties of the nucleotides or nucleotide analogs, and/or emission properties of the tags.

13. The method of claim 3, wherein the polymerase includes an atomic or molecular tag and the identifying is carried out by detecting interaction between the polymerase tag and the nucleotide, the nucleotide analog, or the tags on the nucleotide or nucleotide analog.

14. The method of claim 13, wherein the polymerase tag and at least one tag on at least one or the types of nucleotides or nucleotide analogs form a donor and acceptor pair and the interaction is fluorescence resonance energy transfer.

15. The method of claims 1 or 2, wherein the identifying is carried out by fluorescence resonance energy transfer.

16. The method of claims 1 or 2, wherein the identifying is performed by spectral wavelength discrimination, measurement and separation of fluorescence lifetimes, fluorophore identification, background suppression or a combination thereof.

17. The method of claims 1 or 2, wherein the plurality of target nucleic acids are attached to the support.

18. The method of claims 1 or 2, wherein each target nucleic acid is hybridized to a separate oligonucleotide which is attached to the support.

19. The method of claim 3, wherein the DNA polymerase is attached to the support.

20. The method of claims 1 or 2, wherein the identifying is carried out by reducing background noise resulting from free nucleotides or nucleotide analogs.

21. The method of claim 1, wherein the tag is attached to the terminal phosphate of the nucleotides or nucleotide analogs.

22. The method of claim 21, wherein the identifying is effected by detecting the tags attached to the nucleotides or nucleotide analogs.

23. The method of claim 3, wherein the polymerase lack 3' to 5' exonuclease activity.

* * * * *